US012583824B2

(12) United States Patent
Gao et al.

(10) Patent No.: US 12,583,824 B2
(45) Date of Patent: Mar. 24, 2026

(54) 6-MEMBERED HETEROARYLAMINOSULFONAMIDES FOR TREATING DISEASES AND CONDITIONS MEDIATED BY DEFICIENT CFTR ACTIVITY

(71) Applicant: Genzyme Corporation, Cambridge, MA (US)

(72) Inventors: Zhongli Gao, Bridgewater, NJ (US); Gregory Hurlbut, Bridgewater, NJ (US); Mark Munson, Bridgewater, NJ (US); Junkai Liao, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 821 days.

(21) Appl. No.: 17/742,172

(22) Filed: May 11, 2022

(65) Prior Publication Data

US 2023/0137585 A1 May 4, 2023

Related U.S. Application Data

(63) Continuation of application No. PCT/US2020/060176, filed on Nov. 12, 2020.

(60) Provisional application No. 62/934,287, filed on Nov. 12, 2019.

(51) Int. Cl.

| | |
|---|---|
| ***C07D 239/69*** | (2006.01) |
| ***A61K 31/4418*** | (2006.01) |
| ***A61K 31/444*** | (2006.01) |
| ***A61K 31/4545*** | (2006.01) |
| ***A61K 31/4965*** | (2006.01) |
| ***A61K 31/497*** | (2006.01) |
| ***A61K 31/505*** | (2006.01) |
| ***A61K 31/506*** | (2006.01) |
| ***A61K 45/06*** | (2006.01) |
| ***A61P 11/00*** | (2006.01) |
| ***C07D 213/76*** | (2006.01) |
| ***C07D 241/22*** | (2006.01) |
| ***C07D 401/12*** | (2006.01) |
| ***C07D 401/14*** | (2006.01) |
| ***C07D 403/04*** | (2006.01) |
| ***C07D 403/12*** | (2006.01) |
| ***C07D 403/14*** | (2006.01) |

(52) U.S. Cl.

CPC ........ *C07D 239/69* (2013.01); *A61K 31/4418* (2013.01); *A61K 31/444* (2013.01); *A61K 31/4545* (2013.01); *A61K 31/4965* (2013.01); *A61K 31/497* (2013.01); *A61K 31/505* (2013.01); *A61K 31/506* (2013.01); *A61K 45/06* (2013.01); *A61P 11/00* (2018.01); *C07D 213/76* (2013.01); *C07D 241/22* (2013.01); *C07D 401/12* (2013.01); *C07D 401/14* (2013.01); *C07D 403/04* (2013.01); *C07D 403/12* (2013.01); *C07D 403/14* (2013.01); *C07B 2200/07* (2013.01)

(58) Field of Classification Search

None

See application file for complete search history.

(56) References Cited

U.S. PATENT DOCUMENTS

| | | | | |
|---|---|---|---|---|
| 4,172,896 | A | 10/1979 | Uno et al. | |
| 5,358,970 | A | 10/1994 | Ruff et al. | |
| 5,427,798 | A | 6/1995 | Ludwig et al. | |
| 5,449,783 | A | 9/1995 | Saita et al. | |
| 5,541,231 | A | 7/1996 | Ruff et al. | |
| 5,731,000 | A | 3/1998 | Ruff et al. | |
| 5,763,493 | A | 6/1998 | Ruff et al. | |
| 5,856,347 | A | 1/1999 | Hashiguchi et al. | |
| 6,110,973 | A | 8/2000 | Young | |
| 8,999,976 | B2 | 4/2015 | Binch et al. | |
| 9,790,219 | B2 * | 10/2017 | Bastos .................. | A61K 45/06 |
| 2007/0022507 | P1 | 1/2007 | Scully | |
| 2009/0233975 | A1 | 9/2009 | Suetsugu et al. | |
| 2011/0184177 | A1 | 7/2011 | Hachtel et al. | |
| 2015/0005275 | A1 | 1/2015 | Plas et al. | |
| 2015/0045327 | A1 | 2/2015 | Van Der Plas et al. | |
| 2016/0095858 | A1 | 4/2016 | Miller et al. | |
| 2016/0120841 | A1 | 5/2016 | Kym et al. | |
| 2016/0122331 | A1 | 5/2016 | Kym et al. | |
| 2016/0355480 | A1 | 12/2016 | Altenbach et al. | |
| 2019/0248809 | A1 | 8/2019 | Clemens et al. | |
| 2023/0147360 | A1 | 5/2023 | Liao et al. | |
| 2023/0159438 | A1 | 5/2023 | Liao et al. | |
| 2023/0159439 | A1 | 5/2023 | Liao et al. | |

(Continued)

FOREIGN PATENT DOCUMENTS

| | | | |
|---|---|---|---|
| EP | 0790057 | A1 | 8/1997 |
| EP | 3464282 | A1 | 4/2019 |

(Continued)

OTHER PUBLICATIONS

Weijlard et al., J. Am. Chem. Soc., 67, 802-806 (Year: 1945).*

(Continued)

*Primary Examiner* — Adam C Milligan

*Assistant Examiner* — Jason M. Nolan

(74) *Attorney, Agent, or Firm* — Goodwin Procter LLP

(57) ABSTRACT

The invention relates to heteroaryl compounds, pharmaceutically acceptable salts thereof, and pharmaceutical preparations thereof. Also described herein are compositions and the use of such compounds in methods of treating diseases and conditions mediated by deficient CFTR activity, in particular cystic fibrosis.

44 Claims, No Drawings

(56) References Cited

U.S. PATENT DOCUMENTS

| | | | |
|---|---|---|---|
| 2024/0002374 A1 | 1/2024 | Liao et al. |
| 2025/0255859 A1 | 8/2025 | Hurlbut |

FOREIGN PATENT DOCUMENTS

| | | | |
|---|---|---|---|
| JP | H07149745 A | 6/1995 |
| JP | 2007504255 A | 3/2007 |
| JP | 2017074057 A | 4/2017 |
| WO | WO-9616650 A1 | 6/1996 |
| WO | WO-98024782 A2 | 6/1998 |
| WO | WO-03039451 A2 | 5/2003 |
| WO | WO-2005075435 A1 | 8/2005 |
| WO | WO-2005120497 A2 | 12/2005 |
| WO | WO-2006002421 | 1/2006 |
| WO | WO-2006069656 A1 | 7/2006 |
| WO | WO-2006113704 A2 | 10/2006 |
| WO | WO-2008000408 A1 | 1/2008 |
| WO | WO-2008147952 A1 | 12/2008 |
| WO | WO-2009074575 A2 | 6/2009 |
| WO | WO-2009076593 A1 | 6/2009 |
| WO | WO-2010048526 A2 | 4/2010 |
| WO | WO-2010048573 A1 | 4/2010 |
| WO | WO-2011072241 A1 | 6/2011 |
| WO | WO-20110113894 A1 | 9/2011 |
| WO | WO-2013038373 A1 | 3/2013 |
| WO | WO-2013038378 A1 | 3/2013 |
| WO | WO-2013038381 A1 | 3/2013 |
| WO | WO-2013038386 A1 | 3/2013 |
| WO | WO-2013038390 A1 | 3/2013 |
| WO | WO-2013043720 A1 | 3/2013 |
| WO | WO-2014180562 A1 | 11/2014 |
| WO | WO-2014186704 A2 | 11/2014 |
| WO | WO-2015018823 A1 | 2/2015 |
| WO | WO-2015138909 A1 | 9/2015 |
| WO | WO-2015138934 A1 | 9/2015 |
| WO | WO-2016183173 A1 | 11/2016 |
| WO | WO-2018042316 A1 | 3/2018 |
| WO | WO-2019161078 A1 | 8/2019 |
| WO | WO-2020206080 A1 | 10/2020 |
| WO | WO-2021097054 A1 | 5/2021 |
| WO | WO-2021097057 A1 | 5/2021 |
| WO | WO-2021113808 A1 | 6/2021 |
| WO | WO-20210113806 A1 | 6/2021 |
| WO | WO-2022032068 | 2/2022 |
| WO | WO-2022076622 | 4/2022 |
| WO | WO-2023034992 | 3/2023 |
| WO | WO-2024097227 A1 | 5/2024 |

OTHER PUBLICATIONS

Hitchin, et al., Development and evaluation of selective, reversible LSD1 inhibitors derived from fragments, MedChemComm, 4(11): 1513 (2013).
Jenkins et al., A 3D similarity method for scaffold hopping from the known drugs or natural ligands to new chemotypes, J. Medical Chemistry, 47(25): 6144-6159 (2004).
Ivacaftor Prescribing Information, 17 pages, Vertex Pharmaceuticals, Feb. 2017.
PCT/US2020/060176 International Preliminary Report on Patentability mailed May 27, 2022, 9 pages.
PCT/US2020/060176 International Search Report and Written Opinion mailed Jan. 29, 2021, 12 pages.
PCT/US2020/060180 International Preliminary Report on Patentability mailed Mar. 27, 2022, 9 pages.
PCT/US2020/060180 International Search Report and Written Opinion mailed Feb. 24, 2021, 13 pages.
Saikachi et al., "Synthesis of the Furan Derivatives. XLVII. Synthesis of 5, 6-Bis (5-nitro-2-furyl)-2-aminopyrazine and Its Related Compound", Yakugaku Zasshi. 89(8):1071-1077 (1969).
Wang, et al., Synthesis and biological evaluation of diarylthiazole derivatives as antimitotic and antivascular agents with potent antitumor activity, Bioorganic & Medicinal Chemistry, 23: 3337-3350 (2015).
Yoshii et al., "Antiviral and Antibacterial Activities of 3-(Substituted benzenesulfonylamino)-5, 6-di(p-substituted phenyl)-1, 2, 4-triazines", Yakugaku Zasshi. 108(1):50-57 (1988).
Azam S., et al, The Ageing Brain: Molecular and Cellular Basis of Neurodegeneration, Front Cell Dev Biol, 9:683459 (2021).
Chiba, T., Emerging Therapeutic Strategies in Alzheimer's Disease, Intech, 181-225 (2013).
Damia, G., et al., Contemporary pre-clinical development of anticancer agents—What are the optimal preclinical models?, Eur J Cancer, 45(16):2768-2781 (2009).
Derichs, Targeting a genetic defect: cystic fibrosis transmembrane conductance regulator modulators in cystic fibrosis, European Respiratory Review, 22:127, 58-65 (2013).
Felis, A., et al., Current and Investigational Therapeutics for Fabry Disease, Kidney Int Rep, 5(4):407-413 (2020).
Ghelani, D.P., et al., Emerging Cystic Fibrosis Transmembrane Conductance Regulator Modulators as New Drugs for Cystic Fibrosis: A Portrait of in VitroÂ Pharmacology and Clinical Translation, ACS Pharmacol Transl Sci., 3(1):4-10 (2019).
Gregory, R. J. et al., Expression and charaterization of the cystic fibrosis transmembrane conductance regulator, Nature, 347:382-386 (1990).
Guan, X., et al., Dysregulated Chemokine Signaling in Cystic Fibrosis Lung Disease: A Potential Therapeutic Target, Curr Drug Targets, 17(13): 1535-1544 (2016).
Johnson, J.I., et al., Relationships between drug activity in NCI preclinical in vitro and in vivo models and early clinical trials, Br J Cancer, 84(10):1424-1431 (2001).
Ledford, H., US cancer institute overhauls cell lines, Nature, 530(7591):391 (2016).
Lopes-Pacheco, M., CFTR Modulators: The Changing Face of Cystic Fibrosis in the Era of Precision Medicine, Front Pharmacol., 10:1662 (2020).
Makrilakis, K., Pathophysiology of Type 2 diabetes, Chapter 3 in Diabetes in Clinical Practice: Questions and Answers from Case Studies, Nicholas Katsilambros et al. eds. John Wiley & Sons: 2006, pp. 43-58.
Ocana, A., et al., Preclinical development of molecular targeted agents for cancer, Nat Rev Clin Oneal, 8(4):200-209 (2011).
PCT/US2020/063586 International Preliminary Report on Patentability mailed Jun. 16, 2022.
PCT/US2020/063586 International Search Report and Written Opinion mailed Feb. 15, 2021.
PCT/US2020/063589 International Preliminary Report on Patentability mailed Jun. 16, 2022.
PCT/US2020/063589 International Search Report and Written Opinion mailed Feb. 11, 2021.
PCT/US2020/063590 International Preliminary Report on Patentability mailed Jun. 16, 2022.
PCT/US2020/063590 International Search Report and Written Opinion mailed Feb. 15, 2021.
PCT/US2024/060181 International Search Report and Written Opinion mailed Mar. 25, 2025.
Rich, D. P. et al., Expression of cystic fibrosis transmembrane conductance regulator corrects defective chloride channel regulation in cystic fibrosis airway epithelial cells, Nature, 347:358-362 (1990).
Riordan, J. R. et al., Identification of the Cystic Fibrosis Gene: Cloning and Characterization of Complementary DNA, Science, 245:1066-1073 (1989).
Sharma, S.V., et al., Cell line-based platforms to evaluate the therapeutic efficacy of candidate anticancer agents, Nat Rev Cancer, 10(4):241-53 (2010).
Stavrou, M., et al., Genetic mechanisms of peripheral nerve disease, Neurosci Lett, 742:135357 (2021).
Types of CFTR Mutations, Online: "https://www.cff.org/research-clinical-trials/types-cftr-mutations", accessed Jun. 2, 2025.
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.

(56) References Cited

OTHER PUBLICATIONS

Van Goor, F., et al, Correction of the F508del-CFTR protein processing defect in vitro by the investigational drug VX-809, Proc Natl Acad Sci USA, 108(46):18843-8 (2011).

* cited by examiner

6-MEMBERED HETEROARYLAMINOSULFONAMIDES FOR TREATING DISEASES AND CONDITIONS MEDIATED BY DEFICIENT CFTR ACTIVITY

RELATED APPLICATIONS

This application is a continuation of International Application No. PCT/US2020/060176, filed Nov. 12, 2020, which claims priority to U.S. Provisional Application No. 62/934,287, filed Nov. 12, 2019, each of which are incorporated herein by reference in their entirety.

BACKGROUND

Cystic fibrosis (CF), an autosomal recessive disorder, is caused by functional deficiency of the cAMP-activated plasma membrane chloride channel, cystic fibrosis transmembrane conductance regulator (CFTR), which can result in damage to the lung, pancreas, and other organs. The gene encoding CFTR has been identified and sequenced (See Gregory, R. J. et al. (1990) Nature 347:382-386; Rich, D. P. et al. (1990) Nature 347:358-362; Riordan, J. R. et al. (1989) Science 245:1066-1073). CFTR, a member of the ATP binding cassette (ABC) superfamily is composed of two six membrane-spanning domains (MSD1 and MSD2), two nucleotide binding domains (NBD1 and NBD2), a regulatory region (R) and four cytosolic loops (CL1-4). Normally, CFTR protein is located primarily in the apical membrane of epithelial cells where it functions to conduct anions, including chloride, bicarbonate and thiocyanate into and out of the cell. CFTR may have a regulatory role over other electrolyte channels, including the epithelial sodium channel ENaC.

In cystic fibrosis patients, the absence or dysfunction of CFTR leads to exocrine gland dysfunction and a multisystem disease, characterized by pancreatic insufficiency and malabsorption, as well as abnormal mucociliary clearance in the lung, mucostasis, chronic lung infection and inflammation, decreased lung function and ultimately respiratory failure.

While more than 1,900 mutations have been identified in the CFTR gene, a detailed understanding of how each CFTR mutation may impact channel function is known for only a subset. (Derichs, European Respiratory Review, 22:127, 58-65 (2013)). The most frequent CFTR mutation is the in-frame deletion of phenylalanine at residue 508 (ΔF508) in the first nucleotide binding domain (NBD1). Over 80% of cystic fibrosis patients have the deletion at residue 508 in at least one CFTR allele. The loss of this key phenylalanine renders the NBD1 domain of CFTR conformationally unstable at physiological temperature and compromises the integrity of the interdomain interface between NBD1 and CFTR's second transmembrane domain (ICL4). The ΔF508 mutation causes production of misfolded CFTR protein which, rather than traffic to the plasma membrane, is instead retained in the endoplasmic reticulum and targeted for degradation by the ubiquitin-proteasome system.

The loss of a functional CFTR channel at the plasma membrane disrupts ionic homeostasis and airway surface hydration leading to reduced lung function. Reduced periciliary liquid volume and increased mucus viscosity impede mucociliary clearance resulting in chronic infection and inflammation. In the lung, the loss of CFTR-function leads to numerous physiological effects downstream of altered anion conductance that result in the dysfunction of additional organs such as the pancreas, intestine and gall bladder.

Guided, in part, by studies of the mechanistic aspects of CFTR misfolding and dysfunction, small molecule CFTR modulators have been identified that can act as correctors and/or potentiators of CFTR. Despite the identification of compounds that modulate CFTR, there is no cure for this fatal disease and identification of new compounds and new methods of therapy are needed as well as new methods for treating or lessening the severity of cystic fibrosis and other CFTR mediated conditions and diseases in a patient.

SUMMARY

Disclosed herein are compounds of Formula (I):

(I)

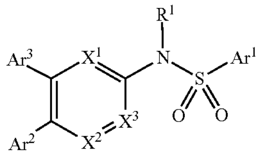

wherein:

$X^1$ is CH or N;

$X^2$ is CH or N;

$X^3$ is CH or N; wherein at least one of $X^1$, $X^2$ or $X^3$ is N;

$R^1$ is hydrogen or $C_{1-6}$ alkyl;

$Ar^1$ is aryl or 5-6 membered heteroaryl substituted with 0-3 occurrences of $R^2$;

each $R^2$ is independently halo, $C_{1-6}$ alkyl, $C_{1-6}$ haloalkyl, $C_{1-6}$ alkoxy, $C_{1-6}$ haloalkoxy, —$NR^aR^b$ or 3-8 membered heterocyclyl substituted with 0-3 occurrences of $R^5$;

$Ar^2$ is aryl or 5-6 membered heteroaryl substituted with 0-3 occurrences of $R^3$;

each $R^3$ is independently halo, $C_{1-6}$ alkyl, $C_{1-6}$ alkoxy, $C_{1-6}$ haloalkyl, $C_{1-6}$ haloalkoxy, $C_{3-8}$ cycloalkyl substituted with 0-3 occurrences of $R^5$ or 3-8 membered heterocyclyl substituted with 0-3 occurrences of $R^5$;

$Ar^3$ is aryl or 5-6 membered heteroaryl substituted with 0-3 occurrences of $R^4$;

each $R^4$ is independently halo, $C_{1-6}$ alkyl, $C_{1-6}$ haloalkyl, $C_{1-6}$ alkoxy or $C_{1-6}$ haloalkoxy;

$R^a$ is H or $C_{1-4}$ alkyl;

$R^b$ is H, $C_{1-4}$ alkyl, —$SO_2$—$C_{1-6}$ alkyl, $C_{3-8}$ cycloalkyl, or 3-8 membered heterocyclyl substituted with 0-3 occurrences of $R^5$;

each $R^5$ is independently hydroxyl, $CO_2H$, $C_{1-4}$ alkyl, $C_{1-4}$ alkoxy, $C_{1-4}$ haloalkyl or $C_{1-4}$ haloalkoxy.

Disclosed herein are methods of treating deficient CFTR activity, thereby treating a disease or condition mediated by deficient CFTR activity. Such diseases and conditions include, but are not limited to, cystic fibrosis, congenital bilateral absence of vas deferens (CBAVD), acute, recurrent, or chronic pancreatitis, pancreatic steatorrhea, disseminated bronchiectasis, asthma, allergic pulmonary aspergillosis, chronic obstructive pulmonary disease (COPD), chronic rhinosinusitis, nasal polyposis, dry eye disease, protein C deficiency, abetalipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, congenital pneumonia, nontuberculous mycobacterial infection, constipation, pancreatic insufficiency, celiac disease, intestinal atresia, hereditary emphysema, and Sjogren's syndrome. In some embodiments, the disease is cystic fibrosis.

In certain embodiments, the present invention provides a pharmaceutical composition suitable for use in a subject in the treatment or prevention of disease and conditions associate with deficient CFTR activity, comprising an effective amount of any of the compounds described herein (e.g., a compound of the invention, such as a compound of formula (I)), and one or more pharmaceutically acceptable excipients. In certain embodiments, the pharmaceutical preparations may be for use in treating or preventing a condition or disease as described herein.

Provided herein are combination therapies of compounds of formula (I) with CFTR-active agents that can enhance the therapeutic benefit beyond the ability of the primary therapy alone.

DETAILED DESCRIPTION

Disclosed herein are compounds of Formula (I):

(I)

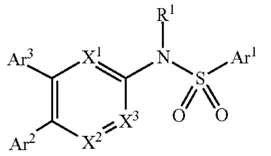

wherein:

$X^1$ is CH or N;

$X^2$ is CH or N;

$X^3$ is CH or N; wherein at least one of $X^1$, $X^2$ or $X^3$ is N;

$R^1$ is hydrogen or $C_{1-6}$ alkyl;

$Ar^1$ is aryl or 5-6 membered heteroaryl substituted with 0-3 occurrences of $R^2$;

each $R^2$ is independently halo, $C_{1-6}$ alkyl, $C_{1-6}$ haloalkyl, $C_{1-6}$ alkoxy, $C_{1-6}$ haloalkoxy, —$NR^aR^b$ or 3-8 membered heterocyclyl substituted with 0-3 occurrences of $R^5$;

$Ar^2$ is aryl or 5-6 membered heteroaryl substituted with 0-3 occurrences of $R^3$;

each $R^3$ is independently halo, $C_{1-6}$ alkyl, $C_{1-6}$ alkoxy, $C_{1-6}$ haloalkyl, $C_{1-6}$ haloalkoxy, $C_{3-8}$ cycloalkyl substituted with 0-3 occurrences of $R^5$ or 3-8 membered heterocyclyl substituted with 0-3 occurrences of $R^5$;

$Ar^3$ is aryl or 5-6 membered heteroaryl substituted with 0-3 occurrences of $R^4$;

each $R^4$ is independently halo, $C_{1-6}$ alkyl, $C_{1-6}$ haloalkyl, $C_{1-6}$ alkoxy or $C_{1-6}$ haloalkoxy;

$R^a$ is H or $C_1$-4 alkyl;

$R^b$ is H, $C_{1-4}$ alkyl, —$SO_2$—$C_{1-6}$ alkyl, $C_{3-8}$ cycloalkyl or 3-8 membered heterocyclyl substituted with 0-3 occurrences of $R^5$;

each $R^5$ is independently hydroxyl, $CO_2H$, $C_{1-4}$ alkyl, $C_{1-4}$ alkoxy, $C_{1-4}$ haloalkyl or $C_{1-4}$ haloalkoxy.

In some embodiments, $X^1$ is N and $X^2$ and $X^3$ are CH. In some embodiments, $X^1$ and $X^2$ are N and $X^3$ is CH. In some embodiments, $X^1$ and $X^3$ are N and $X^2$ is CH.

In some embodiments, $R^1$ is hydrogen. In some embodiments, $R^1$ is $C_{1-6}$ alkyl (e.g., methyl).

In some embodiments, $Ar^1$ is aryl (e.g., phenyl) substituted with 0-3 occurrences of $R^2$. In some embodiments, $Ar^1$ is phenyl substituted with 0-3 occurrences of $R^2$. In some embodiments, $Ar^1$ is unsubstituted phenyl. In some embodiments, $Ar^1$ is phenyl substituted with 1 occurrence of $R^2$. In some embodiments, $R^2$ is —$NR^aR^b$. In some embodiments, $R^a$ is hydrogen and $R^b$ is hydrogen. In some embodiments, $R^a$ is hydrogen and $R^b$ is —$SO_2$—$C_{1-6}$ alkyl (e.g., —$SO_2$-Me). In some embodiments, $R^a$ is hydrogen and $R^b$ is 3-8 membered heterocyclyl substituted with 0-3 occurrences of $R^5$. In some embodiments, $R^a$ is hydrogen and $R^b$ is $C_{3-8}$ cyclopropyl substituted with 0-3 occurrences of $R^5$. In some embodiments, $R^a$ is hydrogen and $R^b$ is cyclobutyl substituted with 2 occurrences of $R^5$. In some embodiments, one occurrence of $R^5$ is hydroxyl and the other occurrence of $R^5$ is $C_{1-4}$ alkyl (e.g., methyl).

In some embodiments, $Ar^1$ is a 5-6 membered heteroaryl substituted with 0-3 occurrences of $R^2$. In some embodiments, $Ar^1$ is 5 membered heteroaryl substituted with 0-3 occurrences of $R^2$. In some embodiments, $Ar^1$ is pyrazolyl substituted with 0-3 occurrences of $R^2$. In some embodiments, $Ar^1$ is 4-pyrazolyl substituted with 0-3 occurrences of $R^2$. In some embodiments, $Ar^1$ is 4-pyrazolyl substituted with 2 occurrences of $R^2$. In some embodiments, both $R^2$ are $C_{1-6}$ alkyl (e.g., methyl). In some embodiments, $Ar^1$ is 1,3-dimethyl-4-pyrazolyl.

In some embodiments, $Ar^1$ is a 6-membered heteroaryl substituted with 0-3 occurrences of $R^2$.

In some embodiments, $Ar^1$ is 2-pyridinyl substituted with 0-3 occurrences of $R^2$. In some embodiments, $Ar^1$ is 2-pyridinyl substituted with 0 occurrences of $R^2$. In some embodiments, $Ar^1$ is 2-pyridinyl substituted with 1 occurrence of $R^2$. In some embodiments, $R^2$ is halo (e.g., chloro). In some embodiments, $Ar^1$ is 3-chloro-2-pyridinyl. In some embodiments, $R^2$ is —$NR^aR^b$. In some embodiments, $R^a$ is hydrogen and $R^b$ is hydrogen. In some embodiments, $Ar^1$ is 3-amino-2-pyridinyl. In some embodiments, $R^2$ is 3-8 membered heterocyclyl substituted with 0-3 occurrences of $R^5$. In some embodiments, $R^2$ is 1-piperidinyl substituted with 0-3 occurrences of $R^5$. In some embodiments, $R^2$ is 1-piperidinyl substituted with 2 occurrences of $R^5$. In some embodiments, one occurrence of $R^5$ is hydroxyl and the other occurrence of $R^5$ is $C_{1-4}$ alkyl (e.g., methyl). In some embodiments, $Ar^1$ is

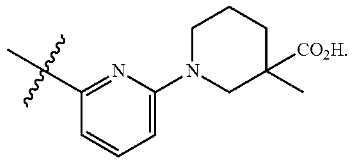 [SMILES: *c1cccc(N2CCCC(C)(C(=O)O)C2)n1]

In some embodiments, $Ar^1$ is 3-pyridinyl substituted with 0-3 occurrences of $R^2$. In some embodiments, $Ar^1$ is 3-pyridinyl substituted with 0 occurrences of $R^2$.

In some embodiments, $Ar^2$ is aryl (e.g., phenyl) substituted with 0-3 occurrences of $R^3$. In some embodiments, $Ar^2$ is phenyl substituted with 0-3 occurrences of $R^3$. In some embodiments, $Ar^2$ is phenyl substituted with 0 occurrences of $R^3$. In some embodiments, $Ar^2$ is phenyl substituted with 1 occurrence of $R^3$. In some embodiments, $R^3$ is substituted at the ortho position. In some embodiments, $R^3$ is substituted at the meta position. In some embodiments, $R^3$ is substituted at the para position. In some embodiments, $R^3$ is $C_{1-6}$ alkoxy (e.g., 2,2-dimethylpropoxy or 3,3-dimethylbutoxy). In some embodiments, $R^3$ is $C_{1-6}$ haloalkoxy (e.g., trifluoromethoxy, 2,2,2-trifluoroethoxy, 2,2-difluoro-3,3-dimethylbutoxy or 2,2-dimethyl-3,3,3-trifluoropropoxy). In some embodiments, $R^3$ is $C_{3-8}$ cycloalkyl substituted with 0-3 occurrences of $R^5$. In some embodiments, $R^3$ is cyclopentyl substituted with 0-3 occurrences of $R^5$. In some embodiments, $R^3$ is cyclopentyl substituted with 1 occurrence of $R^5$. In some embodiments, $R^5$ is $C_{1-4}$ haloalkoxy (e.g., trifluoromethoxy).

In some embodiments, $Ar^2$ is phenyl substituted with 2 occurrences of $R^3$. In some embodiments, one occurrence of $R^3$ is halo (e.g., fluoro or chloro) and the other occurrence of $R^3$ is $C_{1-6}$ alkoxy (e.g., 2,2-dimethylpropoxy). In some embodiments, $Ar^2$ is

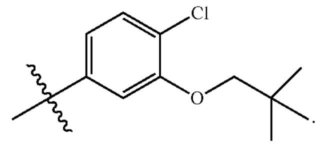 [SMILES: *c1ccc(Cl)c(OCC(C)(C)C)c1]

In some embodiments, one occurrence of $R^3$ is halo (e.g., fluoro or chloro) and the other occurrence of $R^3$ is $C_{1-6}$ haloalkoxy (e.g., 2,2-dimethyl-3,3,3-trifluoropropoxy). In some embodiments, $Ar^2$ is

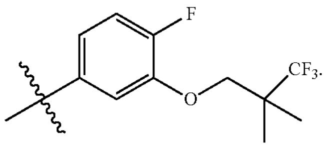 [SMILES: *c1ccc(F)c(OCC(C)(C)C(F)(F)F)c1]

In some embodiments, $Ar^2$ is 5-6 membered heteroaryl (e.g., 1-pyrazolyl) substituted with 0-3 occurrences of $R^3$. In some embodiments, $Ar^2$ is 1-pyrazolyl substituted with 0-3 occurrences of $R^3$. In some embodiments, $Ar^2$ is 1-pyrazolyl substituted with 1 occurrence of $R^3$. In some embodiments, $R^3$ is $C_{1-6}$ haloalkoxy (e.g., 2,2-difluoro-2,2-dimethylbutoxy). In some embodiments, $Ar^2$ is

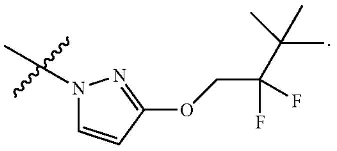 [SMILES: *n1ccc(OCC(F)(F)C(C)(C)C)n1]

In some embodiments, $Ar^3$ is aryl (e.g., phenyl) substituted with 0-3 occurrences of $R^4$. In some embodiments, $Ar^3$ is phenyl substituted with 0-3 occurrences of $R^4$. In some embodiments, $Ar^3$ is phenyl substituted with 0 occurrences of $R^4$. In some embodiments, $Ar^3$ is phenyl substituted with 1 occurrence of $R^4$. In some embodiments, $R^4$ is substituted at the ortho position. In some embodiments, $R^4$ is substituted at the meta position. In some embodiments, $R^4$ is substituted at the para position. In some embodiments, $R^4$ is $C_{1-6}$ alkyl (e.g., isopropyl or ethyl). In some embodiments, $R^4$ is $C_{1-6}$ haloalkyl (e.g., trifluoromethyl).

In some embodiments, $Ar^3$ is phenyl substituted with 2 occurrences of $R^4$. In some embodiments, one occurrence of $R^4$ is halo (e.g., fluoro or chloro) and the other occurrence of $R^4$ is $C_{1-6}$ alkyl (e.g., isopropyl). In some embodiments, $Ar^3$ is 2-isopropyl-4-chlorophenyl. In some embodiments, both occurrences of $R^4$ are $C_{1-6}$ alkyl (e.g., methyl). In some embodiments, $Ar^3$ is 2,6-dimethylphenyl.

In some embodiments, the compound is a compound selected from the following table:

| # | Compound |
|---|---|
| 2 | 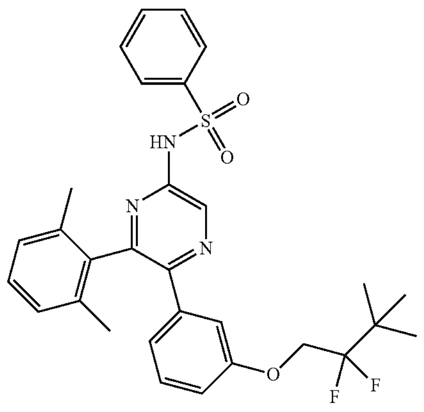 [SMILES: Cc1cccc(C)c1-c1nc(NS(=O)(=O)c2ccccc2)cnc1-c1cccc(OCC(F)(F)C(C)(C)C)c1] |
| 5 | 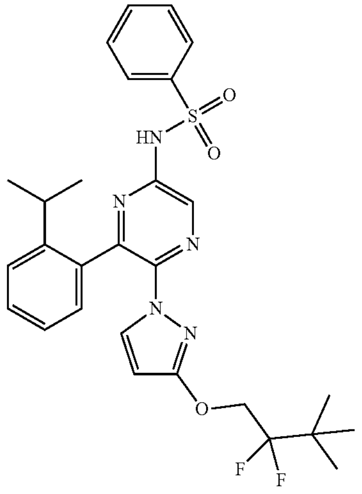 [SMILES: CC(C)c1ccccc1-c1nc(NS(=O)(=O)c2ccccc2)cnc1-n1ccc(OCC(F)(F)C(C)(C)C)n1] |
| 9b | 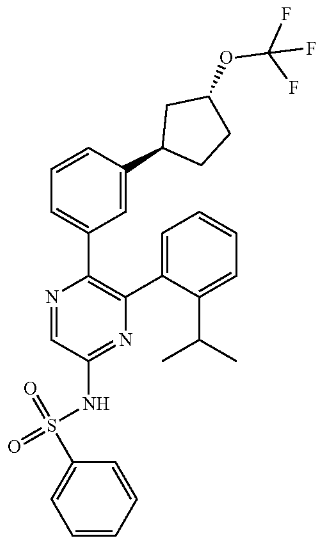 [SMILES: CC(C)c1ccccc1-c1nc(NS(=O)(=O)c2ccccc2)cnc1-c1cccc([C@@H]2CC[C@@H](OC(F)(F)F)C2)c1] |

-continued
| # | Compound |
|---|---|
| 27b | 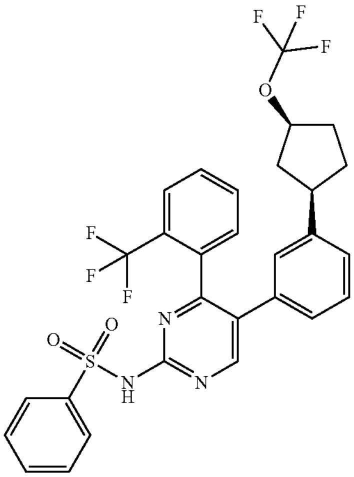 [SMILES: O=S(=O)(Nc1ncc(-c2cccc([C@@H]3CC[C@H](OC(F)(F)F)C3)c2)c(-c2ccccc2C(F)(F)F)n1)c1ccccc1] |
| 14 | 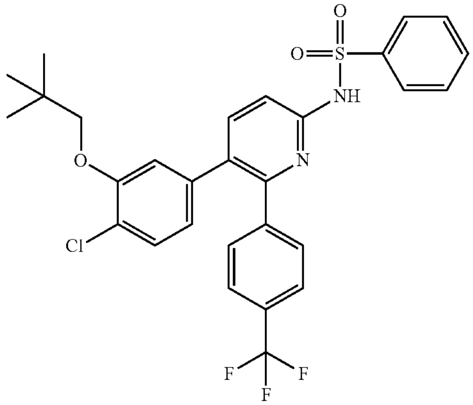 [SMILES: CC(C)(C)COc1cc(-c2ccc(NS(=O)(=O)c3ccccc3)nc2-c2ccc(C(F)(F)F)cc2)ccc1Cl] |
| 8b | 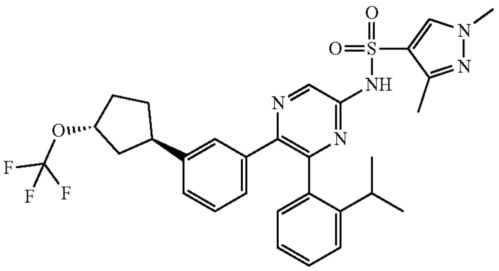 [SMILES: Cc1nn(C)cc1S(=O)(=O)Nc1cnc(-c2cccc([C@@H]3CC[C@@H](OC(F)(F)F)C3)c2)c(-c2ccccc2C(C)C)n1] |
| 18 | 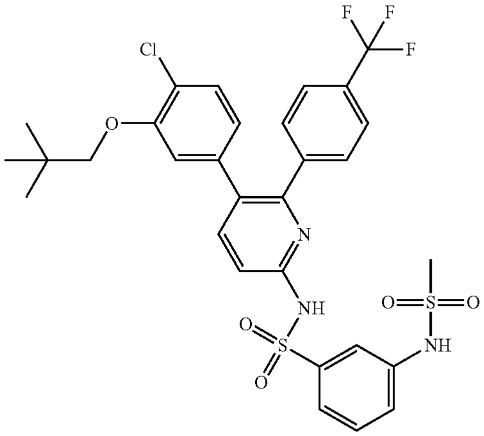 [SMILES: CC(C)(C)COc1cc(-c2ccc(NS(=O)(=O)c3cccc(NS(C)(=O)=O)c3)nc2-c2ccc(C(F)(F)F)cc2)ccc1Cl] |
-continued
| # | Compound |
|---|---|
| 8a | 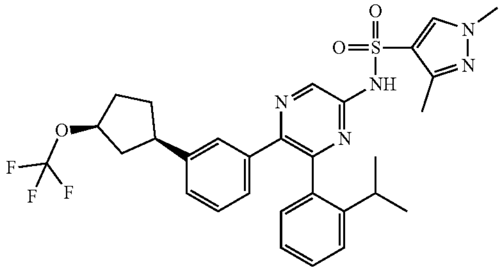 |
| 29b | 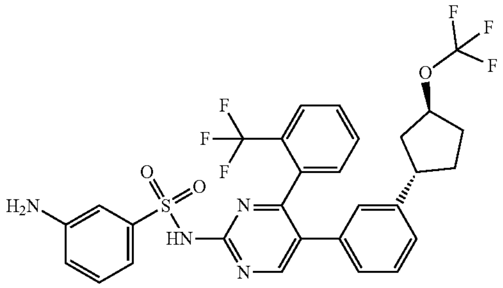 [SMILES: Nc1cccc(S(=O)(=O)Nc2ncc(-c3cccc([C@H]4CC[C@H](OC(F)(F)F)C4)c3)c(-c3ccccc3C(F)(F)F)n2)c1] |
| 30a | 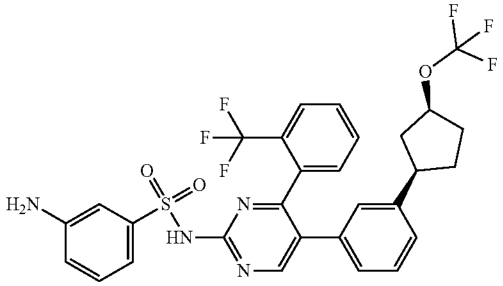 [SMILES: Nc1cccc(S(=O)(=O)Nc2ncc(-c3cccc([C@@H]4CC[C@H](OC(F)(F)F)C4)c3)c(-c3ccccc3C(F)(F)F)n2)c1] |
| 29a | 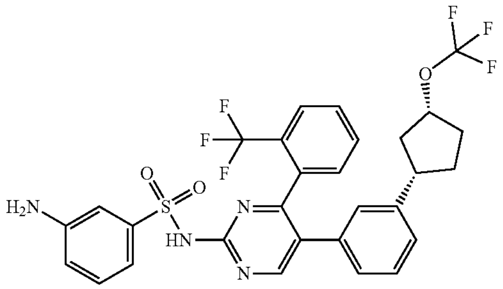 [SMILES: Nc1cccc(S(=O)(=O)Nc2ncc(-c3cccc([C@H]4CC[C@@H](OC(F)(F)F)C4)c3)c(-c3ccccc3C(F)(F)F)n2)c1] |

-continued
| # | Compound |
| --- | --- |
| 6a | 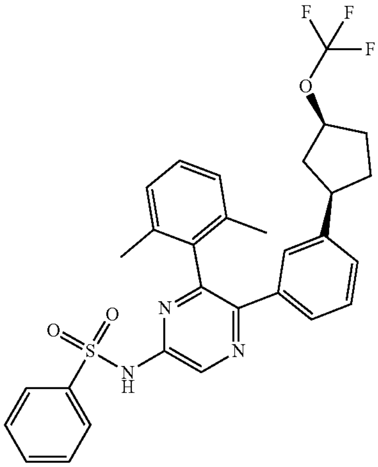 [SMILES: Cc1cccc(C)c1-c1nc(NS(=O)(=O)c2ccccc2)cnc1-c1cccc([C@@H]2CC[C@H](OC(F)(F)F)C2)c1] |
| 24 | 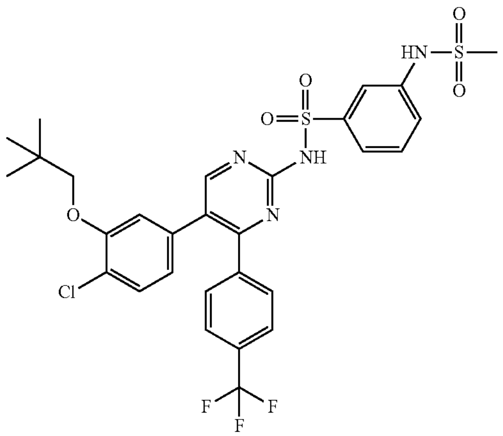 [SMILES: CC(C)(C)COc1cc(-c2cnc(NS(=O)(=O)c3cccc(NS(C)(=O)=O)c3)nc2-c2ccc(C(F)(F)F)cc2)ccc1Cl] |
| 26 | 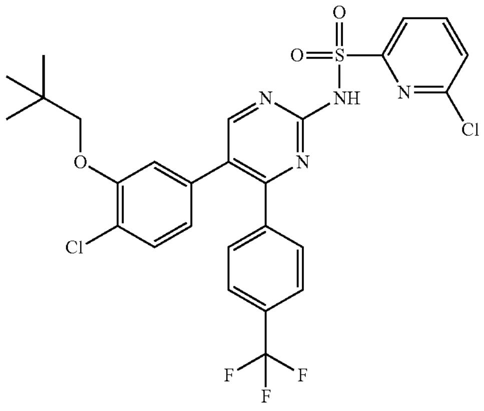 [SMILES: CC(C)(C)COc1cc(-c2cnc(NS(=O)(=O)c3cccc(Cl)n3)nc2-c2ccc(C(F)(F)F)cc2)ccc1Cl] |
-continued
| # | Compound |
| --- | --- |
| 28a | 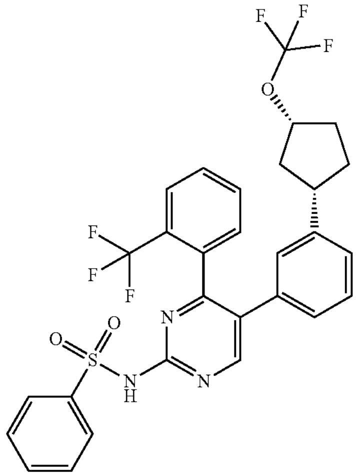 [SMILES: O=S(=O)(Nc1ncc(-c2cccc([C@H]3CC[C@@H](OC(F)(F)F)C3)c2)c(-c2ccccc2C(F)(F)F)n1)c1ccccc1] |
| 27a | 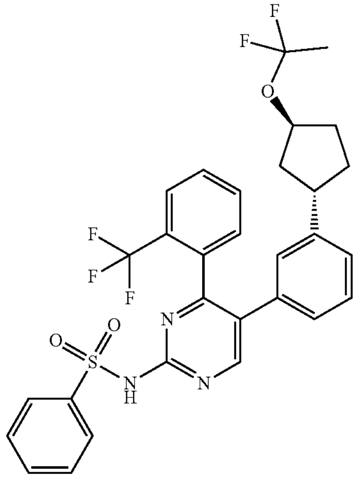 [SMILES: CC(F)(F)O[C@H]1CC[C@H](c2cccc(-c3cnc(NS(=O)(=O)c4ccccc4)nc3-c3ccccc3C(F)(F)F)c2)C1] |
| 22 | 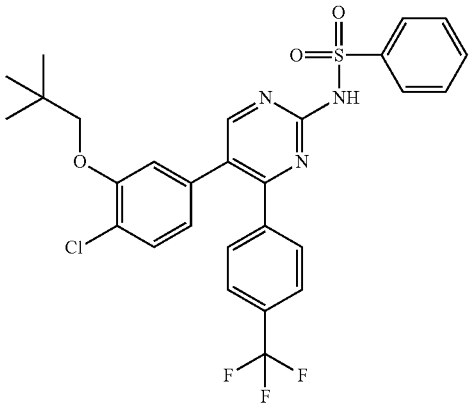 |

| # | Compound |
|---|---|
| 28b | 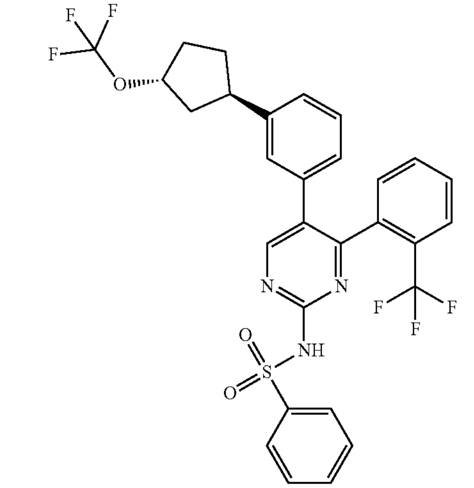 [SMILES: O=S(=O)(Nc1ncc(-c2cccc([C@@H]3CC[C@@H](OC(F)(F)F)C3)c2)c(-c2ccccc2C(F)(F)F)n1)c1ccccc1] |
| 7a | 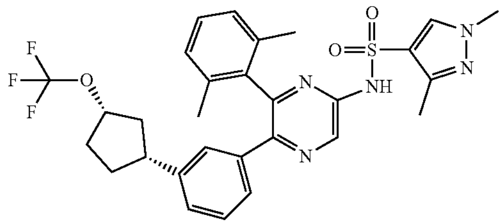 [SMILES: Cc1cccc(C)c1-c1nc(NS(=O)(=O)c2cn(C)nc2C)cnc1-c1cccc([C@@H]2CC[C@H](OC(F)(F)F)C2)c1] |
| 17 | 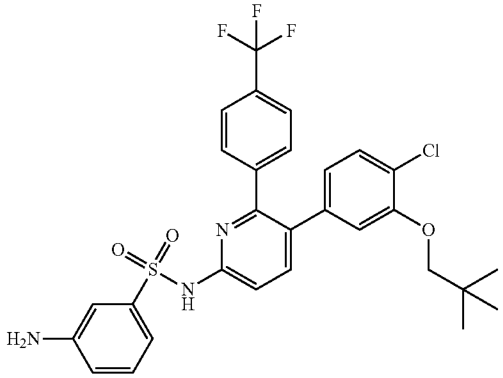 [SMILES: CC(C)(C)COc1cc(-c2ccc(NS(=O)(=O)c3cccc(N)c3)nc2-c2ccc(C(F)(F)F)cc2)ccc1Cl] |
| 19 | 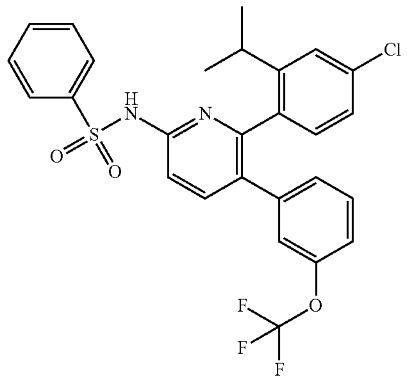 [SMILES: CC(C)c1cc(Cl)ccc1-c1nc(NS(=O)(=O)c2ccccc2)ccc1-c1cccc(OC(F)(F)F)c1] |
| # | Compound |
|---|---|
| 30b | 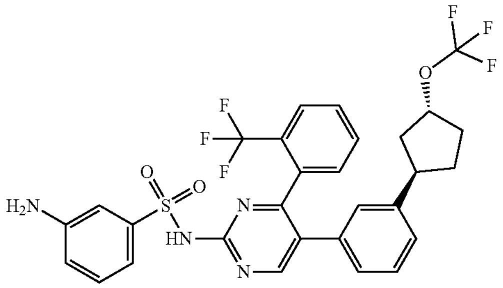 [SMILES: Nc1cccc(S(=O)(=O)Nc2ncc(-c3cccc([C@@H]4CC[C@@H](OC(F)(F)F)C4)c3)c(-c3ccccc3C(F)(F)F)n2)c1] |
| 21 | 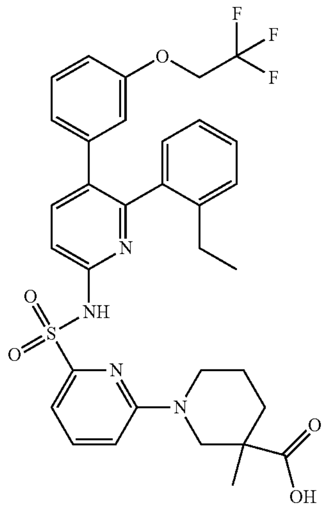 [SMILES: CCc1ccccc1-c1nc(NS(=O)(=O)c2cccc(N3CCCC(C)(C(=O)O)C3)n2)ccc1-c1cccc(OCC(F)(F)F)c1] |
| 15 | 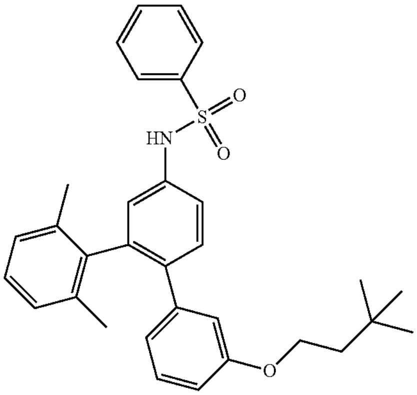 [SMILES: Cc1cccc(C)c1-c1cc(NS(=O)(=O)c2ccccc2)ccc1-c1cccc(OCCC(C)(C)C)c1] |

-continued
| # | Compound |
|---|---|
| 12 | 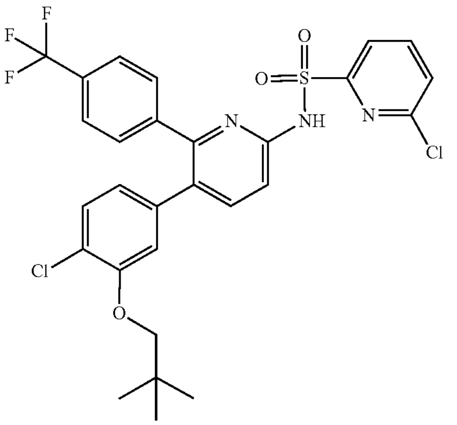 [SMILES: CC(C)(C)COc1cc(-c2ccc(NS(=O)(=O)c3cccc(Cl)n3)nc2-c2ccc(C(F)(F)F)cc2)ccc1Cl] |
| 6b | 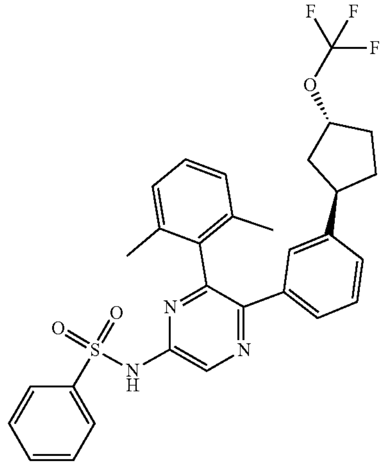 [SMILES: Cc1cccc(C)c1-c1nc(NS(=O)(=O)c2ccccc2)cnc1-c1cccc([C@@H]2CC[C@@H](OC(F)(F)F)C2)c1] |
| 16 | 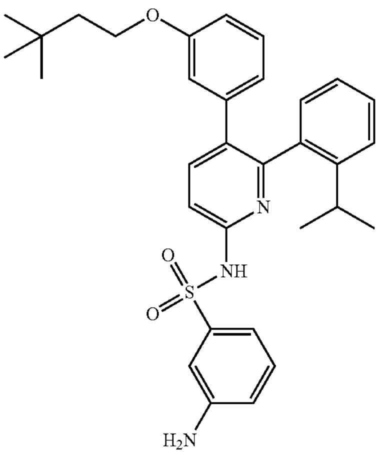 [SMILES: CC(C)c1ccccc1-c1nc(NS(=O)(=O)c2cccc(N)c2)ccc1-c1cccc(OCCC(C)(C)C)c1] |
-continued
| # | Compound |
|---|---|
| 4 | 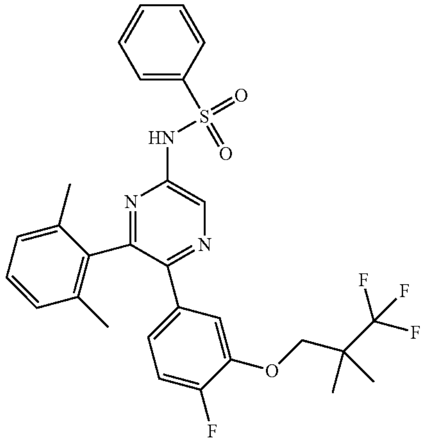 [SMILES: Cc1cccc(C)c1-c1nc(NS(=O)(=O)c2ccccc2)cnc1-c1ccc(F)c(OCC(C)(C)C(F)(F)F)c1] |
| 20 | 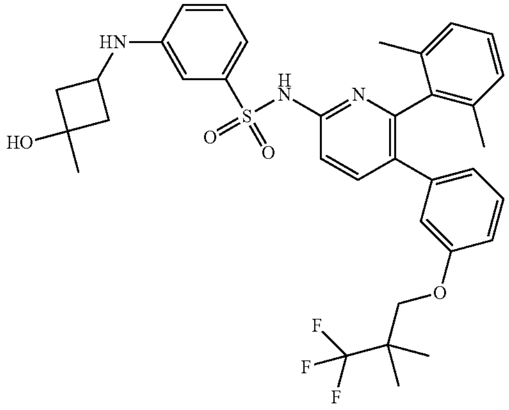 [SMILES: Cc1cccc(C)c1-c1nc(NS(=O)(=O)c2cccc(NC3CC(C)(O)C3)c2)ccc1-c1cccc(OCC(C)(C)C(F)(F)F)c1] |
| 10a | 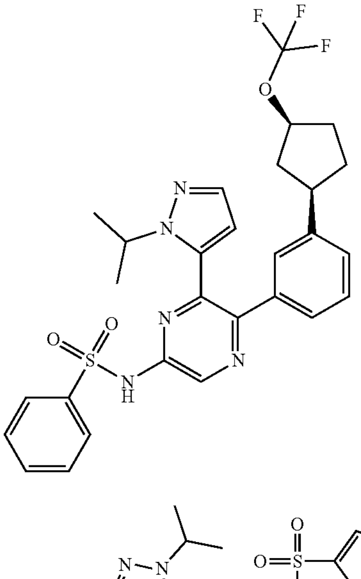 |
| 11 | 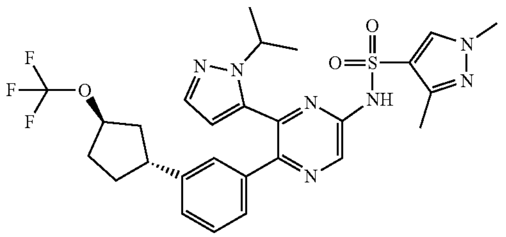 [SMILES: Cc1nn(C)cc1S(=O)(=O)Nc1cnc(-c2cccc([C@@H]3CC[C@@H](OC(F)(F)F)C3)c2)c(-c2ccnn2C(C)C)n1] |

-continued
| # | Compound |
|---|---|
| 23 | 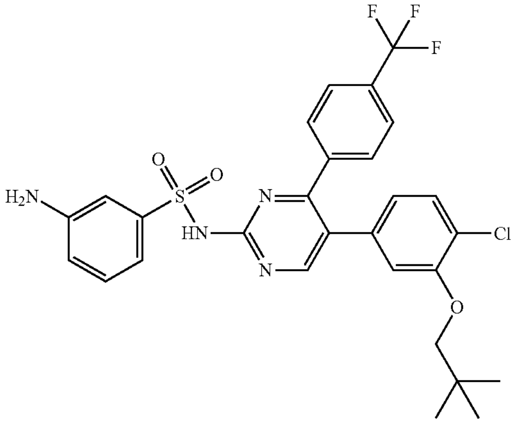 [SMILES: CC(C)(C)COc1cc(-c2cnc(NS(=O)(=O)c3cccc(N)c3)nc2-c2ccc(C(F)(F)F)cc2)ccc1Cl] |
| 3 | 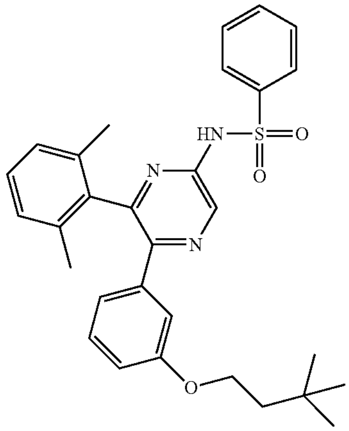 [SMILES: Cc1cccc(C)c1-c1nc(NS(=O)(=O)c2ccccc2)cnc1-c1cccc(OCCC(C)(C)C)c1] |
| 13 | 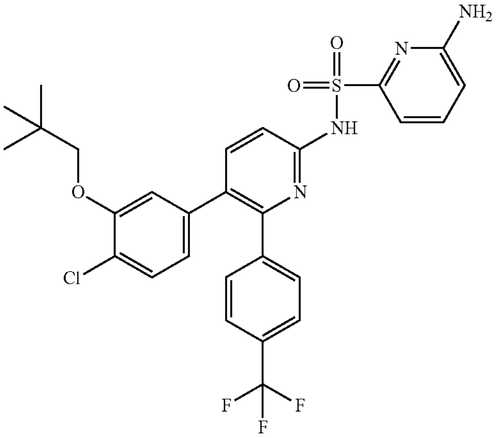 [SMILES: CC(C)(C)COc1cc(-c2ccc(NS(=O)(=O)c3cccc(N)n3)nc2-c2ccc(C(F)(F)F)cc2)ccc1Cl] |
-continued
| # | Compound |
|---|---|
| 10b | 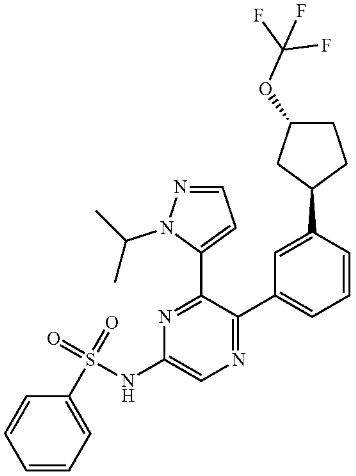 [SMILES: CC(C)n1nccc1-c1nc(NS(=O)(=O)c2ccccc2)cnc1-c1cccc([C@@H]2CC[C@@H](OC(F)(F)F)C2)c1] |
| 25 | 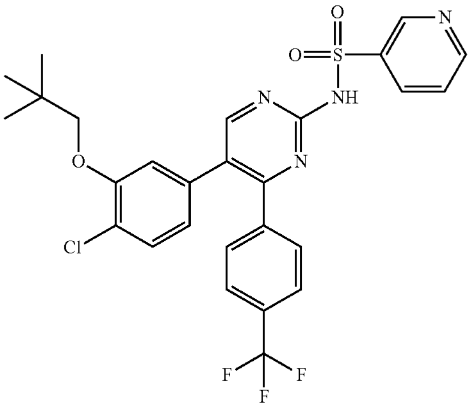 [SMILES: CC(C)(C)COc1cc(-c2cnc(NS(=O)(=O)c3cccnc3)nc2-c2ccc(C(F)(F)F)cc2)ccc1Cl] |
| 1 | 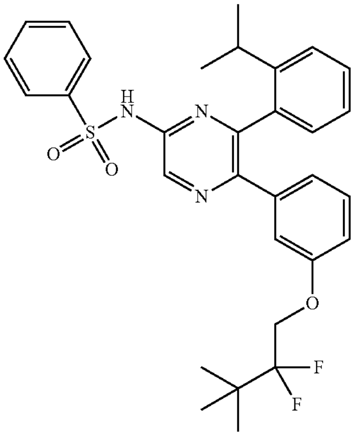 [SMILES: CC(C)c1ccccc1-c1nc(NS(=O)(=O)c2ccccc2)cnc1-c1cccc(OCC(F)(F)C(C)(C)C)c1] |

-continued

| # | Compound |
|---|---|
| 9a | 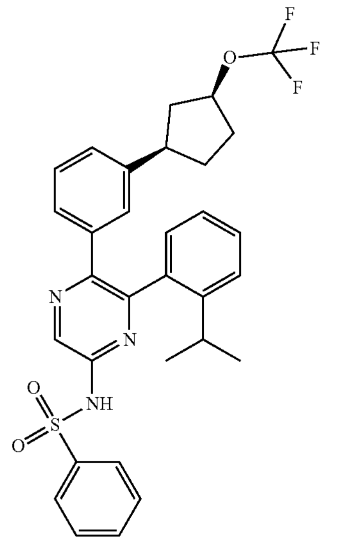 [SMILES: CC(C)c1ccccc1-c1nc(NS(=O)(=O)c2ccccc2)cnc1-c1cccc([C@@H]2CC[C@H](OC(F)(F)F)C2)c1] |
| 7b | 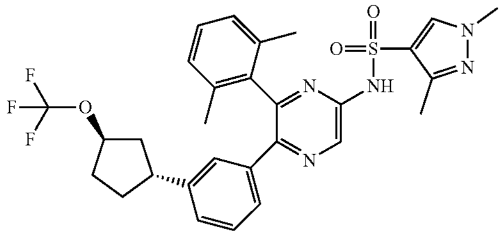 [SMILES: Cc1cccc(C)c1-c1nc(NS(=O)(=O)c2cn(C)nc2C)cnc1-c1cccc([C@@H]2CC[C@@H](OC(F)(F)F)C2)c1] |

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10, more preferably from 1-6. unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $-CF_3$, —CN and the like. Exemplary substituted alkyls are described below. Cycloalkyls can be further substituted with alkyls, alkenyls, alkoxys, alkylthios, aminoalkyls, carbonyl-substituted alkyls, $-CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc.

$C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "haloalkyl", as used herein, refers to an alkyl group in which at least one hydrogen has been replaced with a halogen, such as fluoro, chloro, bromo, or iodo. Exemplary haloalkyl groups include trifluoromethyl, difluoromethyl, fluoromethyl, 2-fluoroethyl, 2,2-difluoroethyl, and 2,2,2-trifluoroethyl.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

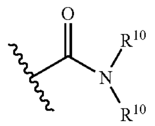

wherein each $R^{10}$ independently represents a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

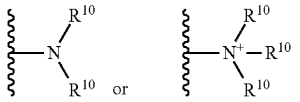

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

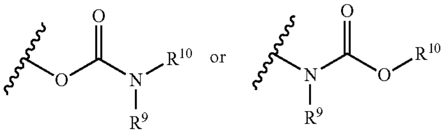

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings.

A "cycloalkenyl" group is a cyclic hydrocarbon containing one or more double bonds. The cycloalkenyl ring may have 3 to 10 carbon atoms. As such, cycloalkenyl groups can be monocyclic or multicyclic. Individual rings of such multicyclic cycloalkenyl groups can have different connectivities, e.g., fused, bridged, spiro, etc. in addition to covalent bond substitution. Exemplary cycloalkenyl groups include cyclopropenyl, cyclobutenyl, cyclopentyl, cyclohexenyl, cycloheptenyl, 1,3-cyclohexadienyl, 1,4-cyclohexadienyl and 1,5-cyclooctadienyl.

Exemplary cycloalkyl groups include cyclopropyl, cyclobutyl, cyclopentyl, cyclohexyl, norbornanyl, bicyclo[3.2.1]octanyl, octahydro-pentalenyl, spiro[4.5]decanyl, cyclopropyl, and adamantyl.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —C(O)$OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 3- to 10-membered rings, more preferably 5- to 9-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

Individual rings of such multicyclic heteroaryl groups can have different connectivities, e.g., fused, etc. in addition to covalent bond substitution. Exemplary heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. In general, the heteroaryl group typically is attached to the main structure via a carbon atom.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

Individual rings of such multicyclic heterocycloalkyl groups can have different connectivities, e.g., fused, bridged, spiro, etc. in addition to covalent bond substitution. Exemplary heterocycloalkyl groups include pyrrolidinyl, tetrahydrofuranyl, dihydrofuranyl, tetrahydropyranyl, pyranyl, thiopyranyl, azindinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl, octahydro-1H-indolyl, etc. In general, the heterocycloalkyl group typically is attached to the main structure via a carbon atom or a nitrogen atom.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

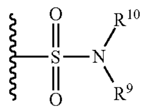

or

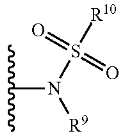

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

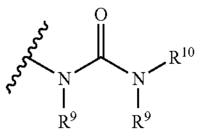

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light. In certain embodiments, compounds of the invention may be racemic.

In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The compounds of the invention may be prepared as individual isomers by either isomer specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least about 60%, about 70%, about 80%, about 90%, about 99% or about 99.9% by weight pure relative to the other stereoisomers. When a single enantiomer is named or depicted by structure, the depicted or named enantiomer is at least about 60%, about 70%, about 80%, about 90%, about 99% or about 99.9% by weight optically pure. Percent optical purity by weight is the ratio of the weight of the enantiomer that is present divided by the combined weight of the enantiomer that is present and the weight of its optical isomer.

In the pictorial representation of the compounds given through this application, a thickened tapered line () indicates a substituent which is above the plane of the ring to which the asymmetric carbon belongs and a dotted line () indicates a substituent which is below the plane of the ring to which the asymmetric carbon belongs.

As used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

An isotope-labelled form of a disclosed compound has one or more atoms of the compound replaced by an atom or atoms having an atomic mass or mass number different that that which usually occurs in greater natural abundance. Examples of isotopes which are readily commercially available and which can be incorporated into a disclosed compound by well-known methods include isotopes of hydrogen, carbon, nitrogen, oxygen, phosphorus, fluorine and chlorine, for example, 2H, 3H, 13C, 14C, 15N, 18O, 17O, 31P, 32P, 35S, 18F and 36Cl, respectively. An isotope-labelled compound provided herein can usually be prepared by carrying out the procedures disclosed herein, replacing a non-isotope-labelled reactant by an isotope-labelled reactant.

The concentration of such a heavier isotope, specifically deuterium, may be defined by the isotopic enrichment factor. The term "isotopic enrichment factor" as used herein means the ratio between the isotopic abundance and the natural abundance of a specified isotope. If a hydrogen atom in a compound of this invention is replaced with deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

An isotope-labelled compound as provided herein can be used in a number of beneficial ways. Compounds having 14C incorporated are suitable for medicament and/or substrate tissue distribution assays. Tritium (3H) and carbon-14 (14C), are preferred isotopes owing to simple preparation and excellent detectability. Heavier isotopes, for example deuterium (2H), has therapeutic advantages owing to the higher metabolic stability. Metabolism is affected by the primary kinetic isotope effect, in which the heavier isotope has a lower ground state energy and causes a reduction in the rate-limiting bond breakage. Slowing the metabolism can lead to an increased in vivo half-life or reduced dosage requirements or an improvement in therapeutic index.

For a further discussion, see S. L. Harbeson and R. D. Tung, Deuterium In Drug Discovery and Development, Ann. Rep. Med. Chem. 2011, 46, 403-417, Foster, A. B., "Deuterium Isotope Effects in Studies of Drug Metabolism," Trends in Pharmacological Sciences, 5: 524-527 (1984) AND Foster, A. B., "Deuterium Isotope Effects in the Metabolism of Drugs and Xenobiotics: Implications for Drug Design," Advances in Drug Research, 14: 1-40 (1985).

Metabolic stability can be affected by the compound's processing in different organs of the body. For example, compounds with poor pharmacokinetic profiles are susceptible to oxidative metabolism. In vitro liver microsomal assays currently available provide valuable information on the course of oxidative metabolism of this type, which in turn assists in the rational design of deuterated compounds as disclosed herein. Improvements can be measured in a number of assays known in the art, such as increases in the in vivo half-life (t1/2), concentration at maximum therapeutic effect (Cmax), area under the dose response curve (AUC), and bioavailability; and in terms of reduced clearance, dose and materials costs.

Another effect of deuterated compounds can be diminishing or eliminating undesired toxic metabolites. For example, if a toxic metabolite arises through oxidative carbon-hydrogen (C—H) bond cleavage, the deuterated analogue will have a slower reaction time and slow the production of the unwanted metabolite, even if the particular oxidation is not a rate-determining step. See, e.g., Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" means to decrease, suppress, attenuate, diminish, arrest, or stabilize the development or progression of a disease (e.g., a disease or disorder delineated herein), lessen the severity of the disease or improve the symptoms associated with the disease. Treatment includes treating a symptom of a disease, disorder or condition. Without being bound by any theory, in some embodiments, treating includes augmenting deficient CFTR activity. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the term "prodrug" means a pharmacological derivative of a parent drug molecule that requires biotransformation, either spontaneous or enzymatic, within the organism to release the active drug. For example, prodrugs are variations or derivatives of the compounds of the invention that have groups cleavable under certain metabolic conditions, which when cleaved, become the compounds of the invention. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, CA, 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability.

As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrullinehomocysteine, homoserine, ornithine and methionine sulfone. Prodrugs also include compounds having a carbonate, carbamate, amide or alkyl ester moiety covalently bonded to any of the above substituents disclosed herein.

A "therapeutically effective amount", as used herein refers to an amount that is sufficient to achieve a desired therapeutic effect. For example, a therapeutically effective amount can refer to an amount that is sufficient to improve at least one sign or symptom of cystic fibrosis.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

As used herein, "CFTR" means cystic fibrosis transmembrane conductance regulator. Loss of function mutations of CFTR are a cause of cystic fibrosis and lead to exocrine gland dysfunction and abnormal mucociliary clearance. Mutations in the CFTR gene or protein may result in reduced activity of CFTR. The most common mutation is a specific mutation of the deletion of three nucleotides of the codon for phenylalanine at position 508 (about 70% of cystic fibrosis patients) referred to as "ΔF508". The ΔF508 mutation decreases the stability of the CFTR NBD1 domain and limits CFTR interdomain assembly. A patient can be ΔF508 homozygous or ΔF508 heterozygous (ΔF508/ΔF508). Particular mutations result in a CFTR gating defect such that the probability that the CFTR ion channel attains its open conformation is reduced. Such mutations include but are not limited to G551D, G178R, S549N, S549R, G551S, G970R, G1244E, S1251N, S1255P, and G1349D.

As used herein, the term "CFTR modulator" refers to a compound that increases the activity of CFTR. In certain aspects, a CFTR modulator is a CFTR corrector or a CFTR potentiator or a dual-acting compound having activities of a corrector and a potentiator. These dual acting agents are useful when the mutations result in absence or reduced amount of synthesized CFTR protein.

As used herein, the term "CFTR corrector" refers to a compound that increases the amount of functional CFTR protein at the cell surface, thus enhancing ion transport through CFTR. CFTR correctors partially "rescue" misfolding of CFTR protein, particularly such misfolding that results from CFTR mutations, thereby permitting CFTR protein maturation and functional expression on the cell surface. CFTR correctors may modify the folding environment of the cell in a way that promotes CFTR folding, and include compounds that interact directly with CFTR protein to modify its folding, conformational maturation or stability. Examples of correctors include, but are not limited to, VX-809, VX-661, VX-152, VX-440, VX-445, VX-659, VX-121, compounds described in US20190248809A1, VX-983, GLPG2222, GLPG2737, GLPG3221, GLPG2851, FDL169, FDL304, FDL2052160, FD2035659, and PTI-801.

As used herein, the term "CFTR potentiator" refers to a compound that increases the ion channel activity of CFTR protein located at the cell surface, resulting in enhanced ion transport. CFTR potentiators restore the defective channel function that results from CFTR mutations, or that otherwise increase the activity of CFTR at the cell surface. Examples of potentiators include, but are not limited to, ivacaftor (VX770), deuterated ivacaftor (CPT 656, VX-561), PTI-808, QBW251, GLPG1837, GLPG2451, ABBV-3067, ABBV-974, ABBV-191, FDL176, and genistein.

As used herein, "CFTR disease or condition" refers to a disease or condition associated with deficient CFTR activity, for example, cystic fibrosis, congenital bilateral absence of vas deferens (CBAVD), acute, recurrent, or chronic pancreatitis, pancreatic steatorrhea, disseminated bronchiectasis, asthma, allergic pulmonary aspergillosis, chronic obstructive pulmonary disease (COPD), rhinosiniusitis, nasal podyposis, dry eye disease, protein C deficiency, abetalipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, congenital pneumonia, nontuberculous mycobacterial infection, constipation, pancreatic insufficiency, celiac disease, intestinal atresia, hereditary emphysema, and Sjogren's syndrome.

Methods of Use

Disclosed herein are methods of treating deficient CFTR activity in a cell, comprising contacting the cell with a compound of formula (I), or a pharmaceutically acceptable salt thereof. In certain embodiments, contacting the cell occurs in a subject in need thereof, thereby treating a disease or disorder mediated by deficient CFTR activity.

Also, disclosed herein are methods of treating a disease or a disorder mediated by deficient CFTR activity comprising administering a compound of Formula (I) or a pharmaceutically acceptable salt thereof. In some embodiments, the subject is a mammal, preferably a human. In some embodiments, the disease is associated with the regulation of fluid volumes across epithelial membranes, particularly an obstructive airway disease such as CF or COPD.

Such diseases and conditions include, but are not limited to, cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, protein C deficiency, celiac disease, nasal polyposis, congenital pneumonia, intestinal malabsorption, pancreatic steatorrhea, intestinal atresia, non-tuberculous mycobacterial infection, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear plasy, Pick's disease, several polyglutamine neurological disorders, Huntington's, spinocerebullar ataxia type I, spinal and bulbar muscular atrophy, dentatorubal pallidoluysian, myotonic dystrophy, spongiform encephalopathies, hereditary Creutzfeldt-Jakob disease, Fabry disease, Straussler-Scheinker syndrome, COPD, dry-eye disease, Sjogren's disease, Osteoporosis, Osteopenia, bone healing and bone growth, bone repair, bone regeneration, reducing bone resorption, increasing bone deposition, Gorham's Syndrome, chloride channelopathies, myotonia congenita, Bartter's syndrome type III, Dent's disease, hyperekplexia, epilepsy, hyperekplexia, lysosomal storage disease, Angelman syndrome, Primary Ciliary Dyskinesia (PCD), PCD with situs inversus, PCD without situs inversus and ciliary aplasia.

Such diseases and conditions include, but are not limited to, cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic sinusitis, dry eye disease, protein C deficiency, Abetalipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome. In some embodiments, the disease is cystic fibrosis.

Provided herein are methods of treating cystic fibrosis, comprising administering to a subject in need thereof, a compound as disclosed herein or a pharmaceutically acceptable salt thereof. Also provided herein are methods of lessening the severity of cystic fibrosis, comprising administering to a subject in need thereof, a compound as disclosed herein or a pharmaceutically acceptable salt thereof. In some embodiments, the subject is a human. In some embodiments, the subject is at risk of developing cystic fibrosis, and administration is carried out prior to the onset of symptoms of cystic fibrosis in the subject.

Provided herein are compounds as disclosed herein for use in treating a disease or condition mediated by deficient CFTR activity. Also provided herein are uses of a compound as disclosed herein for the manufacture of a medicament for treating a disease or condition mediated by deficient CFTR activity.

The compounds and methods described herein can be used to treat subjects who have deficient CFTR activity and harbor CFTR mutations like ΔF508. The ΔF508 mutation impedes normal CFTR folding, stability, trafficking, and function by decreasing the stability of CFTR's NBD1 domain, the competency of CFTR domain-domain assembly, or both. Due their impact on the ICL4 interface, a CFTR corrector with an ICL4-directed mechanism can be effective in subjects harboring the following mutations: ΔF508-CFTR (>70% of all CF patients harbor at least one copy) and mutations that cause ICL4 interface instability for example: G85E, H139R, H1054D, L1065P, L1077P, R1066C and other CFTR mutations where ICL4 interface stability is compromised.

Provided herein are kits for use in measuring the activity of CFTR or a fragment thereof in a biological sample in vitro or in vivo. The kit can contain: (i) a compound as disclosed herein, or a pharmaceutical composition comprising the disclosed compound, and (ii) instructions for: a) contacting the compound or composition with the biological sample; and b) measuring activity of said CFTR or a fragment thereof. In some embodiments, the biological sample is biopsied material obtained from a mammal or extracts thereof; blood, saliva, urine, feces, semen, tears, other body fluids, or extracts thereof. In some embodiments, the mammal is a human.

Combination Treatments

As used herein, the term "combination therapy" means administering to a subject (e.g., human) two or more CFTR modulators, or a CFTR modulator and an agent such as antibiotics, ENaC inhibitors, GSNO (S-nitrosothiol s-nitroglutanthione) reductase inhibitors, and a CRISPR C as correction therapy or system (as described in US 2007/0022507 and the like).

In certain embodiments, the method of treating or preventing a disease or condition mediated by deficient CFTR activity comprises administering a compound as disclosed herein conjointly with one or more other therapeutic agent (s). In some embodiments, one other therapeutic agent is administered. In other embodiments, at least two other therapeutic agents are administered.

Additional therapeutic agents include, for example, ENaC inhibitors, mucolytic agents, bronchodilators, antibiotics, anti-infective agents, anti-inflammatory agents, ion channel modulating agents, therapeutic agents used in gene therapy, agents that reduce airway surface liquid and/or reduce airway surface pH, CFTR correctors, and CFTR potentiators, or other agents that modulate CFTR activity.

In some embodiments, at least one additional therapeutic agent is selected from one or more CFTR modulators, one or more CFTR correctors and one or more CFTR potentiators.

Non-limiting examples of additional CFTR modulators, correctors and potentiators include VX-770 (Ivacaftor), VX-809 (Lumacaftor, 3-(6-(I-(2,2-5 difluorobenzo[d][1, 3]dioxol-5-yl)cyclopropanecarboxamido)-3-methylpyridin-2-yl) benzoic acid, VX-661 (Tezacaftor, I-(2,2-difluoro-1, 3-benzodioxol-5-yl)-N—[I-[(2R)-2,3-dihydroxypropyl]-6-fluoro-2-(2-hydroxy-1, I-dimethylethyl)-1H-indol-5-yl]-cyclopropanecarboxamide), VX-983, VX-152, VX-440, VX-445, VX-659, VX-371, VX-121, Orkambi, compounds described in US20190248809A1, Ataluren (PTC 124) (3-[5-(2-fluorophenyl)-1, 2,4-oxadiazol-3-yl]benzoic acid), PTI-130 (Proteostasis), PTI-801, PTI-808, PTI-428, N91115.74 (cavosonstat), QBW251 (Novartis) compounds described in WO2011113894, compounds N30 Pharmaceuticals (e.g., WO 2014/186704), deuterated ivacaftor (e.g., CTP-656 or VX-561), GLPG2222, GLPG3221, GLPG2451, GLPG3067, GLPG2851, GLPG2737, GLPG1837 (N-(3-carbamoyl-5,5,7,7-tetramethyl-5,7-dihydro-4H-thieno[2,3-c]pyran-2-yl)-1H-pyrazole-5-carboxamide), GLPG2665 (Galapagos), ABBV-191 (Abbvie), ABBV-974, FDL 169 (Flatley Discovery lab), FDL 176, FDL438, FDL304, FD2052160, FD1881042, FD2027304, FD2035659, FD2033129, FD1860293, CFFT-Pot01, CFFT-Pot-02, P-1037, glycerol, phenylbutyrate, and the like.

Non-limiting examples of anti-inflammatory agents are N6022 (3-(5-(4-(1H-imidazol-1-yl)10 phenyl)-1-(4-carbamoyl-2-methylphenyl)-$^1$H-pyrrol-2-yl) propanoic acid), Ibuprofen, Lenabasum (anabasum), Acebilustat (CTX-4430), LAU-7b, POL6014, docosahexaenoic acid, alpha-1 antitrypsin, sildenafil. Additional therapeutic agents also include, but are not limited to a mucolytic agent, a modifier of mucus rheology (such as hypertonic saline, mannitol, and oligosaccharide based therapy), a bronchodilator, an anti-infective (such as tazobactam, piperacillin, rifampin, meropenum, ceftazidime, aztreonam, tobramycin, fosfomycin, azithromycin, vancomycin, gallium and colistin), an anti-infective agent, an anti-inflammatory agent, a CFTR modulator other than a compound of the present invention, and a nutritional agent. Additional therapeutic agents can include treatments for comorbid conditions of cystic fibrosis, such as exocrine pancreatic insufficiency which can be treated with Pancrelipase or Liprotamase.

Examples of CFTR potentiators include, but are not limited to, Ivacaftor (VX-770), CTP-656, NVS-QBW251, PTI-808, ABBV-3067, ABBV-974, ABBV-191, FDL176, FD1860293, GLPG2451, GLPG1837, and N-(3-carbamoyl-5,5,7,7-tetramethyl-5,7-dihydro-4H-thieno[2,3-c]pyran-2-yl)-1H-pyrazole-5-carboxamide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, and U.S. patent application Ser. Nos. 14/271,080, 14/451,619 and 15/164,317.

[135][134] Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropane carboxamide (VX-661), VX-983, GLPG2222, GLPG2665, GLPG2737, GLPG3221, GLPG2851, VX-152, VX-440, VX-121, VX-445, VX-659, compounds described in US20190248809A1, PTI-801, FDL169, FDL304, FD2052160, and FD2035659. Examples of correctors are also disclosed in US20160095858A1, and U.S. application Ser. Nos. 14/925,649 and 14/926,727.

In certain embodiments, the additional therapeutic agent is a CFTR amplifier. CFTR amplifiers enhance the effect of known CFTR modulators, such as potentiators and correctors. Examples of CFTR amplifier include PTI130 and PTI-428. Examples of amplifiers are also disclosed in publications: WO2015138909 and WO2015138934.

In certain embodiments, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, ETD001, Aerolytic, amiloride, AZD5634, and VX-371. Additional agents that reduce the activity of the epithelial sodium channel blocker (ENaC) can be found, for example, in PCT Publication No. WO2009074575 and WO2013043720; and U.S. Pat. No. 8,999,976.

In one embodiment, the ENaC inhibitor is VX-371. In one embodiment, the ENaC inhibitor is SPX-101 (S18).

In certain embodiments, the additional therapeutic agent is an agent that modulates the activity of the non-CFTR Cl-channel TMEM16A. Non-limiting examples of such agents include TMEM16A activators, denufosol, Melittin, Cinnamaldehyde, 3,4,5-Trimethoxy-N-(2-methoxyethyl)-N-(4-phenyl-2-thiazolyl)benzamide, INO-4995, CLCA1, ETX001, ETDO02 and phosphatidylinositol diC8-PIP2, and TMEM16A inhibitors, 10 bm, Arctigenin, dehydroandrographolide, Ani9, Niclosamide, and benzbromarone.

In certain embodiments, the combination of a compound of Formula (I), with a second therapeutic agent may have a synergistic effect in the treatment of cancer and other diseases or disorders mediated by adenosine. In other embodiments, the combination may have an additive effect.

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, the dosing follows a 3+3 design. The traditional 3+3 design requires no modeling of the dose-toxicity curve beyond the classical assumption for cytotoxic drugs that toxicity increases with dose. This rule-based design proceeds with cohorts of three patients; the first cohort is treated at a starting dose that is considered to be safe based on extrapolation from animal toxicological data, and the subsequent cohorts are treated at increasing dose levels that have been fixed in advance. In some embodiments, the three doses of a compound of formula (I) range from about 100 mg to about 1000 mg orally, such as about 200 mg to about 800 mg, such as about 400 mg to about 700 mg, such as about 100 mg to about 400 mg, such as about 500 mg to about 1000 mg, and further such as about 500 mg to about 600 mg. Dosing can be three times a day when taken with without food, or twice a day when taken with food. In certain embodiments, the three doses of a compound of formula (I) range from about 400 mg to about 800 mg, such as about 400 mg to about 700 mg, such as about 500 mg to about 800 mg, and further such as about 500 mg to about 600 mg twice a day. In certain preferred embodiments, a dose of greater than about 600 mg is dosed twice a day.

If none of the three patients in a cohort experiences a dose-limiting toxicity, another three patients will be treated at the next higher dose level. However, if one of the first three patients experiences a dose-limiting toxicity, three more patients will be treated at the same dose level. The dose escalation continues until at least two patients among a cohort of three to six patients experience dose-limiting toxicities (i.e., ≥about 33% of patients with a dose-limiting toxicity at that dose level). The recommended dose for phase II trials is conventionally defined as the dose level just below this toxic dose level.

In certain embodiments, the dosing schedule can be about 40 $mg/m^2$ to about 100 $mg/m^2$, such as about 50 $mg/m^2$ to about 80 $mg/m^2$, and further such as about 70 $mg/m^2$ to about 90 $mg/m^2$ by IV for 3 weeks of a 4 week cycle.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, parabromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

A number of synthetic protocols were used to produce the compounds described herein. These synthetic protocols (see schemes below) have common intersections and can be used alternatively for synthesis of the compounds described herein.

EXAMPLES

General Schemes

The compound of Formula (I) can be synthesized according to one of the schemes 1-3 based on the nature of the $X^1$, $X^2$, and $X^3$, the substituents, and the availability of the starting materials.

(I)

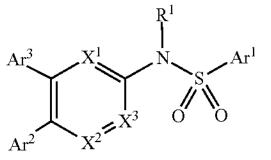

Scheme 1

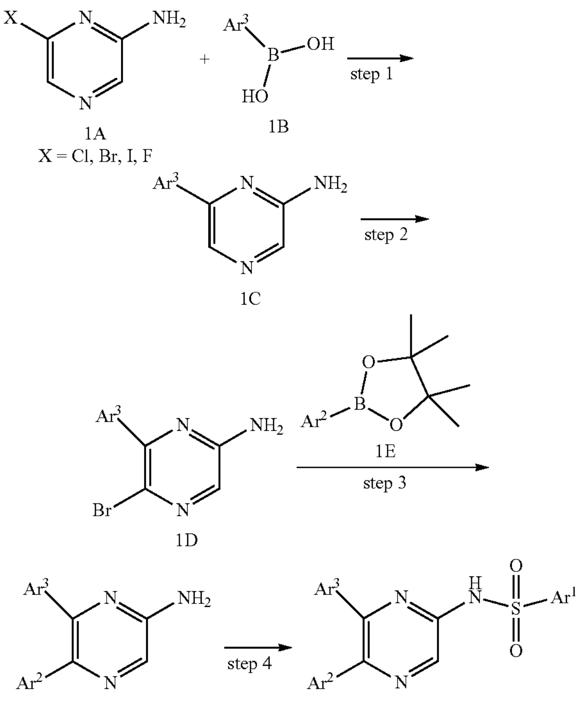

1A

X = Cl, Br, I, F

1B

1C

1D

1E

1F (I)

Scheme 1 illustrates the synthesis of the compound of formula (I). In step 1, 6-halogen-pyrazin-2-amine 1A is condensed with aryl boronic acid 1B, with the proper substituents attached, to give 6-aryl pyrazin-2-amine 1C under the standard Suzuki coupling conditions known to the art in the field. The bromination in step 2 selectively goes to position 5 under the given conditions (see examples). The second Suzuki coupling (step 3) of 1D with the properly substituted aryl boronic acid 1E to give 1F. Sulfonamide formation (step 4) then carried out with aryl sulfonyl chloride catalyzed with a base, such as triethylamine, to provide compound of formula (I).

Scheme 2

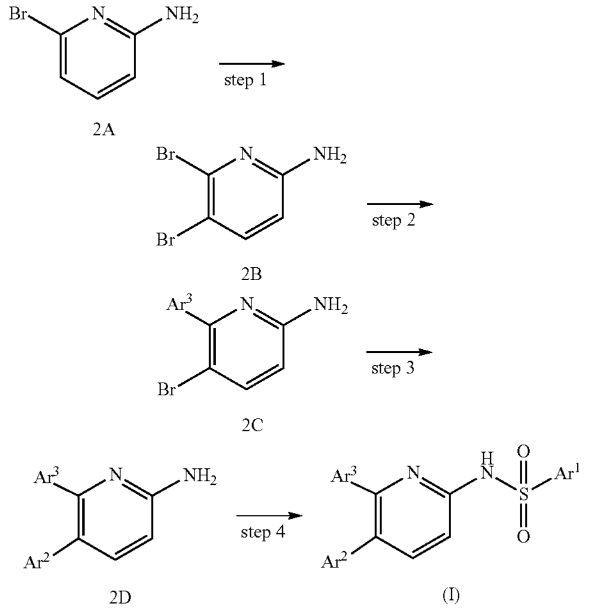

Scheme 2 illustrates the synthesis of the compounds of formula (I) where $X^1$ is nitrogen, $X^2$ and $X^3$ is carbon. Starting material 2A is brominated to obtain 2B (Step 1). In step 2, 6-bromo is selectively replaced by aryl $Ar^3$ via a Suzuki coupling reaction or similar protocol to obtain 2C. The second aryl is installed (step 3) next, again via a Suzuki or similar coupling reaction to give 2D. The final compound of formula (I) can be synthesized through sulfonamide formation (step 4).

Scheme 3

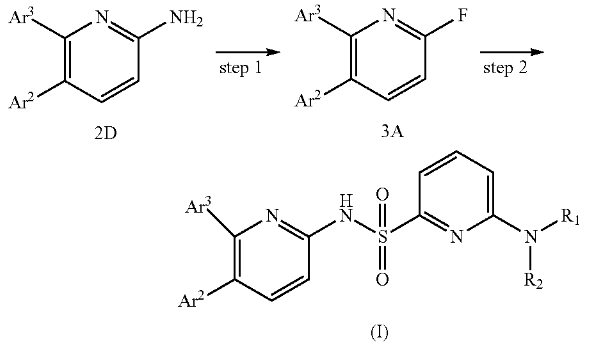

Alternatively, the amino group in 2D can be converted into fluoride 3A by treating with $NaNO_2$ in HF (step 1). The fluoride atom can serve as leaving group to achieve the nucleophilic substitution reaction to afford the compound of formula (I).

Scheme 4

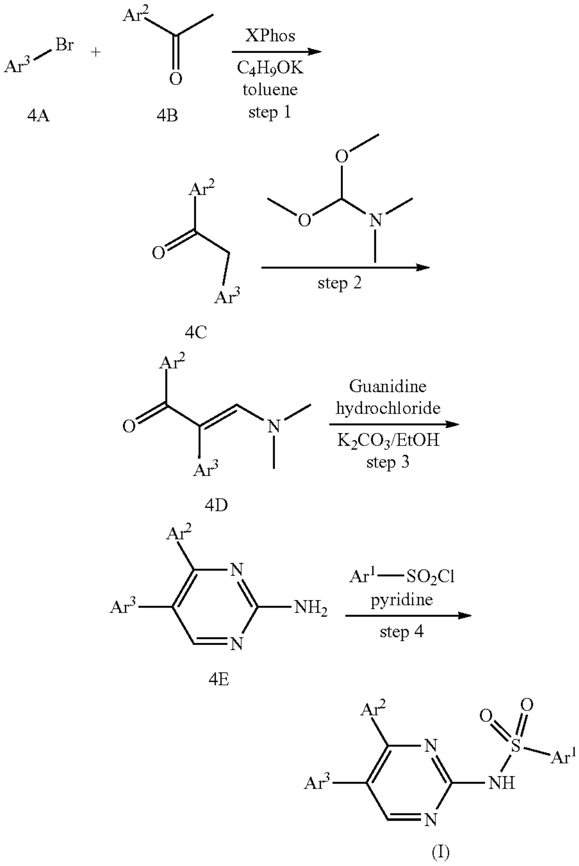

In this synthetic sequence, aryl bromide 4A is coupled with aryl methyl ketone 4B under the catalytic conditions at elevated temperature to obtain 4C. The ketone 4C is condensed with 1,1-dimethoxy-N,N-dimethylmethanamine to form 4D. The intermediate 4D is cyclized with guanidine hydrochloride catalyzed by a base, such as potassium carbonate in protonic solvent, such as ethanol, with heating to give 4E. Standard aryl sulfonamide formation conditions give the expected compound of Formula (I).

Analytical Methods

The 1H NMR spectra are run at 400 MHz on a Gemini 400 or Varian Mercury 400 spectrometer with an ASW 5 mm probe, and usually recorded at ambient temperature in a deuterated solvent, such as D2O, DMSO-D6 or CDCl3 unless otherwise noted. Chemical shifts values (6) are indicated in parts per million (ppm) with reference to tetramethylsilane (TMS) as the internal standard.

High Pressure Liquid Chromatography-Mass Spectrometry (LCMS) experiments to determine retention times (RT) and associated mass ions were performed using one of the following methods.

Mass Spectra (MS) were recorded using a Micromass mass spectrometer. Generally, the method used was positive electro-spray ionization, scanning mass m/z from 100 to 1000. Liquid chromatography was performed on a Hewlett Packard 1100 Series Binary Pump & Degasser; Auxiliary detectors used were: Hewlett Packard 1100 Series UV detector, wavelength=220 nm and Sedere SEDEX 75

Evaporative Light Scattering (ELS) detector temperature=46° C., N2 pressure=4 bar.

LCT: Grad (AcN+0.05% TFA):($H_2O$+0.05% TFA)=5:95 (0 min) to 95:5 (2.5 min) to 95:5 (3 min). Column: YMC Jsphere 33x2 4 μM, 1 ml/min MUX: Column: YMC Jsphere 33x2, 1 ml/min Grad (AcN+0.05% TFA):($H_2O$+0.05% TFA)=5:95 (0 min) to 95:5 (3.4 min) to 95:5 (4.4 min).

LCT2: YMC Jsphere 33x2 4 μM, (AcN+0.05% TFA):($H_2O$+0.05% TFA)=5:95 (0 min) to 95:5 (3.4 min) to 95:5 (4.4 min).

QU: YMC Jsphere 33x2 1 ml/min, (AcN+0.08% formic acid):($H_2O$+0.1% formic acid)=5:95 (0 min) to 95:5 (2.5 min) to 95:5 (3.0 min).

SYNTHESIS OF INTERMEDIATES

This section illustrates the synthesis of exemplary common intermediates used in the preparation of the example compounds. The procedures shown here are only illustrative and do not limit or restrict the methods that can be used for the synthesis of the examples.

Intermediate A 4,4,5,5-Tetramethyl-2-(3-(3,3,3-trifluoro-2,2-dimethylpropoxy)phenyl)-1,3,2-dioxaborolane

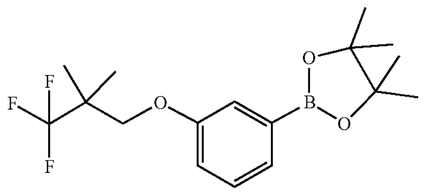 [SMILES: CC(C)(COc1cccc(B2OC(C)(C)C(C)(C)O2)c1)C(F)(F)F]

Step 1

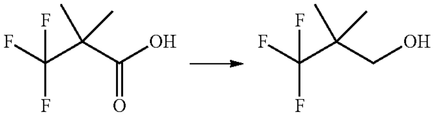

The solution of 3,3,3-trifluoro-2,2-dimethylpropanoic acid (10.0 g, 64.1 mmol) in $Et_2O$ (150 mL) was cooled to 0° C. $LiAlH_4$ (4.87 g, 128 mmol) was added. The mixture was stirred at room temperature overnight. When the reaction was completed, the reaction was quenched with $H_2O$ (5 mL), NaOH (15%, 5 mL) and $H_2O$ (15 mL). The mixture filtered through a Celite pad. The filtrate was concentrated to give 3,3,3-trifluoro-2,2-dimethylpropan-1-ol (8.4 g, 92.3%) as a yellow oil.

Step 2

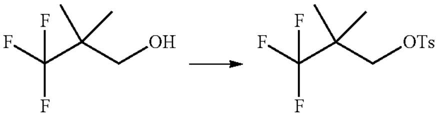

To a solution of 3,3,3-trifluoro-2,2-dimethylpropan-1-ol (8.4 g, 59.1 mmol) in $Et_2O$ (100 mL) was added NaOH (4.73 g, 118 mmol), followed by 4-methylbenzenesulfonyl chloride (12.4 g, 65.0 mmol). The result mixture was stirred at temperature overnight. The two layers were separated and the organic layer was washed with water (120 mLx3), $NaHCO_3$ (50 mL). Concentrated in vacuo and purified by flash column chromatography using PE:EA (5:1) as eluent to give 3,3,3-trifluoro-2,2-dimethylpropyl 4-methylbenzenesulfonate (12.6 g, Y: 71.9%) as yellow oil.

LCMS (acidic): LC retention time 2.130 min. MS (ESI) m/z 297 $[M+H]^+$.

Step 3

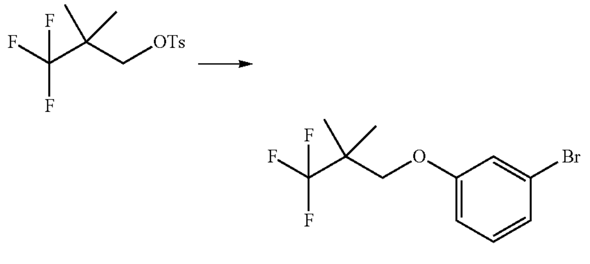

To a solution of 3,3,3-trifluoro-2,2-dimethylpropyl 4-methylbenzenesulfonate (6.0 g, 20.2 mmol) in DMSO (60 mL) was added 3-bromophenol (3.50 g, 20.2 mmol), $Cs_2CO_3$ (19.8 g, 60.7 mmol). The mixture was heated with stirring at 130° C. overnight. When the reaction completed, the mixture was diluted with EA (100 mL), washed with $H_2O$ (100 mLx3). The mixture concentrated in vacuo and purified by flash column chromatography using PE as eluent to give 1-bromo-3-(3,3,3-trifluoro-2,2-dimethylpropoxy)benzene (4.20 g, 69.8%) as a yellow oil.

LCMS (acidic): LC retention time 2.337 min. MS (ESI) m/z: No m/z observed.

Step 4

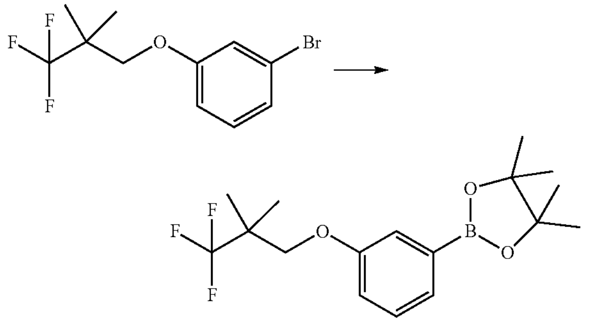

The reaction mixture of 1-bromo-3-(3,3,3-trifluoro-2,2-dimethylpropoxy)benzene (4 g, 13.5 mmol), bis(pinacolato)diboron (5.13 g, 20.2 mmol), $CH_3COOK$ (3.30 g, 33.7 mmol), Pd (dppf)$Cl_2$ (985 mg, 1.35 mmol) in 1,4-dioxane (50 mL) was heated at 80° C. under argon overnight. The reaction mixture was concentrated and purified by SGC (PE:EA=10:1) to give 4,4,5,5-tetramethyl-2-(3-(3,3,3-trifluoro-2,2-dimethylpropoxy)phenyl)-1,3,2-dioxaborolane (2.93 g, Yield: 63.2%) as a yellow oil.

LCMS (acidic): LC retention time 2.539 min. MS (ESI) m/z 345 $[M+H]^+$.

Intermediate B 2-(3-(2,2-Difluoro-3,3-dimethylbutoxy)phenyl)-4,4,5,5-tetramethyl-1,3,2-dioxaborolane

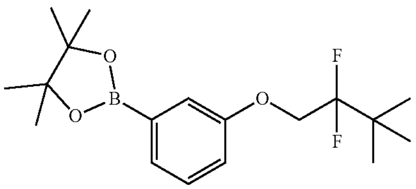 [SMILES: CC(C)(C)C(F)(F)COc1cccc(B2OC(C)(C)C(C)(C)O2)c1]

Step 1

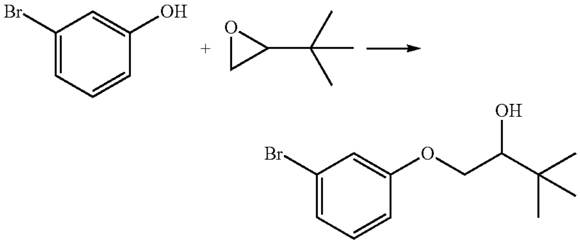

To the solution of 3-bromophenol (1.9 g, 11.0 mmol) in N,N-dimethylformamide (20 mL) was added 2-(tert-butyl) oxirane (1.65 g, 16.5 mmol) and cesium carbonate (7.16 g, 22.0 mmol) at room temperature. The resulting mixture was stirred at 80° C. overnight. The mixture was cooled to room temperature, diluted with water (150 mL), extracted with ethyl acetate (40 mL×3), washed with brine (60 mL), dried over anhydrous sodium sulfate, filtered and concentrated under reduced pressure, the residue was purified by silica gel column (9% ethyl acetate in petroleum ether) to give 1-(3-bromophenoxy)-3,3-dimethylbutan-2-ol as colorless oil (2.46 g, 82% yield).

LCMS: LC retention time 2.24 min. MS (ESI) m/z 275 $[M+H]^+$ $^{1}$HNMR (400 MHz, chloroform-d) δ 7.17-7.06 (m, 3H), 6.87-6.84 (m, 1H), 4.10-4.07 (m, 1 H), 3.85 (t, J=9.2 Hz, 1H) 3.69-3.66 (m, 1H), 2.36 (d, J=3.2 Hz, 1H), 1.01 (s, 9H).

Step 2

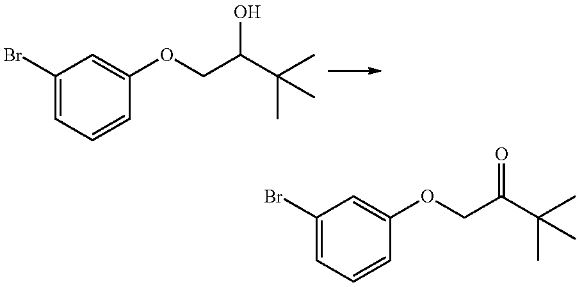

(1,1-diacetoxy-3-oxo-1λ5,2-benziodoxol-1-yl) acetate (5.73 g, 13.5 mmol) was added to the solution of 1-(3-bromophenoxy)-3,3-dimethylbutan-2-ol (2.46 g, 9.01 mmol) in dichloromethane (30 mL) at room temperature, the resulting reaction mixture was stirred at room temperature for 18 h. The solvent was removed under reduced pressure, and the residue was purified by silica gel column (10% ethyl acetate in petroleum ether) to give 1-(3-bromophenoxy)-3,3-dimethylbutan-2-one as colorless oil (2.18 g, 89% yield).

LCMS: LC retention time 2.18 min. MS (ESI) m/z 273 $[M+H]^+$ $^{1}$HNMR (400 MHz, chloroform-d) δ 7.16-7.10 (m, 2H), 7.02 (s, 1H), 6.81 (d, J=7.2 Hz, 1H), 4.85 (s, 2H), 1.25 (s, 9H).

Step 3

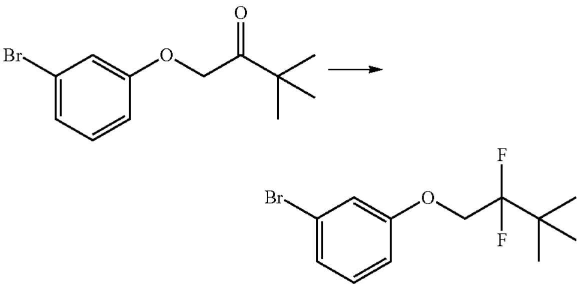

N-ethyl-N-(trifluoro-λ4-sulfanyl)ethanamine (5.18 g, 32.2 mmol) was added dropwise to the solution of 1-(3-bromophenoxy)-3,3-dimethylbutan-2-one (2.18 g, 8.04 mmol) in anhydrous dichloromethane (20 mL) at 0° C. under argon atmosphere, the resulting mixture was stirred at room temperature for 65 h. Quenched with saturated aqueous sodium bicarbonate solution, and after $CO_2$ evolution ceased it was extracted with dichloromethane (3×30 mL), and the combined organic layers were washed with brine (50 mL), dried over sodium sulfate, filtered and concentrated under reduced pressure, the residue was purified by silica gel column (petroleum ether) to give 1-bromo-3-(2,2-difluoro-3,3-dimethylbutoxy)benzene as colorless oil (1.56 g, 66% yield).

LCMS: LC retention time 2.35 min. MS (ESI) m/z not observation.

$^{1}$HNMR (400 MHz, chloroform-d) δ 7.18-7.10 (m, 3H), 6.88 (m, 1H), 4.23 (t, J=13.2 Hz, 2H), 1.14 (s, 9H).

Step 4

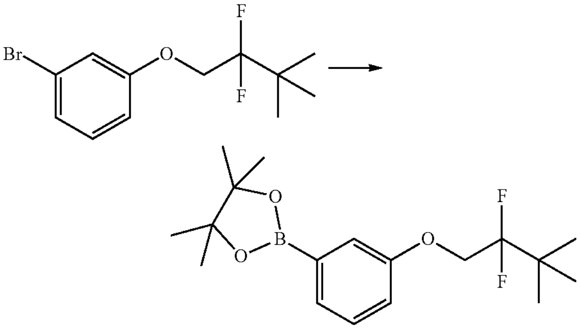

The mixture of 1-bromo-3-(2,2-difluoro-3,3-dimethylbutoxy)benzene (1.56 g, 5.32 mmol), 4,4,5,5-tetramethyl-2-(4,4,5,5-tetramethyl-1,3,2-dioxaborolan-2-yl)-1,3,2-dioxaborolane (2.03 g, 7.99 mmol), potassium acetate (1.56 g, 15.96 mmol), and [1,1-bis (diphenylphosphino)ferrocene] dichloropalladium (II) (389 mg, 0.532 mmol) in anhydrous 1,4-dioxane (20.0 mL) was stirred at 90° C. under argon atmosphere overnight. The solid was filtered off, diluted with water (120 mL), extracted with ethyl acetate (3×50 mL), the combined organic layers were washed with brine (100 mL), dried over sodium sulfate, filtered and concentrated under reduced pressure, the residue was purified by silica gel column (3% ethyl acetate in petroleum ether) to give 2-(3-(2,2-difluoro-3,3-dimethylbutoxy)phenyl)-4,4,5,5-tetramethyl-1,3,2-dioxaborolane as a colorless oil (1.343 g, 74% yield).

LCMS: LC retention time 2.42 min. MS (ESI) m/z 340 $[M+H]^+$

Intermediate C 4,4,5,5-Tetramethyl-2-(3-((1S)-3-(trifluoromethoxy) cyclopentyl)phenyl)-1,3,2-dioxaborolane

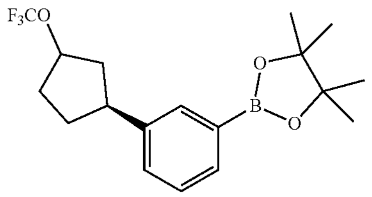 [SMILES: CC1(C)OB(c2cccc([C@H]3CCC(OC(F)(F)F)C3)c2)OC1(C)C]

Step 1

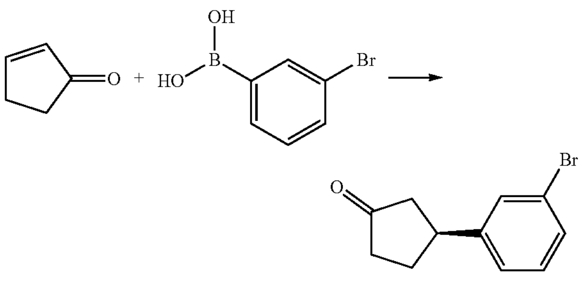

To a mixture of 6.84 g (34.2 mmol) of (3-bromophenyl) boronic acid, 188.6 mg (0.74 mmol) of acetylacetonatobis (ethylene)rhodium (I) and 455 mg (0.74 mmol) of s-BINAP in 40 mL of dioxane and 4 mL of $H_2O$ under nitrogen was added 2.0 g (24.4 mmol) of cyclopent-2-en-1-one. After refluxing for 5.0 h, the reaction was concentrated. The residue was partitioned between 100 mL of EtOAc and 100 mL of 1N $NaHCO_3$. After separating phases, the organic layer was washed with 100 mL of brine, dried over $Na_2SO_4$ and concentrated. The residue was purified by flash column chromatography (PE/EA=5/1) to afford 4.7 g of (S)-3-(3-bromophenyl)cyclopentan-1-one as alight yellow solid.

LCMS: LC retention time 2.14 min. MS (ESI) m/z 241 $[M+H]^+$.

Step 2

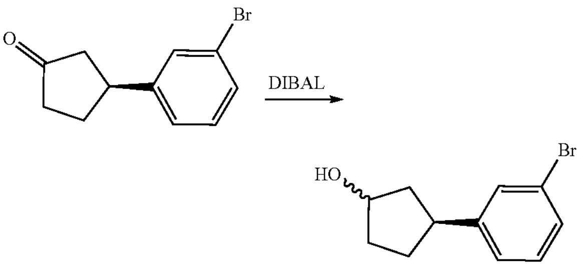

A solution of (S)-3-(3-bromophenyl)cyclopentan-1-one (4.58 g, 19.2 mmol) in anhydrous tetrahydrofuran (40.0 mL) was cooled to −78° C. and added DIBAL (1M in toluene) (76.7 mL) at the same temperature under argon atmosphere. Then the mixture was allowed to warm to room temperature slowly and stirred at room temperature for overnight. Then saturated potassium sodium tartrate tetrahydrate solution (80 mL) was added and stirred for another hour, and the mixture was filtered through a celite plug. The filtrate was concentrated under reduced pressure to give the crude product which was purified by flash reversed phase column to give (3S)-3-(3-bromophenyl)cyclopentan-1-ol (3.25 g, yield: 70.4%) as colorless oil.

LCMS: LC retention time 2.05 min. MS (ESI) m/z 225 $[M-H_2O]^+$.

Step 3

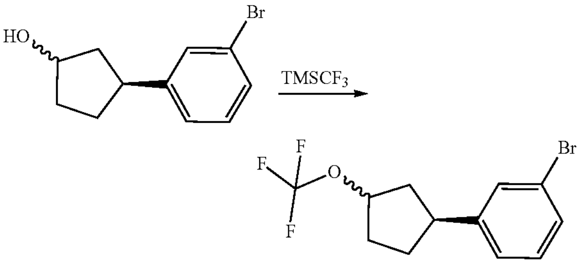

To a flask was added AgOTf (3.20 g, 12.4 mmol), Select-F® (2.20 g, 6.22 mmol), KF (964 mg, 16.6 mmol) and (3S)-3-(3-bromophenyl)cyclopentan-1-ol (1.0 g, 4.15 mmol) was purged with argon, then EtOAc (20 mL) was added to, followed by $TMSCF_3$ (1.77 g, 12.4 mmol), 2-fluoropyridine (1.21 g, 12.4 mmol). The reaction mixture was stirred at room temperature overnight under argon.

The reaction mixture as filtered through a celite pad. The filtrate was concentrated and purified by flash column chromatography (100% PE) to afford 1-bromo-3-((1S)-3-(trifluoromethoxy)cyclopentyl)benzene (402 mg, Yield: 31.4%) as colorless oil.

$^1H$ NMR (400 MHz, chloroform-d) δ 7.36 (dd, J=16.2, 9.0 Hz, 2H), 7.16 (dd, J=15.8, 6.8 Hz, 2H), 4.85 (d, J=28.0 Hz, 1H), 3.39-2.95 (m, 1H), 2.61-2.21 (m, 2H), 2.16-1.59 (m, 5H).

Step 4

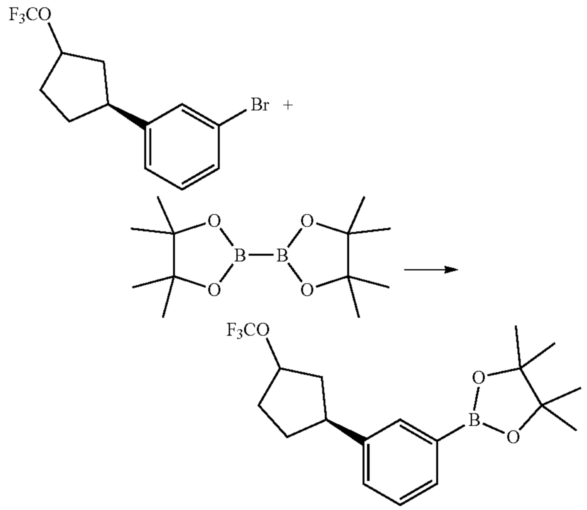

The reaction mixture of 1-bromo-3-[(1S)-3-(trifluoromethoxy) cyclopentyl]benzene (1.0 g, 3.23 mmol) in dioxane (20 mL) was added 2,4,4,5,5-pentamethyl-1,3,2-dioxaborolane (1.38 g, 4.85 mmol), KOAc (793 mg, 8.09 mmol), Pd(dppf)$Cl_2$ (70.9 mg, 9.70×$10^{-5}$ mol) and stirred at 90° C. overnight under argon. The mixture was concentrated and extracted with EA (10 mL×3), the organic phase was washed with brine (20 mL), the organic phase was concentrated and purified by SGC (PE:EA=10:1) to give 4,4,5,5-tetramethyl-2-[3-[(1S)-3-(trifluoromethoxy)cyclopentyl] phenyl]-1,3,2-dioxaborolane (720 mg, Y: 62.5%) as a light oil.

LCMS (acidic): LC retention time 2.41, MS (ESI): m/z 357 $[M+H]^+$.

Intermediate D

1-Bromo-3-((1S)-3-(trifluoromethoxy)cyclopentyl) benzene

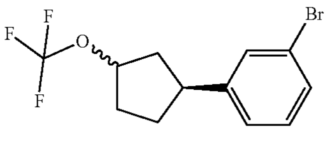 [SMILES: FC(F)(F)OC1CC[C@H](c2cccc(Br)c2)C1]

Step 1

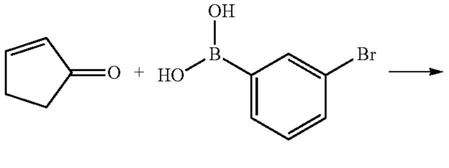

-continued

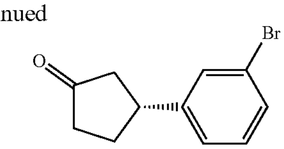

Cyclopent-2-en-1-one (1.0 g, 12.2 mmol) was added to the mixture of (3-bromophenyl)boronic acid (2.94 g, 14.6 mmol), acetylacetonatobis(ethylene)rhodium(I) (189 mg, 0.731 mmol), and (R)-(+)-2,2'-Bis(diphenylphosphino)-1,1'-binaphthyl (758 mg, 1.22 mmol) in 1,4-dioxane (20 mL) and water (2.0 mL) under argon atmosphere at room temperature. The resulting reaction mixture was stirred at 105° C. for 5.5 hrs. After cooling to room temperature, the mixture was concentrated under reduced pressure. Saturated aqueous sodium bicarbonate solution (100 mL) was added, and extracted with ethyl acetate (3×30 mL), the combined organic layers were washed with brine (60 mL), dried over sodium sulfate, filtered and concentrated under reduced pressure, the residue was purified by flash column (petroleum ether:ethyl acetate=5:1) to afford (R)-3-(3-bromophenyl)cyclopentan-1-one as light yellow oil (2.551 g, 88% yield).

LCMS: LC retention time 2.00 min. MS (ESI) m/z 239 $[M+H]^+$ $^1$H NMR (400 MHz, chloroform-d) δ 7.40-7.37 (m, 2H), 7.23-7.17 (m, 2H), 3.43-3.35 (m, 1H), 2.70-2.63 (m, 1H), 2.51-2.41 (m, 2H), 2.35-2.26 (m, 2H), 2.02-1.92 (m, 1H).

Step 2

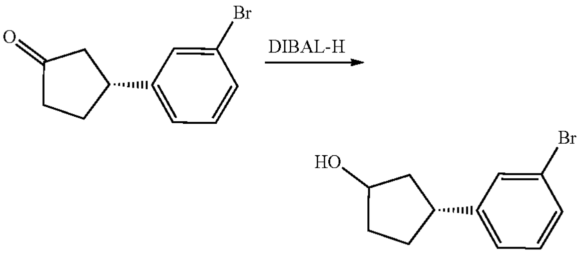

Diisobutylaluminium hydride (6.3 mL, 1 M solution in toluene, 6.3 mmol) was added to the solution of (R)-3-(3-bromophenyl)cyclopentan-1-one (1.0 g, 4.18 mmol) in anhydrous tetrahydrofuran (10.0 mL) at −78° C. under argon atmosphere, the resulting reaction mixture was stirred at the same temperature for 2.0 hours. The reaction was quenched by adding methanol (5.0 mL) dropwise at −78° C., then the mixture was allowed to warm to room temperature, and saturated aqueous potassium sodium tartrate tetrahydrate solution (50 mL) was added. The resulting mixture was stirred overnight at room temperature. Extracted with ethyl acetate (3×30 mL), the combined organic layers were washed with brine (30 mL), dried over sodium sulfate, filtered and concentrated under reduced pressure, the residue was purified by silica gel column (30% ethyl acetate in petroleum ether) to give (3R)-3-(3-bromophenyl)cyclopentan-1-ol as colorless oil (798 mg, 79% yield).

LCMS: LC retention time 1.97 min. MS (ESI) m/z 223 $[M-H_2O]^+$ $^1$H NMR (400 MHz, chloroform-d) δ 7.44-7.37 (m, 1H), 7.33-7.30 (m, 1H), 7.23-7.14 (m, 2H), 4.55-4.43 (m, 1H), 3.41-2.97 (m, 1H), 2.49-2.07 (m, 2H), 1.95-1.79 (m, 2H), 1.74-1.58 (m, 2H).

Step 3

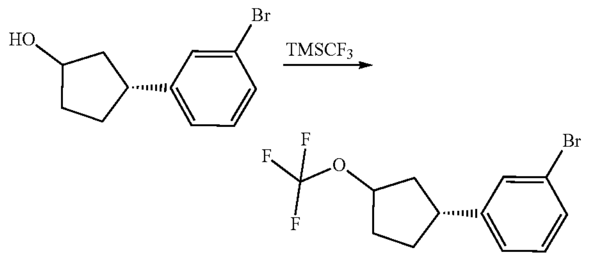

(Trifluoromethyl)trimethylsilane (1.41 g, 9.93 mmol) was added to the mixture of (3R)-3-(3-bromophenyl)cyclopentan-1-ol (798 mg, 3.31 mmol), silver trifluoromethane sulfonate (2.55 g, 9.93 mmol), 1-chloromethyl-4-fluoro-1,4-diazoniabicyclo[2.2.2]octane bis(tetrafluoroborate) (1.758 g, 4.97 mmol) and potassium fluoride (0.768 g, 13.24 mmol) in ethyl acetate (15.0 mL) under argon atmosphere at room temperature, followed by 2-fluoropyridine (0.963 g, 9.93 mmol). The resulting reaction mixture was stirred at room temperature for 94 hours. Filtered through a celite pad, the filtrate was concentrated and purified by silica gel column (100% petroleum ether) to afford 1-bromo-3-((1R)-3-(trifluoromethoxy)cyclopentyl)benzene as colorless oil (468 mg, 46% yield).

LCMS: LC retention time 2.74 min. MS (ESI) not observed.

$^1$H NMR (400 MHz, chloroform-d) δ 7.40-7.33 (m, 2H), 7.19-7.13 (m, 2H), 4.90-4.79 (m, 1H), 3.37-2.98 (m, 1H), 2.59-2.32 (m, 1H), 2.29-1.63 (m, 5H).

Intermediate E and F 3-(Neopentyloxy)-1H-pyrazole and 3-(3,3-dimethylbutoxy)-1H-pyrazole

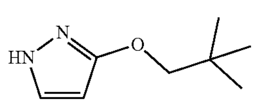

and

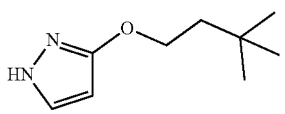

Step 1

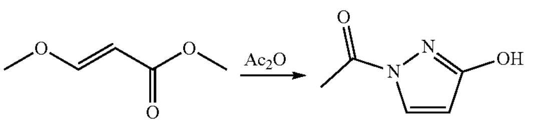

To a stirred solution of methyl (E)-3-methoxyacrylate (6.0 g, 51.72 mmol) in MeOH (50 mL) was added hydrazine hydrate (30 mL) at room temperature, the mixture solution was stirred under reflux for 16 hours. After the reaction was completed, the solvent was removed. The residue (3.69 g, 43.93 mmol) was dissolved in pyridine (30 mL) and $Ac_2O$ (4.7 g, 46.12 mmol) was added slowly at 95° C. Then the mixture solution was stirred at 95° C. for 2 hours. The solvent was removed under reduced pressure and the residue was added $Et_2O$ (60 mL). The slurry was stirred overnight at room temperature, then the solid was filtered off and rinsed with $Et_2O$ (30 mL) to afford 1-(3-hydroxy-1H-pyrazol-1-yl)ethan-1-one (4.32 g, 78%) as a light yellow solid.

LCMS Purity: 93%; MS (ESI) m/z 127 [M+H]$^+$.

Step 2a

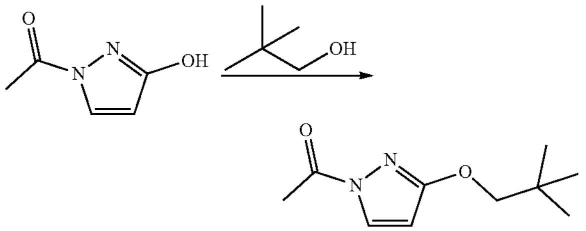

To a stirred solution of 1-(3-hydroxy-1H-pyrazol-1-yl)ethan-1-one (4.32 g, 34.29 mmol), 2,2-dimethylpropan-1-ol (3.0 g, 34.29 mmol) and $PPh_3$ (9.88 g, 37.72 mmol) in THF (100 mL) was added DIAD (7.62 g, 37.72 mmol) at room temperature, the mixture solution was stirred at room temperature for 16 hours. Diluted with water (50 mL) and extracted with EA (30 mL×3), washed with brine (20 mL×2), dried over anhydrous $Na_2SO_4$, filtered and concentrated in vacuo, the residue was purified by silica gel chromatography (EA/PE=1/10) to afford 1-(3-(neopentyloxy)-1H-pyrazol-1-yl)ethan-1-one (3.3 g, 49%) as a light yellow solid.

LCMS Purity: 91%; MS (ESI) m/z 197 [M+H]$^+$.

Step 3a

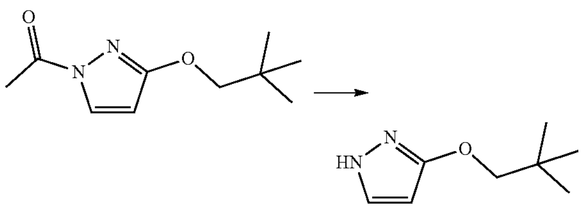

To a stirred solution of 1-(3-(neopentyloxy)-1H-pyrazol-1-yl)ethan-1-one (3.3 g, 16.84 mmol) in MeOH/$H_2O$ (30 mL/3 mL) was added NaOH (673 mg, 16.84 mmol) at room temperature, the mixture solution was stirred at room temperature for 16 hours. Diluted with water (30 mL) and extracted with EA (20 mL×3), washed with brine (20 mL×2), dried over anhydrous $Na_2SO_4$, filtered and concentrated in vacuo, the residue was purified by silica gel chromatography (EA/PE=1/5) to afford 3-(neopentyloxy)-1H-pyrazole (2 g, 80%) as an yellow oil.

LCMS Purity: 87%; MS (ESI) m/z 155 [M+H]$^+$.

Step 2b.

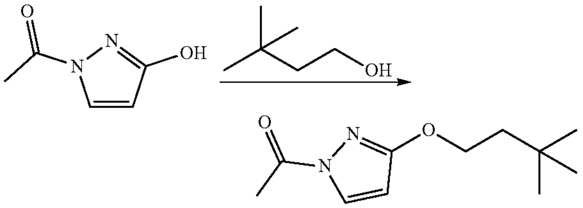

To a stirred solution of 1-(3-hydroxy-1H-pyrazol-1-yl) ethan-1-one (3.8 g, 30.16 mmol), 2,2-dimethylpropan-1-ol (3.69 g, 36.19 mmol) and $PPh_3$ (11.85 g, 45.24 mmol) in THF (200 mL) was added DIAD (9.14 g, 45.24 mmol) at room temperature, the mixture was stirred at room temperature for 16 hours. Diluted with water (50 mL) and extracted with EA (30 mL×3), washed with brine (20 mL×2), dried over anhydrous $Na_2SO_4$, filtered and concentrated to afford 1-(3-(3,3-dimethylbutoxy)-1H-pyrazol-1-yl)ethan-1-one (8.8 g, crude) as a yellow solid, which used directly in the next step without further purification.

LCMS Purity: 73%; MS (ESI) m/z 211 $[M+H]^+$.

Step 3b.

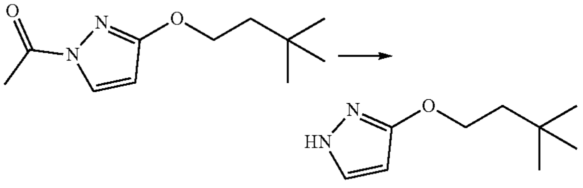

To a stirred solution of 1-(3-(3,3-dimethylbutoxy)-1H-pyrazol-1-yl)ethan-1-one (8.8 g, 41.9 mmol) in $MeOH/H_2O$ (100 mL/10 mL) was added NaOH (1.68 g, 41.9 mmol) at room temperature, the mixture solution was stirred at room temperature for 16 hours. Diluted with water (50 mL) and extracted with EA (30 mL×3), washed with brine (30 mL×2), dried over anhydrous $Na_2SO_4$, filtered and concentrated in vacuo, the residue was purified by silica gel chromatography (EA/PE=1/4) to afford 3-(3,3-dimethylbutoxy)-1H-pyrazole (2.6 g, 51% for two steps) as yellow oil.

LCMS Purity: 92%; MS (ESI) m/z 169 $[M+H]^+$.

Intermediate G

Methyl 3-methyl-1-(3-sulfamoylphenyl)piperidine-3-carboxylate

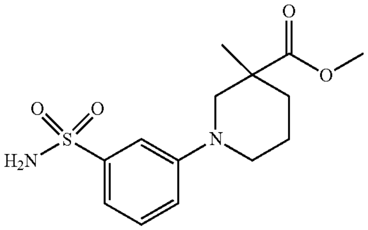 [SMILES: COC(=O)C1(C)CCCN(c2cccc(S(N)(=O)=O)c2)C1]

Step 1

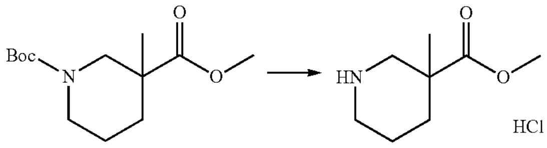 [SMILES: COC(=O)C1(C)CCCN(C(=O)OC(C)(C)C)C1 ; COC(=O)C1(C)CCCNC1 ; Cl]

To a solution of 1-(tert-butyl) 3-methyl 3-methylpiperidine-1,3-dicarboxylate (2.00 g, 0.00777 mol) in dioxane (10.0 mL) was added HCl in dioxane (4.00 M, 11.2 mL, 0.0447 mol). The mixture was stirred at room temperature for 12 hours. TLC (PE/EA=8/1) showed the starting material was consumed, the mixture was evaporated to dryness to give methyl 3-methylpiperidine-3-carboxylate hydrochloride (0.140 g, 0.00775 mol, yield: 99.7%) as a white solid.

Step 2

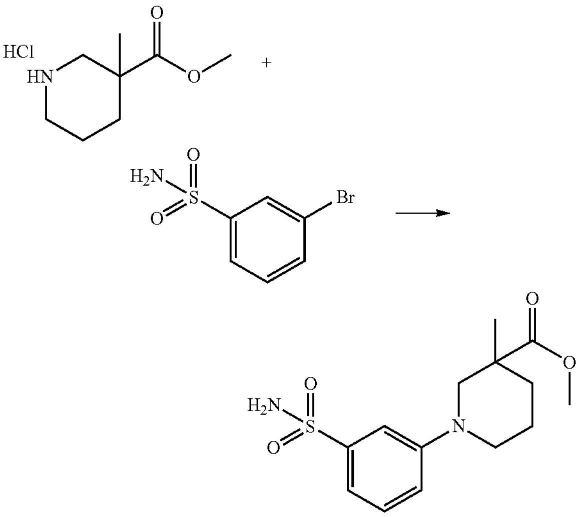

To a solution of methyl 3-methylpiperidine-3-carboxylate hydrochloride (0.500 g, 0.00258 mol) in DMSO (8.00 mL) was added 3-bromobenzenesulfonamide (0.508 g, 0.00215 mol), $K_2CO_3$ (0.714 g, 0.00516 mol), CuI (30.0%, 0.328 g, 0.000516 mol), L-proline (0.0892 g, 0.000775 mol), then the mixture was degassed and purged with $N_2$ for 3 times, the mixture was stirred at 90° C. for 16 hours. LCMS showed the desired MS was detected, $H_2O$ (16 mL) was added and the mixture extracted with EA (10 mL×3), the combined organic layers were dried over $Na_2SO_4$, filtered and concentrated to dryness to give the crude product, which was purified by prep-HPLC to give methyl 3-methyl-1-(3-sulfamoylphenyl)piperidine-3-carboxylate (0.100 g, 0.000320 mol, yield: 12.4%) as a yellow solid.

LCMS: LC retention time 1.82 min. MS (ESI) mz 313 $[M+H]^+$

EXAMPLES

Example 1

N-(5-(3-(2,2-difluoro-3,3-dimethylbutoxy)phenyl)-6-(2-isopropylphenyl)pyrazin-2-yl)benzenesulfonamide

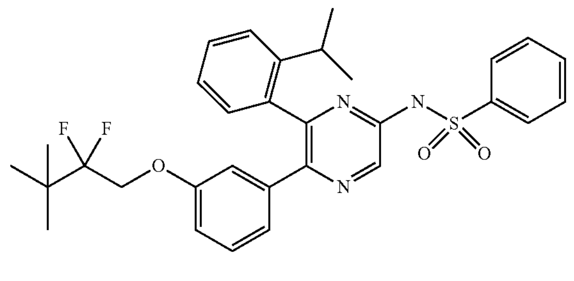 [SMILES: CC(C)c1ccccc1-c1nc(NS(=O)(=O)c2ccccc2)cnc1-c1cccc(OCC(F)(F)C(C)(C)C)c1]

Synthesis Scheme

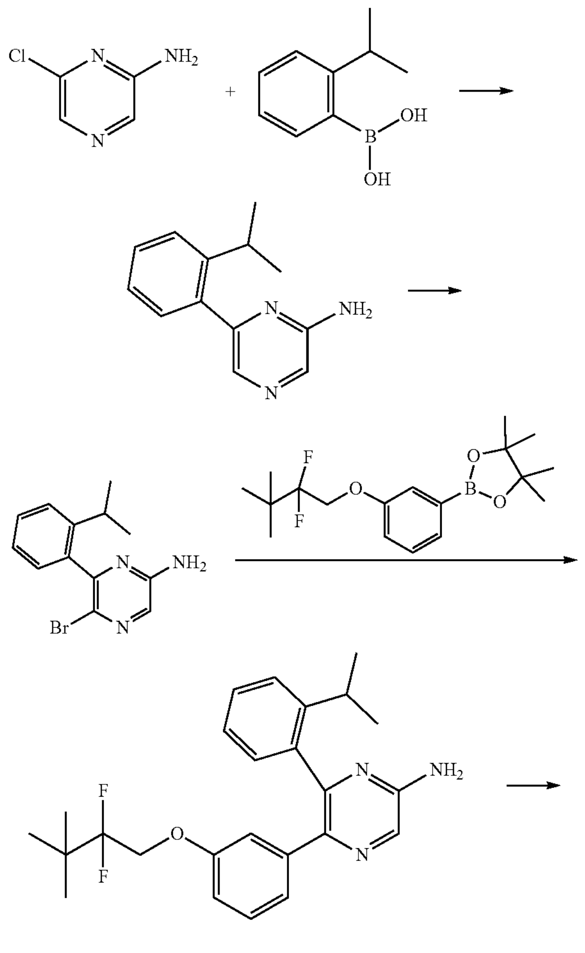

-continued

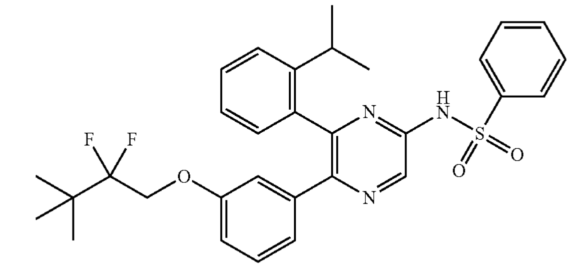

Step 1

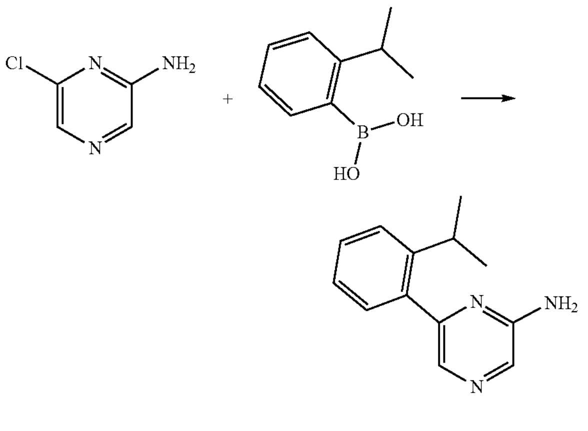

To a solution of 6-chloropyrazin-2-amine (1.3 g, 10 mmol) in DMF/$H_2O$ (v/v=6/1) (35 mL) were added (2-isopropylphenyl)boronic acid (1.97 g, 12 mmol), $Cs_2CO_3$ (9.81 g, 30.1 mmol), and Pd(dppf)$Cl_2$ (734 mg, 1.0 mmol). The reaction was conducted in a microwave oven set at 120° C. for 3 hours. The reaction solution was filtered and diluted with EA (100 mL), washed with water (100 mL×3) and dried over anhydrous $Na_2SO_4$. Filtered and the filtrate was concentrated under reduced pressure to afford the crude product which was purified by SGC (PE:EA=2:1) to give 6-(2-isopropylphenyl)pyrazin-2-amine (1.81 g, Y: 84.6%) as yellow solid.

LCMS (acidic): LC retention time 1.888 min, MS (ESI): m/z 214 $[M+H]^+$.

Step 2

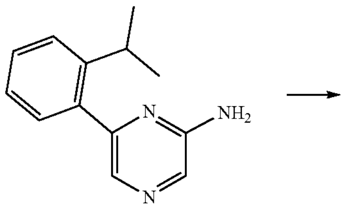

-continued

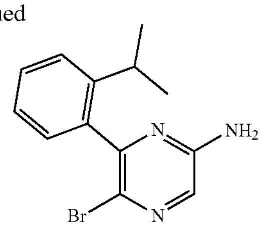

To a solution of 6-(2-isopropylphenyl)pyrazin-2-amine (1 g, 4.69 mmol) in a mixture of DMSO (60 mL) and water (1.5 mL) cooled to 0° C., was added NBS (835 mg, 4.69 mmol). The resulting mixture was stirred at room temperature for 3 h. The reaction was diluted with ethyl acetate (100 mL), washed with water (50 mL×3). The combined organics were concentrated under reduced pressure. The residue was purified by reversed phase column (MeCN/$H_2O$=0-70%) to give 5-bromo-6-(2-isopropylphenyl)pyrazin-2-amine (990 mg, yield: 59.3%) as a yellow solid.

LCMS (acidic): LC retention time 2.032, MS (ESI): m/z 294 $[M+H]^+$.

Step 3

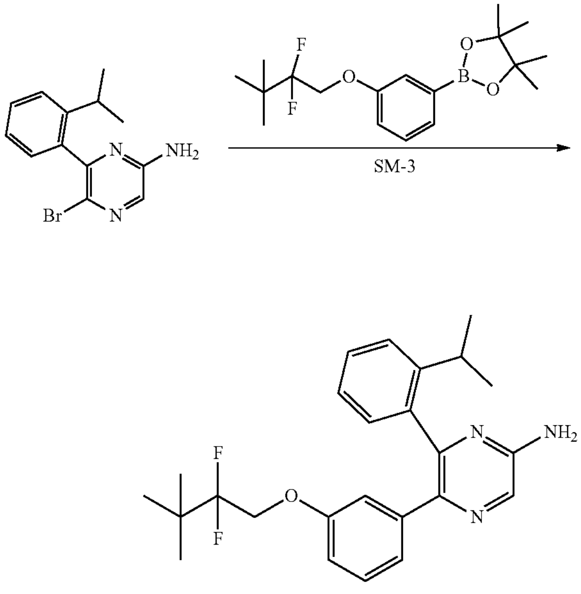 [SMILES: CC(C)c1ccccc1-c1nc(N)cnc1Br ; CC(C)(C)C(F)(F)COc1cccc(B2OC(C)(C)C(C)(C)O2)c1 ; CC(C)c1ccccc1-c1nc(N)cnc1-c1cccc(OCC(F)(F)C(C)(C)C)c1]

To a solution of 5-bromo-6-(2-isopropylphenyl)pyrazin-2-amine (250 mg, 0.856 mmol) in toluene/EtOH/$H_2O$ (v/v/v=4/2/1) (7 mL), 2-(3-(2,2-difluoro-3,3-dimethylbutoxy)phenyl)-4,4,5,5-tetramethyl-1,3,2-dioxaborolane (349 mg, 1.03 mmol), $Na_2CO_3$ (272 mg, 2.57 mmol) and $Pd(PPh_3)_4$ (cat.) were added. The result mixture was reacted under an argon atmosphere at 90° C. for 4 h. The reaction mixture was concentrated, diluted with EtOAc (50 mL), washed with water (50 mL×3). The organics were dried over $Na_2SO_4$, filtered, concentrated and purified by SGC (PE:EA=3:1) to afford 5-(3-(2,2-difluoro-3,3-dimethylbutoxy)phenyl)-6-(2-isopropylphenyl)pyrazin-2-amine (180 mg, yield: 49.4%) as yellow solid.

LCMS (acidic): LC retention time 2.546 min., MS (ESI): m/z 426 $[M+H]^+$.

Step 4

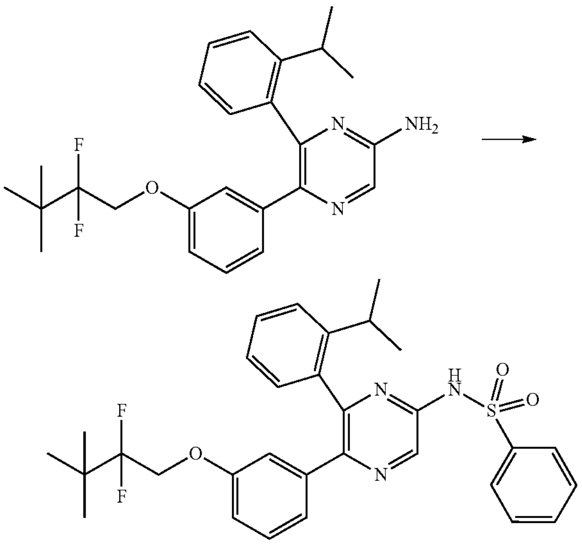

The reaction mixture of 5-(3-(2,2-difluoro-3,3-dimethylbutoxy)phenyl)-6-(2-isopropylphenyl)pyrazin-2-amine (80 mg, 0.188 mmol) and benzenesulfonyl chloride (99.6 mg, 0.564 mmol) in pyridine (2 mL) was stirred at room temperature for 3 hours. Diluted with EtOAc (50 mL), washed with brine (50 mL×3). The organic solution was dried over $Na_2SO_4$, filtered and concentrated to give the crude which was purified by Prep-HPLC to afford N-(5-(3-(2,2-difluoro-3,3-dimethylbutoxy)phenyl)-6-(2-isopropylphenyl)pyrazin-2-yl)benzenesulfonamide (71.8 mg, yield: 67.5%) as a white solid.

LCMS (acidic): LC retention time 2.588, MS (ESI): m/z 566 $[M+H]^+$.

$^1H$ NMR (400 MHz, methanol-$d_4$) δ 8.82 (s, 1H), 7.98 (d, J=7.2 Hz, 2H), 7.63 (t, J=7.4 Hz, 1H), 7.53 (t, J=7.8 Hz, 2H), 7.39-7.3 (m, 2H), 7.30 (s, 1H), 7.24-7.15 (m, 2H), 7.10-7.06 (m, 2H), 6.87-6.77 (m, 2H), 3.88 (t, J=13.2 Hz, 1H), 2.52-2.44 (m, 1H), 1.09 (s, 9H), 0.93-0.67 (m, 6H).

Example 2

N-(5-(3-(2,2-difluoro-3,3-dimethylbutoxy)phenyl)-6-(2,6-dimethylphenyl)pyrazin-2-yl)benzenesulfonamide

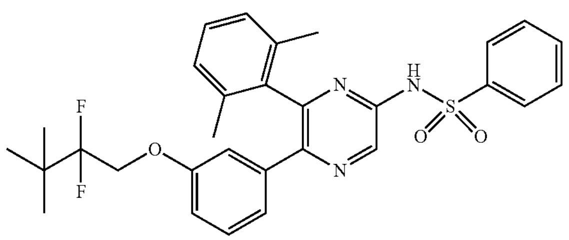 [SMILES: Cc1cccc(C)c1-c1nc(NS(=O)(=O)c2ccccc2)cnc1-c1cccc(OCC(F)(F)C(C)(C)C)c1]

Example 2 was synthesized by essentially the same protocol as Example 1 starting from 6-chloropyrazin-2-amine coupled with (2,6-dimethylphenyl)boronic acid, bromination, followed by condensation with 2-(3-(2,2-difluoro-3,3- dimethylbutoxy)phenyl)-4,4,5,5-tetramethyl-1,3,2-dioxaborolane, and finally sulfonamide formation similarly to give N-(5-(3-(2,2-difluoro-3,3-dimethylbutoxy)phenyl)-6-(2,6-dimethylphenyl)pyrazin-2-yl)benzenesulfonamide (Example 2).

LCMS (acidic): LC retention time 2.301, MS (ESI): m/z 552 $[M+H]^+$.

$^1$H NMR (400 MHz, methanol-$d_4$) δ 8.50 (s, 1H), 7.95-7.92 (m, 2H), 7.62-7.58 (m, 1H), 7.46 (t, J=7.8 Hz, 2H), 7.22-7.16 (m, 2H), 7.09-7.04 (m, 3H), 6.88-6.86 (m, 1H), 6.86-6.71 (m, 1H), 3.92 (t, J=13.4 Hz, 2H), 1.76 (s, 6H), 1.09 (s, 9H).

Example 3

N-(5-(3-(3,3-dimethylbutoxy)phenyl)-6-(2,6-dimethylphenyl)pyrazin-2-yl)benzenesulfonamide

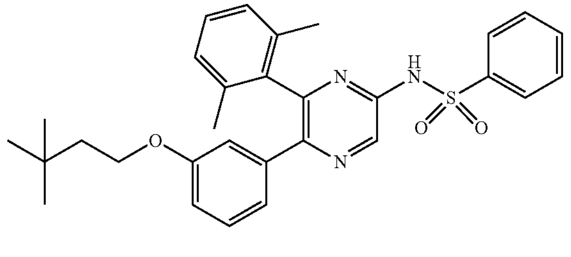 [SMILES: Cc1cccc(C)c1-c1nc(NS(=O)(=O)c2ccccc2)cnc1-c1cccc(OCCC(C)(C)C)c1]

Example 3 was synthesized by essentially the same protocols as Example 1.

LCMS (acidic): LC retention time 2.441, MS (ESI): m/z 516.3 $[M+H]^+$.

$^1$H NMR (400 MHz, methanol-$d_4$) δ 8.50 (s, 1H), 7.94 (d, J=7.6 Hz, 2H), 7.60 (t, 1H), 7.46 (t, 2H), 7.21-7.12 (m, 2H), 7.05-7.01 (m, 3H), 6.80-6.76 (m, 1H), 6.67 (s, 1H), 3.64 (t, 2H), 1.75 (s, 1H), 1.59 (t, 2H), 0.96 (s, 9H).

Example 4

N-(6-(2,6-dimethylphenyl)-5-(4-fluoro-3-(3,3,3-trifluoro-2,2-dimethylpropoxy)phenyl)pyrazin-2-yl) benzenesulfonamide

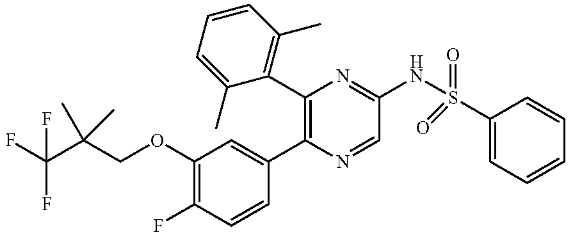 [SMILES: Cc1cccc(C)c1-c1nc(NS(=O)(=O)c2ccccc2)cnc1-c1ccc(F)c(OCC(C)(C)C(F)(F)F)c1]

Example 4 was synthesized by essentially the same protocol as Example 1.

LCMS (acidic): LC retention time 2.441, MS (ESI): m/z 516 $[M+H]^+$.

$^1$H NMR (400 MHz, methanol-$d_4$) δ 8.51 (s, 1H), 7.94 (d, J=8.0 Hz), 7.60 (t, 1H), 7.45 (t, 2H), 7.24-7.16 (m, 2H), 7.09-7.01 (m, 3H), 6.76-6.73 (m, 1H), 3.46 (s, 2H), 1.75 (s, 6H), 1.20 (s, 6H).

Example 5

N-(5-(3-(2,2-difluoro-3,3-dimethylbutoxy)-1H-pyrazol-1-yl)-6-(2-isopropylphenyl)pyrazin-2-yl)benzenesulfonamide

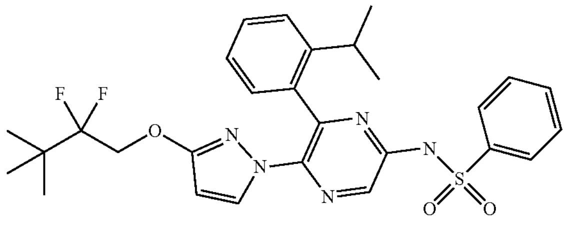 [SMILES: CC(C)c1ccccc1-c1nc(NS(=O)(=O)c2ccccc2)cnc1-n1ccc(OCC(F)(F)C(C)(C)C)n1]

Synthetic Scheme

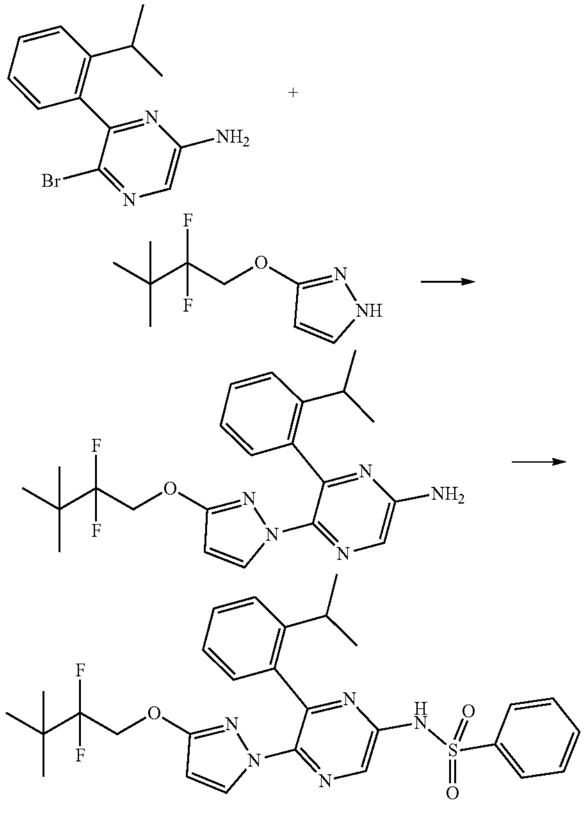

Step 1

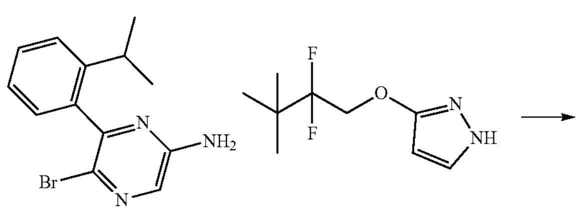

-continued

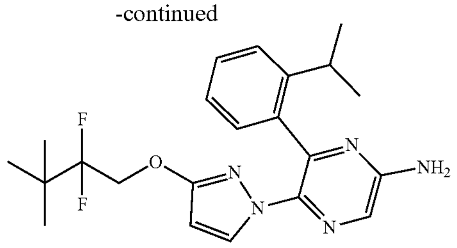

The mixture of 3-(2,2-difluoro-3,3-dimethylbutoxy)-1H-pyrazole (100 mg, 0.490 mmol), 5-bromo-6-(2-isopropylphenyl)pyrazin-2-amine, the intermediate obtained from Example 1, (186 mg, 0.637 mmol), $K_2CO_3$ (169 mg, 1.22 mmol), L-(−)-proline (28 mg, cat.) and copper(I) iodide (10 mg, cat.) was reacted in glovebox at 100° C. for overnight. The reaction was diluted with $NH_4Cl$ (100 mL), extracted with ethyl acetate (50 mL×2). The combined organics concentrated under reduced pressure. The residue was purified by reversed phase column to afford 5-(3-(2,2-difluoro-3,3-dimethylbutoxy)-1H-pyrazol-1-yl)-6-(2-isopropylphenyl) pyrazin-2-amine (40 mg, 19.7%) as yellow solid. LCMS (acidic): LC retention time 2.228 min. MS (ESI) m/z 416 $[M+H]^+$.

Step 2

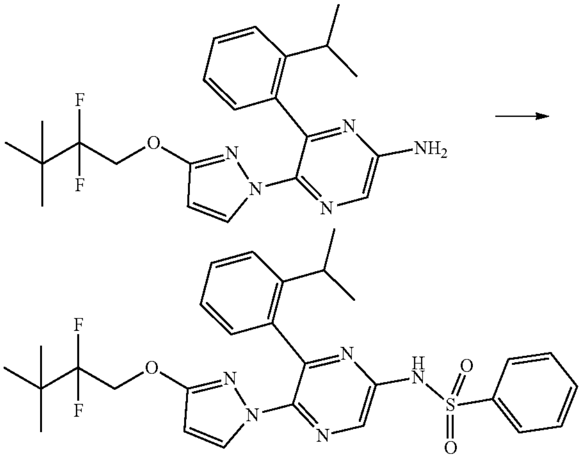

The reaction mixture of 5-(3-(2,2-difluoro-3,3-dimethylbutoxy)-1H-pyrazol-1-yl)-6-(2-isopropylphenyl)pyrazin-2-amine (40 mg, 0.096 mmol) and benzenesulfonyl chloride (51 mg, 0.289 mmol) in pyridine (2 mL) was stirred at room temperature for 3 hours. Diluted with EtOAc (50 mL), washed with brine (50 mL×3). The organics were dried over $Na_2SO_4$, filtered and concentrated to give the crude, which was purified by Prep-HPLC to afford N-(5-(3-(2,2-difluoro-3,3-dimethylbutoxy)-1H-pyrazol-1-yl)-6-(2-isopropylphenyl)pyrazin-2-yl)benzenesulfonamide (14.3 mg, yield: 26.7%) as a white solid.

LCMS (acidic): LC retention time 2.359, MS (ESI): m/z 556 $[M+H]^+$.

$^1$H NMR (400 MHz, methanol-$d_4$) δ 8.33 (s, 1H), 7.93 (d, 3H), 7.60 (t, J=7.2 Hz, 2H), 7.48 (t, J=7.6 Hz, 2H), 7.38-7.33 (m, 2H), 7.19 (t, J=6.8 Hz, 2H), 6.97 (t, J=1.6 Hz, 1H), 5.84 (s, 1H), 3.86 (t, J=14.6 Hz, 2H), 2.53-2.46 (m, 1H), 1.01 (s, 9H), 0.94 (t, J=6.8 Hz, 1H).

Example 6a

N-(6-(2,6-dimethylphenyl)-5-(3-((1R,3S)-3-(trifluoromethoxy)cyclopentyl)phenyl)pyrazin-2-yl)benzenesulfonamide

P1

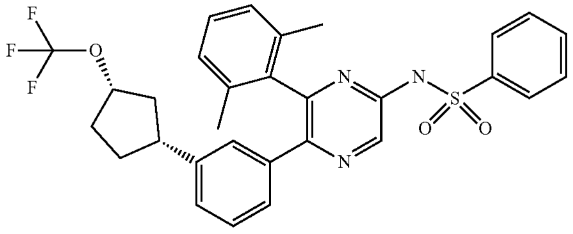

Chiral

Example 6b

N-(6-(2,6-dimethylphenyl)-5-(3-((1R,3R)-3-(trifluoromethoxy)cyclopentyl)phenyl)pyrazin-2-yl)benzenesulfonamide

P2

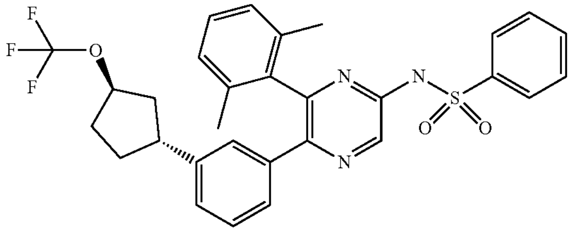

Chiral

Synthesis Scheme

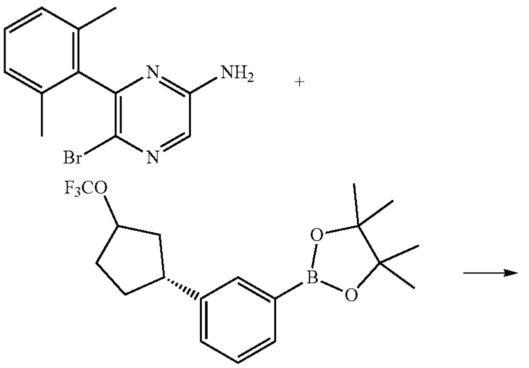

-continued

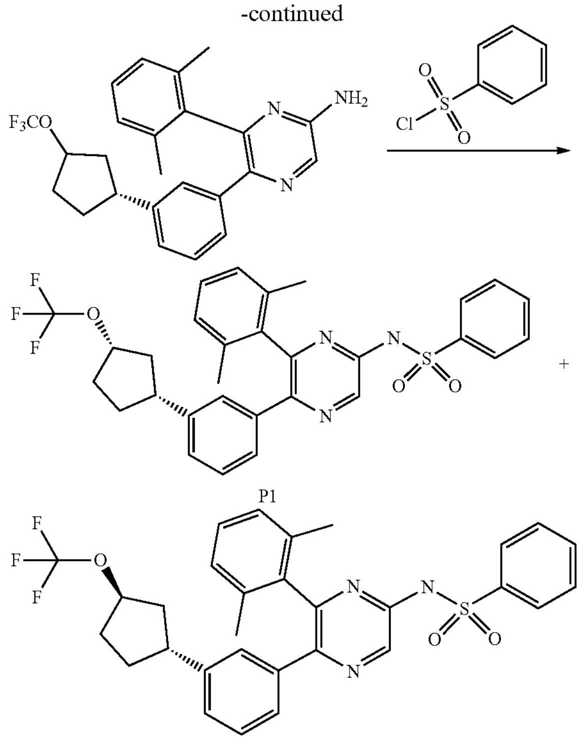

P1

P2

Step 1

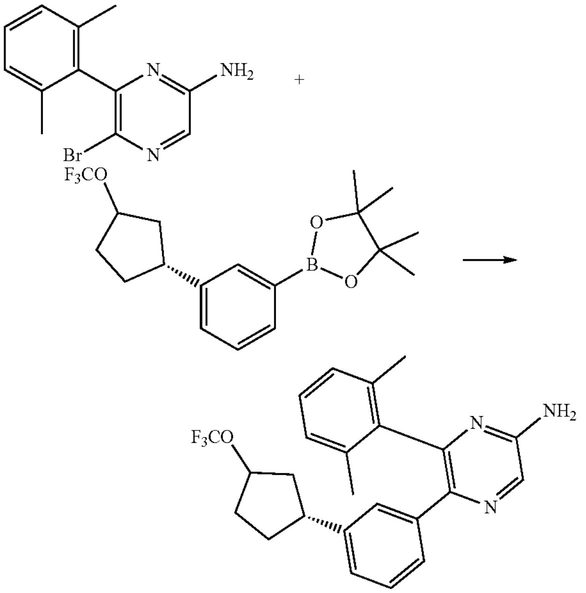

To a mixture of 5-bromo-6-(2,6-dimethylphenyl)pyrazin-2-amine, obtained from Example 2, (400 mg, 1.44 mmol), 4,4,5,5-tetramethyl-2-(3-((1R)-3-(trifluoromethoxy) cyclopentyl)phenyl)-1,3,2-dioxaborolane (614 mg, 1.73 mmol) and $Na_2CO_3$ (152 mg, 4.31 mmol) in toluene/EtOH/$H_2O$ (=4 mL/2 mL/1 mL) was added $Pd(PPh_3)_4$ (166 mg, 0.144 mmol) slowly under argon at room temperature. Then the reaction mixture was stirred at 90° C. for 10 h, allowed to cool to room temperature. The water (20 mL) was added, then extracted by EA (20 mL×3), dried over $Na_2SO_4$, and concentrated in vacuo. The crude was purified by silica gel chromatography (PE/EA=2/1) to afford the desired product 6-(2,6-dimethylphenyl)-5-(3-((1R)-3-(trifluoromethoxy)cyclopentyl)phenyl)pyrazin-2-amine (400 mg, 0.936 mmol, 65.1% yield) as yellow solid.

LCMS: LC retention time 2.300 min; MS (ESI) m/z 427 $[M+H]^+$.

Step 2

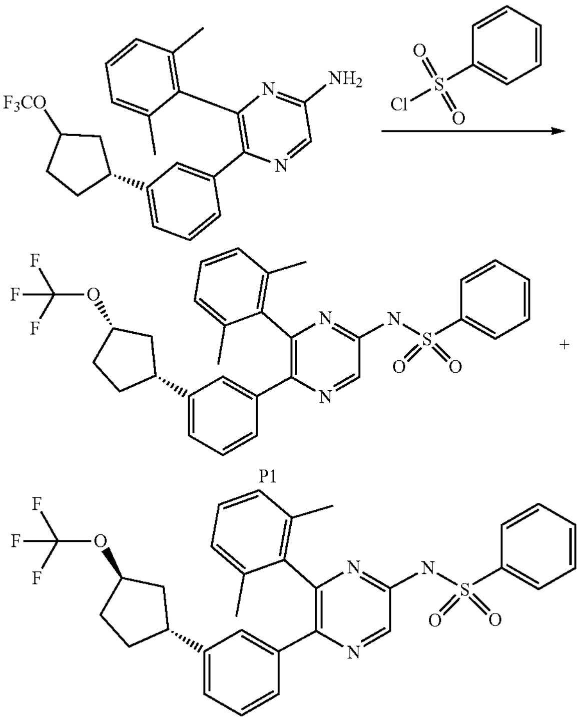

P1

P2

To a mixture of 6-(2,6-dimethylphenyl)-5-(3-((1R)-3-(trifluoromethoxy)cyclopentyl) phenyl)pyrazin-2-amine (150 mg, 0.351 mmol) and benzenesulfonyl chloride (247 mg, 1.4 mmol) in pyridine (2 mL) at room temperature. Then the reaction mixture was stirred at room temperature for 16 h. The reaction mixture was extracted with EA (20 mL×3), washed with water (30 mL×2), dried over $Na_2SO_4$, filtered and concentrated, purified by Prep-HPLC to afford the desired product P1 (24.3 mg) and P2 (30.3 mg) as grey solids.

P1: LCMS: LC retention time 2.431 min, MS (ESI) m/z 568 $[M+H]^+$.

$^1H$ NMR (400 MHz, chloroform-d) δ 8.881 (s, 1H), 7.939-7.919 (m, 2H), 7.608-7.588 (m, 1H), 7.522-7.485 (m, 2H), 7.343-7.325 (m, 1H), 7.211-7.089 (m, 4H), 7.032-7.013 (m, 2H), 4.743-4.72 (m, 1H), 2.896-2.844 (m, 1H), 2.360-2.343 (m, 1H), 1.980-1.917 (m, 3H), 1.765-1.484 (m, 8H).

P2: LCMS: LC retention time 2.452 min, MS (ESI) m/z 568 $[M+H]^+$.

$^1H$ NMR (400 MHz, chloroform-d) δ 8.886 (s, 1H), 7.940-7.921 (m, 2H), 7.627-7.591 (m, 1H), 7.504-7.485 (m, 2H), 7.36-7.342 (m, 1H), 7.283-7.208 (m, 2H), 7.189-7.120 (m, 1H), 7.102-7.02 (m, 3H), 4.751 (s, 1H), 3.212-3.167 (m, 1H), 2.168-2.038 (m, 3H), 1.947-1.882 (m, 1H), 1.727-1.490 (m, 6H), 1332-1.257 (m, 2H).

The stereochemistry of P1 and P2 were assigned arbitrarily.

Example 7a

N-(6-(2,6-dimethylphenyl)-5-(3-((1R,3S)-3-(trifluoromethoxy)cyclopentyl)phenyl)pyrazin-2-yl)-1,3-dimethyl-1H-pyrazole-4-sulfonamide

P1

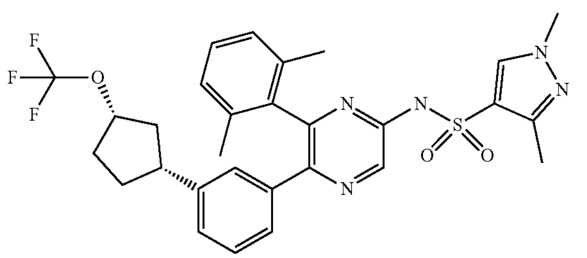

Example 7b

N-(6-(2,6-dimethylphenyl)-5-(3-((1R,3R)-3-(trifluoromethoxy)cyclopentyl)phenyl)pyrazin-2-yl)-1,3-dimethyl-1H-pyrazole-4-sulfonamide

P2

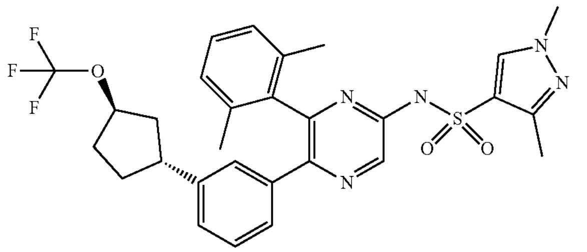

Examples 7a and 7b (P1 and P2) were synthesized similarly using the intermediate 6-(2,6-dimethylphenyl)-5-(3-((1R)-3-(trifluoromethoxy)cyclopentyl)phenyl)pyrazin-2-amine (190 mg, 0.444 mmol), obtained from Example 6, coupled with 1,3-dimethyl-1H-pyrazole-4-sulfonyl chloride (345 mg, 1.78 mmol) in pyridine (2 mL) at room temperature. Then the reaction mixture was stirred at 35° C. for 16 h, allowed to cool to room temperature. The reaction mixture was extracted with EA (20 mL×3), washed with water (30 mL×2), dried over $Na_2SO_4$, filtered and concentrated, purified by prep-HPLC to afford the desired product P1 (43.3 mg) and P2 (25.9 mg) as grey solids.

P1: LCMS: LC retention time 2.228 min, MS (ESI) m/z 586 $[M+H]^+$.

$^1$H NMR (400 MHz, chloroform-d) δ 8.741 (s, 1H), 7.846 (s, 1H), 7.541-7.507 (m, 1H), 7.486-7.444 (m, 1H), 7.282-7.239 (m, 2H), 7.221-7.187 (m, 2H), 7.187-7.07 (m, 2H), 4.767-4.713 (m, 1H), 3.811 (s, 3H), 2.924-2.833 (m, 1H), 2.407-2.335 (m, 4H), 1.947-1.929 (m, 9H), 1.608-1.576 (m, 2H).

P2: LCMS: LC retention time 2.251 min, MS (ESI) m/z 586 $[M+H]^+$.

$^1$H NMR (400 MHz, chloroform-d) δ 8.736 (s, 1H), 7.849 (S, 1H), 7.437 (S, 1H), 7.435-7.372 (m, 2H), 7.353-7.331 (m, 1H), 7.238-7.199 (m, 2H), 7.148-7.109 (m, 2H), 7.076-7.05 (m, 3H), 4.781-4.74 (m, 1H), 2.367 (s, 3H), 2.177-2.046 (m, 3H), 1.957-1.940 (m, 7H), 1.540-1.504 (m, 1H), 1.344-1.324 (m, 1H).

The stereochemistry of P1 and P2 were assigned arbitrarily.

Example 8a

N-(6-(2-isopropylphenyl)-5-(3-((1R,3S)-3-(trifluoromethoxy)cyclopentyl)phenyl)pyrazin-2-yl)-1,3-dimethyl-1H-pyrazole-4-sulfonamide

P1

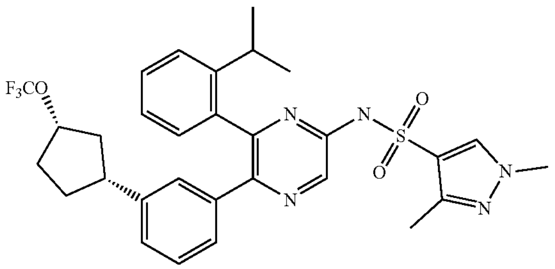

Example 8b

N-(6-(2-isopropylphenyl)-5-(3-((1R,3R)-3-(trifluoromethoxy)cyclopentyl)phenyl)pyrazin-2-yl)-1,3-dimethyl-1H-pyrazole-4-sulfonamide

P2

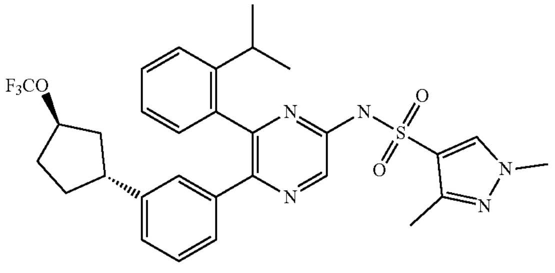

Example 8a and 8b (P1 and P2) were synthesized by essentially the same protocol as Example 7.

P1: LCMS (acidic): LCMS retention time 2.37, MS (ESI): m/z 600 $[M+H]^+$.

$^1$H NMR (400 MHz, chloroform-d) δ 8.73 (s, 1H), 7.89 (s, 1H), 7.45-7.39 (t, 1H), 7.33-7.31 (d, 2H), 7.27-7.22 (m. 2H), 7.20-7.16 (t, 1H), 7.13-7.11 (d, 2H), 4.74-4.72 (m, 1H), 3.82 (s, 3H), 2.88-2.85 (m, 1H), 2.53-2.50 (m, 1H), 2.39 (s, 3H), 2.37-2.32 (m, 1H), 1.97-1.87 (m, 3H), 1.59-1.53 (m, 2H), 0.98 (s, 3H), 0.71 (s, 3H).

P2: LCMS (acidic): LCMS retention time 2.42, MS (ESI): m/z 600.2 $[M+H]^+$.

$^1$H NMR (400 MHz, chloroform-d) δ 8.73 (s, 1H), 7.89 (s, 1H), 7.45-7.39 (t, 1H), 7.33-7.31 (d, 2H), 7.27-7.22 (m. 2H), 7.20-7.16 (t, 1H), 7.13-7.11 (d, 2H), 4.74-4.72 (m, 1H), 3.82 (s, 3H), 3.21-3.14 (m, 1H), 2.56-2.49 (m, 1H), 2.39 (s, 3H), 2.16-2.07 (m, 3H), 1.94-1.87 (m, 1H), 1.32-1.28 (m, 2H), 0.96 (s, 3H), 0.73 (s, 3H).

The stereochemistry of P1 and P2 were assigned arbitrarily.

Example 9a

N-(6-(2-isopropylphenyl)-5-(3-((1R,3S)-3-(trifluoromethoxy)cyclopentyl)phenyl)pyrazin-2-yl)benzenesulfonamide

P1

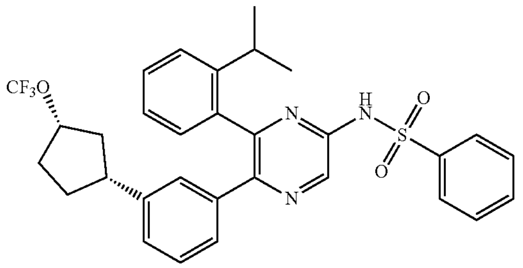

Example 9b

N-(6-(2-isopropylphenyl)-5-(3-((1R,3R)-3-(trifluoromethoxy)cyclopentyl)phenyl)pyrazin-2-yl)benzenesulfonamide

P2

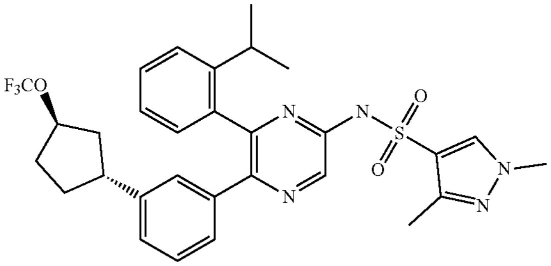

Example 9a and 9b (P1 and P2) were synthesized by essentially the same protocol as Example 8.

P1: LCMS (acidic): LCMS retention time 2.56, MS (ESI): m/z 582.2 $[M+H]^+$.

$^1$H NMR (400 MHz, chloroform-d) δ 8.84 (s, 1H), 7.99-7.97 (t, 2H), 7.63-7.61 (t, 1H), 7.38-7.32 (m, 2H), 7.25-7.19 (m, 3H), 7.12-7.10 (m, 2H), 7.02 (s, 1H), 4.88-4.73 (m, 1H), 3.21-3.14 (m, 1H), 2.46-2.39 (m, 1H), 2.19-2.07 (m, 3H), 1.94-1.87 (m, 1H), 1.53 (s, 2H), 0.90 (s, 3H), 0.62 (s, 3H).

P2: LCMS (acidic): LCMS retention time 2.52, MS (ESI): m/z 582.2 $[M+H]^+$.

$^1$H NMR (400 MHz, chloroform-d) δ 8.84 (s, 1H), 7.99-7.97 (t, 2H), 7.63-7.61 (t, 1H), 7.38-7.32 (m, 2H), 7.25-7.19 (m, 3H), 7.12-7.10 (m, 2H), 7.02 (s, 1H), 2.87-2.84 (m, 1H), 2.45-2.32 (m, 2H), 2.19-2.07 (m, 3H), 1.96-1.85 (m, 3H), 1.58-1.50 (m, 2H), 0.90 (s, 3H), 0.62 (s, 3H).

The stereochemistry of P1 and P2 were assigned arbitrarily.

Example 10a

N-(6-(1-isopropyl-1H-pyrazol-5-yl)-5-(3-((1R,3R)-3-(trifluoromethoxy)cyclopentyl)phenyl)pyrazin-2-yl)benzenesulfonamide

P1

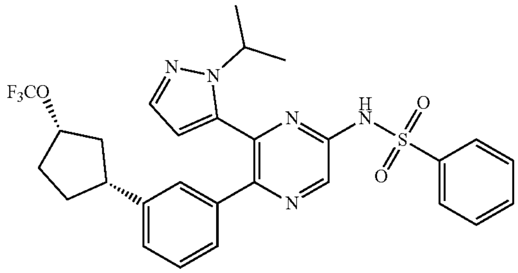

Example 10b

N-(6-(1-isopropyl-1H-pyrazol-5-yl)-5-(3-((1R,3R)-3-(trifluoromethoxy)cyclopentyl)phenyl)pyrazin-2-yl)benzenesulfonamide

P2

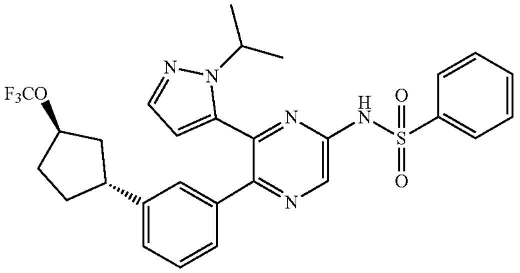

Synthetic Scheme

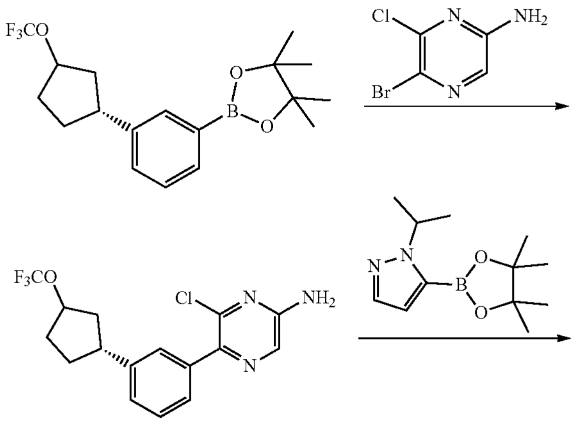

-continued

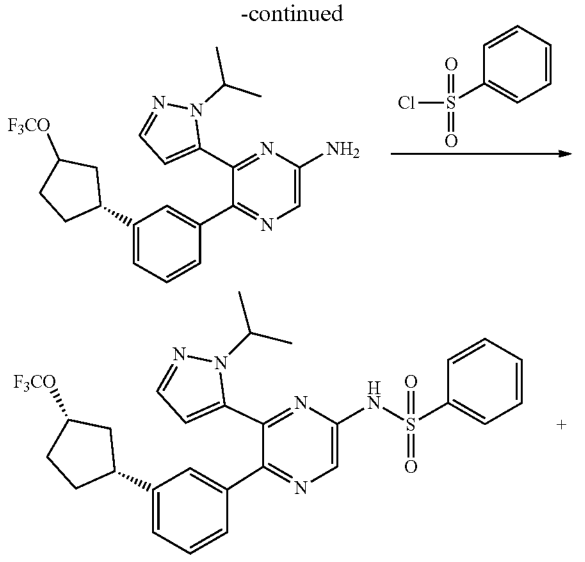

P1

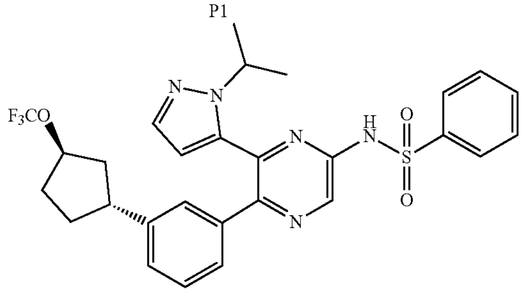

P2

Step 1

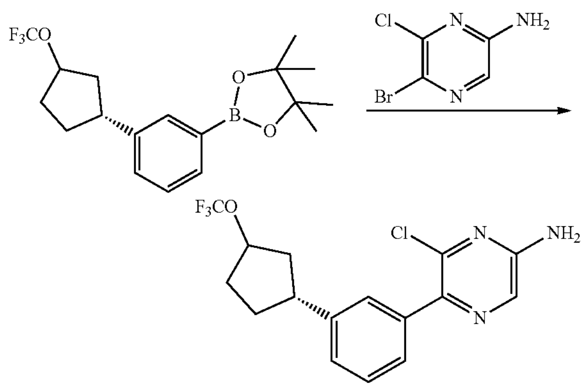

To a solution of 4,4,5,5-tetramethyl-2-(3-((1R)-3-(trifluoromethoxy)cyclopentyl)phenyl)-1,3,2-dioxaborolane (299 mg, 0.84 mmol) in toluene (8.0 mL), ethanol (4.0 mL), water (2.0 mL) was added 5-bromo-6-chloro-pyrazin-2-amine (146 mg, 0.7 mmol), Sodium carbonate (223 mg, 2.1 mmol) and $Pd(PPh_3)_4$ (81 mg, cat.), the resulting mixture was stirred at 90° C. for 12 hours under argon. After that the reaction mixture was added water (60 mL), extracted with ethyl acetate (100 mL×3), washed with brine (60 mL), dried over anhydrous sodium sulfate and filtered. The filtrate was concentrated and purified by silica gel column chromatography on silica gel (PE/EA=1/1) to give 6-chloro-5-(3-((1R)-3-(trifluoromethoxy)cyclopentyl)phenyl)pyrazin-2-amine (245 mg, 97.8%) as yellow solid.

LCMS: LC retention time 2.22 min. MS (ESI) m/z 358 $[M+H]^+$.

Step 2

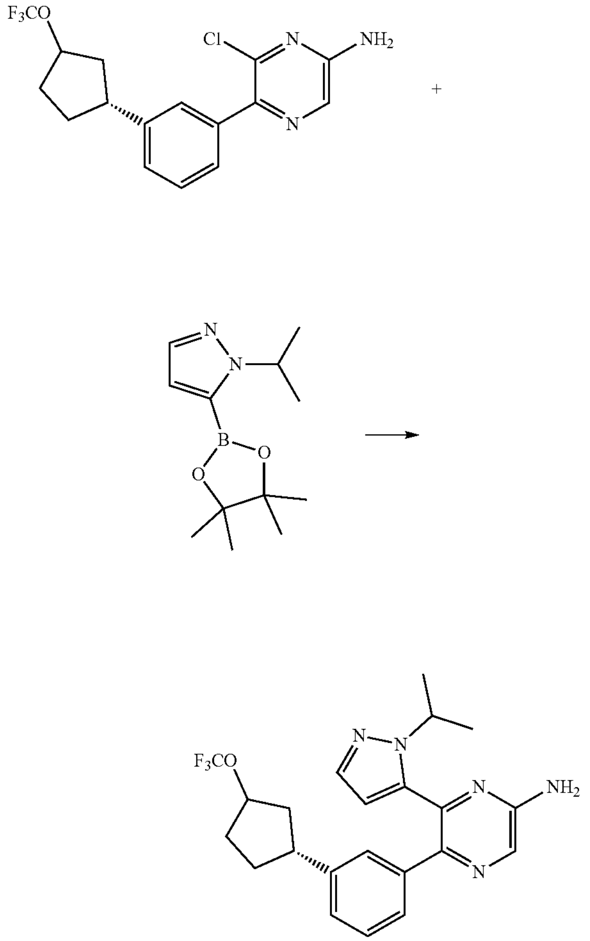

To a solution of 6-chloro-5-(3-((1R)-3-(trifluoromethoxy)cyclopentyl)phenyl)pyrazin-2-amine (190 mg, 0.53 mmol) in N,N-Dimethylformamide (1.50 mL), water (0.250 mL) was added 1-isopropyl-5-(4,4,5,5-tetramethyl-1,3,2-dioxaborolan-2-yl)pyrazole (163 mg, 0.69 mmol), Cesium carbonate (519 mg, 1.59 mmol) and 1,1'-Bis(diphenylphosphino)ferrocene-palladium(II)dichloride dichloromethane complex (43.3 mg, cat.), the resulting mixture was stirred at 120° C. for 3 hours by microwave. To the reaction mixture was added water (40 mL), extracted with ethyl acetate (50 mL×3), washed with brine (40 mL), dried over anhydrous sodium sulfate and filtered. The filtrate was concentrated and purified by silica gel column chromatography on silica gel (PE/EA=2/1) to give 6-(1-isopropyl-1H-pyrazol-5-yl)-5-(3-((1R)-3-(trifluoromethoxy)cyclopentyl)phenyl)pyrazin-2-amine (62 mg, 27.1%) as yellow solid.

LCMS: LC retention time 2.16 min. MS (ESI) m/z 432 $[M+H]^+$.

Step 3

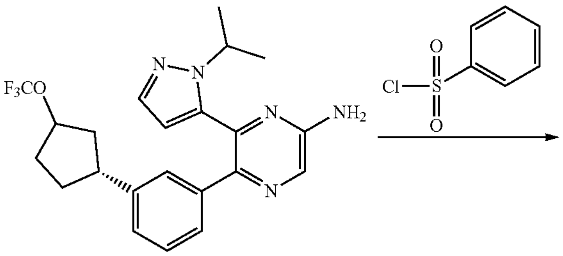

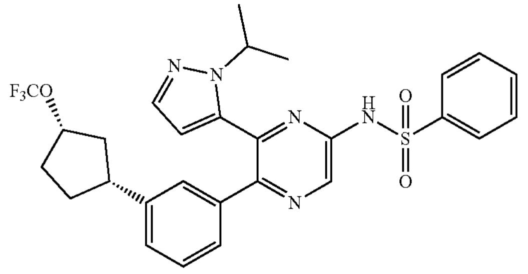

+

P1

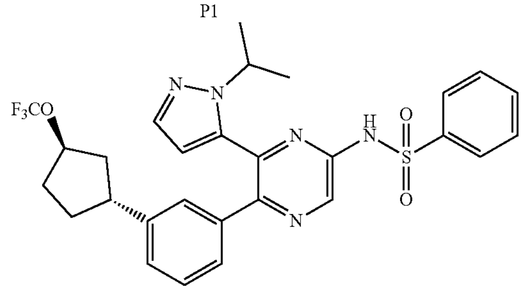

P2

A mixture of 6-(1-isopropyl-1H-pyrazol-5-yl)-5-(3-((1R)-3-(trifluoromethoxy) cyclopentyl)phenyl)pyrazin-2-amine (80 mg, 0.185 mmol) and benzenesulfonyl chloride (131 mg, 0.742 mmol) in pyridine (2.0 mL) was stirred at room temperature overnight. After that the reaction mixture was dried by nitrogen and added sodium bicarbonate (30 mL), ethyl acetate (30 mL), the mixture was stirred at room temperature until benzenesulfonyl chloride was consumed. After that the reaction mixture was extracted with ethyl acetate (50 mL×3), washed with brine (30 mL), dried over anhydrous sodium sulfate and filtered. The filtrate was concentrated and purified by prep-HPLC to give N-(6-(1-isopropyl-1H-pyrazol-5-yl)-5-(3-((1R,3S)-3-(trifluoromethoxy)cyclopentyl)phenyl) pyrazin-2-yl)benzenesulfonamide (P1) (17.9 mg), N-(6-(1-isopropyl-1H-pyrazol-5-yl)-5-(3-((1R,3R)-3-(trifluoromethoxy)cyclopentyl)phenyl) pyrazin-2-yl)benzenesulfonamide (P2) (20.9 mg) as white solids.

P1: LCMS: LC retention time 2.29 min. MS (ESI) m/z 572 $[M+H]^+$.

$^1$H NMR (400 MHz, chloroform-d) δ 8.79 (s, 1H), 8.00 (d, J=7.2 Hz, 2H), 7.63 (t, J=15.2, 7.2 Hz, 1H), 7.55-7.50 (m, 3H), 7.25 (s, 3H), 7.22-7.19 (m, 1H), 7.15 (s, 1H), 6.16 (d, J=2.0 Hz, 1H), 4.75 (s, 1H), 4.10-4.04 (m, 1H), 2.96-2.92 (m, 1H), 2.49-2.42 (m, 1H), 2.03-1.95 (m, 3H), 1.78-1.73 (m, 1H), 1.08 (d, J=6.8 Hz, 6H).

P2: LCMS: LC retention time 2.30 min. MS (ESI) m/z 572 $[M+H]^+$.

$^1$H NMR (400 MHz, chloroform-d) δ 8.78 (s, 1H), 8.00 (d, J=8.8 Hz, 2H), 7.63 (t, J=14.8, 7.2 Hz, 1H), 7.56-7.51 (m, 3H), 7.25 (s, 2H), 7.15 (m, 1H), 7.09 (s, 1H), 6.16 (d, J=1.6 Hz, 1H), 4.81 (s, 1H), 4.10-4.06 (m, 1H), 3.27-3.23 (m, 1H), 2.17-2.14 (m, 2H), 1.97 (m, 1H), 1.71-1.65 (m, 1H), 1.43 (m, 2H), 1.08 (d, J=6.4 Hz, 6H).

The stereochemistry of P1 and P2 were assigned arbitrarily.

Example 11

N-(6-(1-isopropyl-1H-pyrazol-5-yl)-5-(3-((1R,3R)-3-(trifluoromethoxy)cyclopentyl)phenyl)pyrazin-2-yl)-1,3-dimethyl-1H-pyrazole-4-sulfonamide Chiral

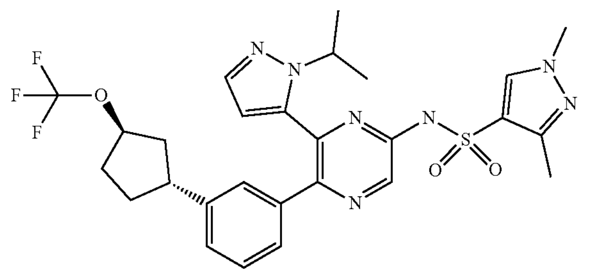

Example 11 was synthesized by essentially the same protocol as Example 10 except only P2 was obtained.

LCMS: LC retention time 2.29 min. MS (ESI) m/z 590 $[M+H]^+$.

$^1$H NMR (400 MHz, chloroform-d) δ 8.70 (s, 1H), 7.91 (s, 1H), 7.58 (d, J=30.4 Hz, 2H), 7.28 (s, 1H), 7.18 (t, J=9.2, 4.8 Hz, 1H), 7.10 (s, 1H), 6.23 (s, 1H), 4.82 (s, 1H), 4.15-4.12 (m, 1 H), 3.82 (s, 3H), 3.26-3.24 (m, 1H), 2.49 (s, 3H), 2.27-2.21 (m, 1H), 2.19-2.12 (m, 2H), 2.05-1.95 (m, 1H), 1.73-1.65 (m, 1H), 1.48-1.43 (m, 1H), 1.11 (d, J=6.8 Hz, 6H).

Example 12

6-chloro-N-(5-(4-chloro-3-(neopentyloxy)phenyl)-6-(4-(trifluoromethyl)phenyl)pyridin-2-yl)pyridine-2-sulfonamide

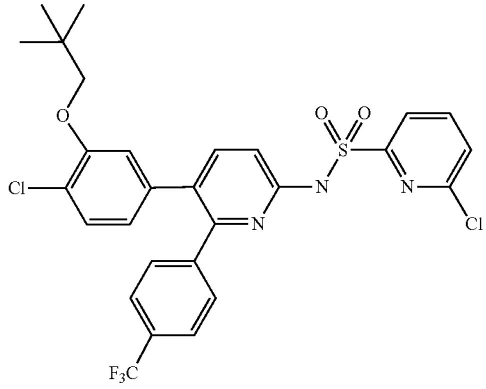

Synthetic Scheme

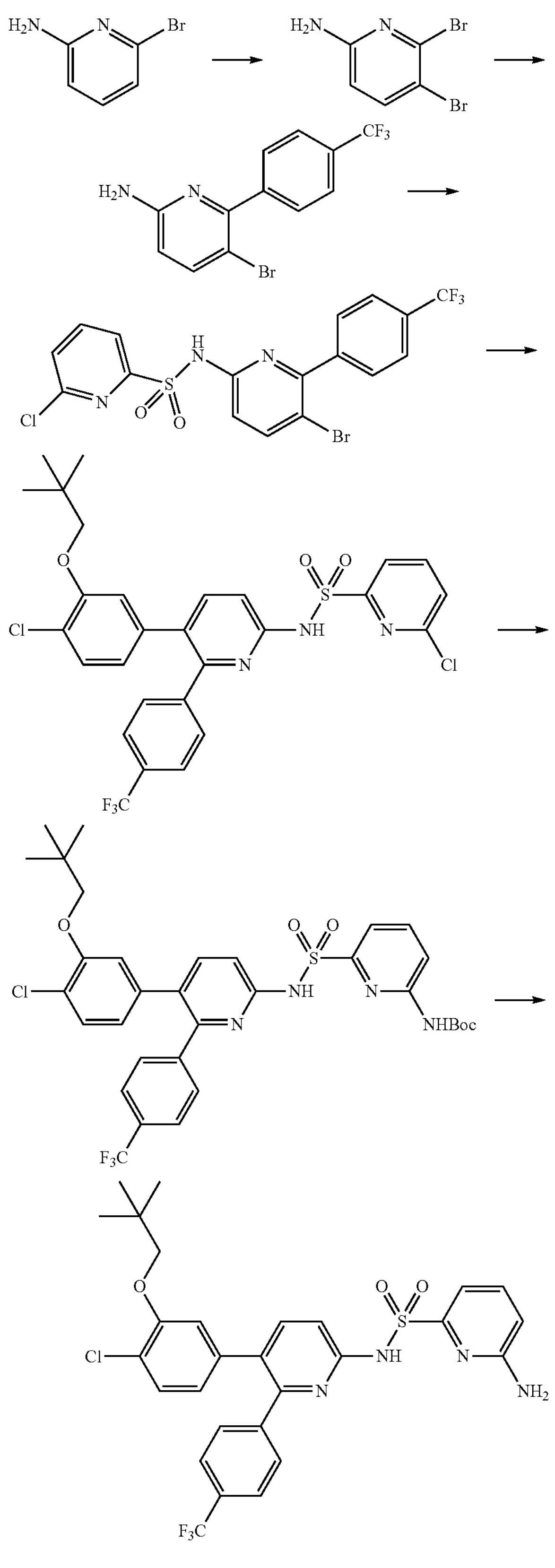

Step 1

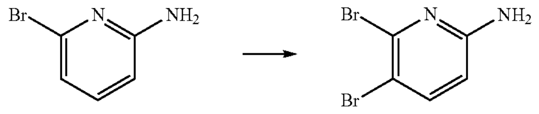 [SMILES: Nc1cccc(Br)n1 ; Nc1ccc(Br)c(Br)n1]

The mixture of 6-bromopyridin-2-amine (3.0 g, 0.017 mmol) and NBS (3.09 mg, 0.017 mmol) in DMF (10.0 mL) was stirred at 25° C. for 16 h. The mixture was then poured into $H_2O$ (80 mL) and extracted with EA (3×50 mL). After that, the organic layers were combined, dried over anhydrous sodium sulfate, filtered, and concentrated in vacuo. The mixture was purified by SGC (PE/EA=100/1) to afford product 5,6-dibromopyridin-2-amine (3.9 g, 89.3%) as a brown solid.

LC retention time 1.80 min., MS (ESI) m/z 252 $[M+H]^+$.

Step 2

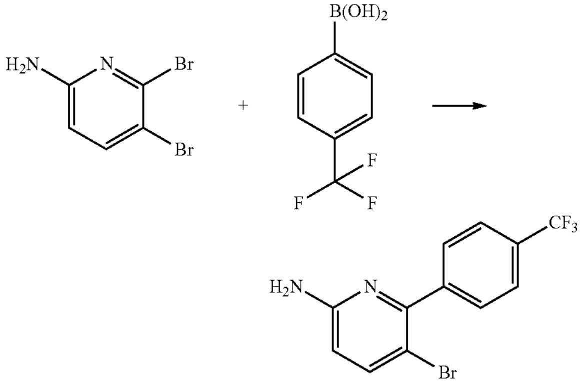

To a solution of 5,6-dibromopyridin-2-amine (2 g, 7.94 mmol) in toluene (40 mL) and methanol (4 ml) was added (4-(trifluoromethyl)phenyl)boronic acid (1.11 g, 7.94 mmol), $Na_2CO_3$ (5.03 g, 36.4 mmol) and $Pd_3(PPh_3)_4$. The mixture was stirred at 55° C. for overnight. The resulting mixture was poured into water (30 mL) and extracted with ethyl acetate (3×20 mL). The organic layers were combined, washed with brine, dried and concentrated. The residue was purified by silica gel chromatography (PE/EA=5/1) to afford crude product 5-bromo-6-(4-(trifluoromethyl)phenyl)pyridin-2-amine (2.1 g, 84%) as a light white solid.

LCMS Purity: 92.93%; MS (ESI) m/z 316 $[M+H]^+$.

Step 3

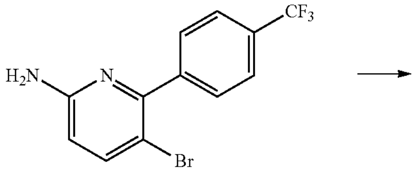

-continued

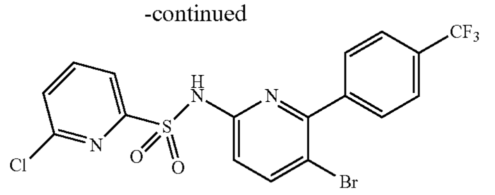

To a solution of 5-bromo-6-(4-(trifluoromethyl)phenyl) pyridin-2-amine (250 mg, 0.79 mmol) in pyridine (3 mL) was added 6-chloropyridine-2-sulfonyl chloride (167 mg, 0.79 mmol), the mixture was stirred at 100° C. for 2 h. The reaction was cooled to 0° C. and quenched with brine (5 ml). The filtrate was diluted with ethyl acetate (100 mL), washed with brine (50 mL×2), dried over sodium sulfate, and concentrated. The filtrate was concentrated to purified by SGC (PE/EA=3/1) to afford N-(5-bromo-6-(4-(trifluoromethyl)phenyl)pyridin-2-yl)-6-chloropyridine-2-sulfonamide (300 mg, 77%) as light brown oil.

LCMS Purity: 73%; MS (ESI) m/z 491 $[M+H]^+$.

Step 4

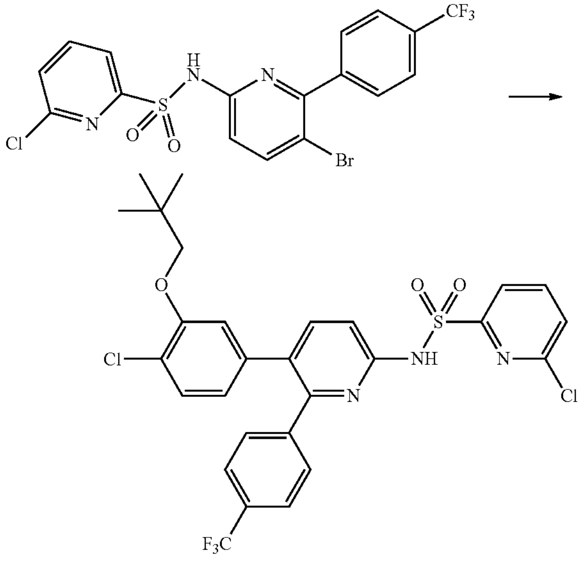

To a solution of N-(5-bromo-6-(4-(trifluoromethyl)phenyl)pyridin-2-yl)-6-chloropyridine-2-sulfonamide (300 mg, 0.61 mmol) in dioxane (2 mL, v/v=2/1) was added (4-chloro-3-(neopentyloxy)phenyl)boronic acid (148 mg, 0.61 mmol), $PdCl_2$(dppf) (22 mg, 0.31 mmol), $Cs_2CO_3$ (398 mg, 1.22 mmol), the mixture was stirred at 90° C. overnight. The reaction was cooled to 0° C. and quenched with brine (5 ml). The filtrate was diluted with ethyl acetate (100 mL), washed with brine (50 mL×2), dried over sodium sulfate, and concentrated to afford 6-chloro-N-(5-(4-chloro-3-(neopentyloxy)phenyl)-6-(4-(trifluoromethyl)phenyl)pyridin-2-yl)pyridine-2-sulfonamide (250 mg, 67%) as light brown oil.

LCMS (214 nm & 254 nm) purity>99%; retention time 2.16 min; MS (ESI) m/z 610 $[M+H]^+$.

$^1$H NMR (400 MHz, $CD_3OD$) δ 8.10 (d, J=7.6 Hz, 1H), 7.98 (dd, J=8.0 Hz & 7.6 Hz, 1H), 7.85 (d, J=8.8 Hz, 1H), 7.64 (d, J=8.0 Hz, 1H), 7.58 (d, J=8.0 Hz, 2H), 7.36-7.28 (m, 4H), 6.80 (dd, J=2.0 Hz & 8.4 Hz, 1H), 6.59 (d, J=2.0 Hz, 1H), 3.25 (s, 2H), 0.97 (m, 9H) ppm.

Example 13

6-amino-N-(5-(4-chloro-3-(neopentyloxy)phenyl)-6-(4-(trifluoromethyl)phenyl)pyridin-2-yl)pyridine-2-sulfonamide

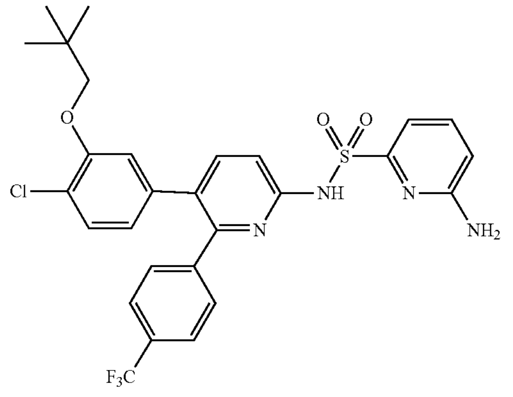 [SMILES: CC(C)(C)COc1cc(-c2ccc(NS(=O)(=O)c3cccc(N)n3)nc2-c2ccc(C(F)(F)F)cc2)ccc1Cl]

Synthesis Scheme

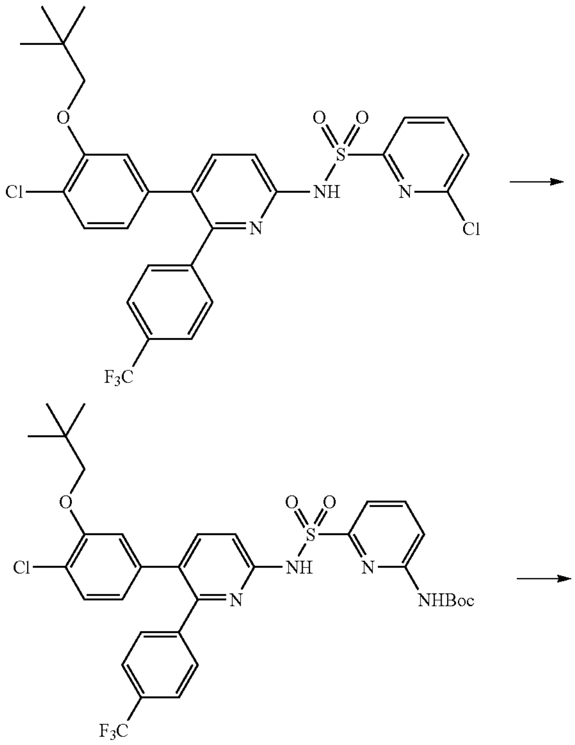

-continued

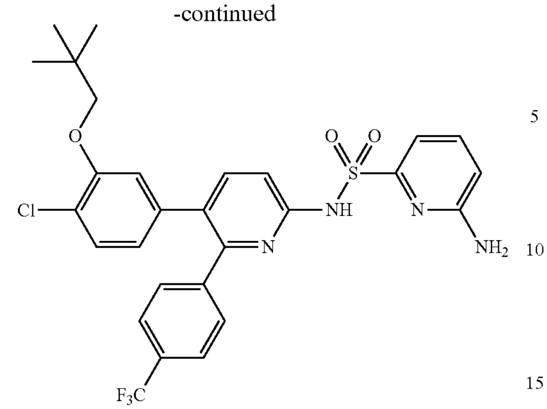

Step 1

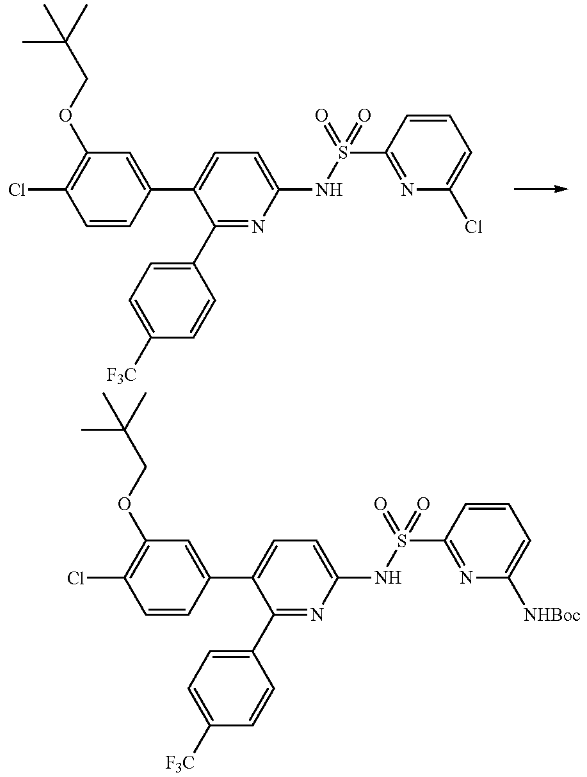

To a solution of 6-chloro-N-(5-(4-chloro-3-(neopentyloxy)phenyl)-6-(4-(trifluoromethyl)phenyl)pyridin-2-yl) pyridine-2-sulfonamide (230 mg, 0.38 mmol) in dioxane (4 mL) was added $BocNH_2$ (44 mg, 0.38 mmol), $PdCl_2$(dppf) (17 mg, 0.02 mmol), X-phos (17 mg, 0.04 mmol), the mixture was stirred at 90° C. for 8 h. The reaction was cooled to 0° C. and quenched with brine (5 ml). The filtrate was diluted with ethyl acetate (100 mL), washed with brine (50 mL×2), dried over sodium sulfate, and concentrated. The filtrate was concentrated to purified by SGC (PE/EA=2/1) to afford tert-butyl (6-(N-(5-(4-chloro-3-(neopentyloxy)phenyl)-6-(4-(trifluoromethyl) phenyl)pyridin-2-yl)sulfamoyl) pyridin-2-yl)carbamate (150 mg, 53%) as light brown solid.

LCMS Purity: 84%; MS (ESI) m/z 691 $[M+H]^+$.

Step 2

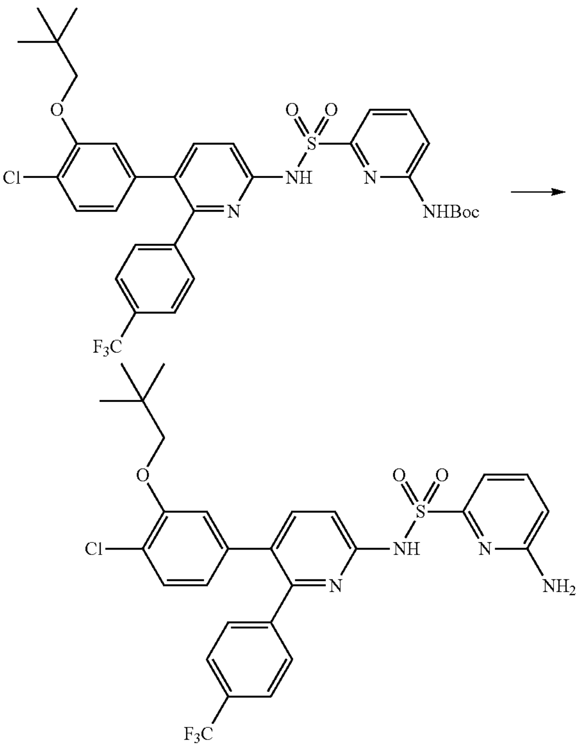

To a solution of tert-butyl (6-(N-(5-(4-chloro-3-(neopentyloxy)phenyl)-6-(4-(trifluoromethyl)phenyl)pyridin-2-yl) sulfamoyl)pyridin-2-yl)carbamate (140 mg, 0.2 mmol) in 4M HCl in dioxane (2 mL) was stirred at rt for 8 h. Then removed the solvent and purified by Prep-HPLC to afford 6-amino-N-(5-(4-chloro-3-(neopentyloxy)phenyl)-6-(4-(trifluoromethyl)phenyl) pyridin-2-yl)pyridine-2-sulfonamide (11.4 mg, 9%) as white solid.

LCMS Purity: >99% (214 nm & 254 nm); retention time 1.96 min; MS (ESI) m/z 591 $[M+H]^+$.

$^1H$ NMR (400 MHz, $CDCl_3$) δ 7.70 (d, J=8.4 Hz, 1H), 7.59-7.55 (m, 3H), 7.46-7.43 (m, 3H), 7.41 (d, J=8.4 Hz, 1H), 7.28 (d, J=6.8 Hz, 1H), 6.66 (dd, J=2.0 Hz & 8 Hz, 1H), 6.61 (d, J=8.0 Hz, 1H), 6.51 (d, J=1.6 Hz, 1H), 4.72 (s, 2H), 3.28 (s, 3H), 1.00 (m, 9H) ppm.

Example 14

N-(5-(4-chloro-3-(neopentyloxy)phenyl)-6-(4-(trifluoromethyl)phenyl)pyridin-2-yl)benzenesulfonamide

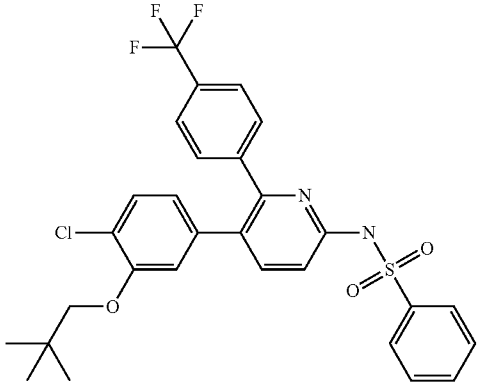

Example 14 was synthesized similarly as Example 12.

LCMS Purity: 99%; MS (ESI) m/z 574 $[M+H]^+$.

$^1$H NMR (400 MHz, $CDCl_3$) δ 7.97-7.95 (m, 2H) 7.85-7.82 (m, 1H), 7.69-7.64 (m, 3H), 7.60-7.57 (m, 2H), 7.35-7.29 (m, 3H), 7.12-7.10 (m, 1H), 6.69-6.73 (m, 2H), 2.34-2.30 (m, 2H), 0.97 (s, 9H) ppm.

Example 15

N-(5-(3-(3,3-dimethylbutoxy)phenyl)-6-(2,6-dimethylphenyl)pyridin-2-yl)benzenesulfonamide

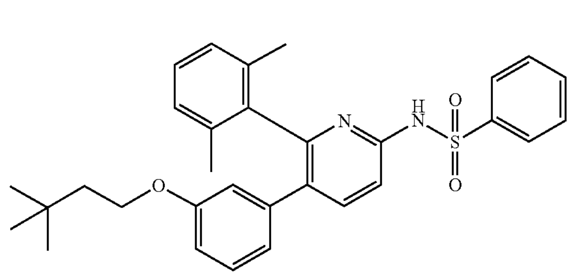 [SMILES: Cc1cccc(C)c1-c1nc(NS(=O)(=O)c2ccccc2)ccc1-c1cccc(OCCC(C)(C)C)c1]

Synthetic Scheme

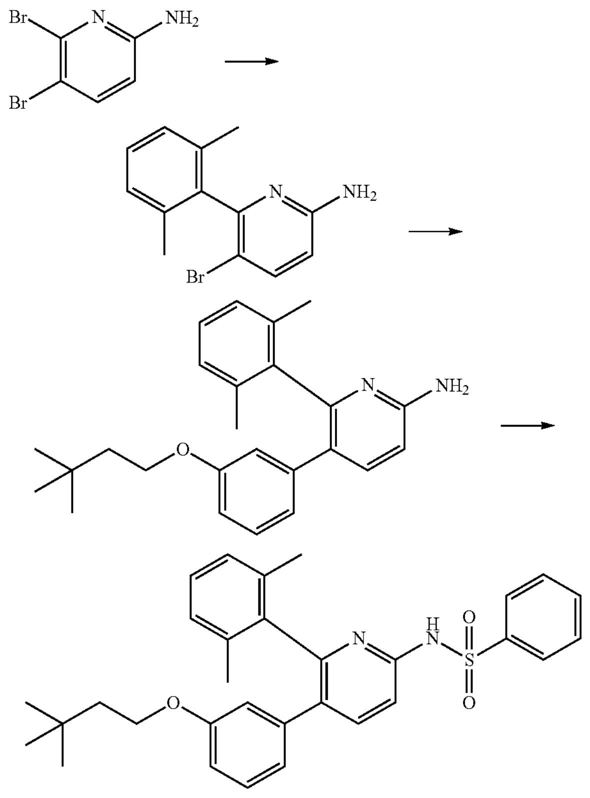

Step 1

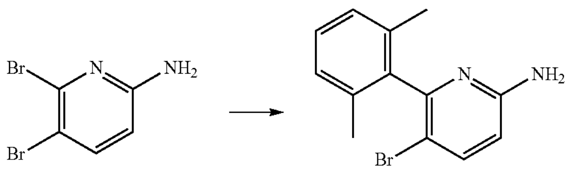 [SMILES: Nc1ccc(Br)c(Br)n1 ; Cc1cccc(C)c1-c1nc(N)ccc1Br]

A mixture of (2,6-dimethylphenyl)boronic acid (119 mg, 0.79 mmol), $Na_2CO_3$ (168 mg, 0.168 mmol), $Pd(PPh_3)_4$ (91 mg, 0.079 μmol) and 5,6-dibromopyridin-2-amine (200 mg, 0.79 mmol) in DMF/$H_2O$ (4/1 mL) was stirred at 110° C. in microwave for 16 h. The reaction mixture was diluted with water (5 mL) and extracted with ethyl acetate (3×8 mL). The organic layers were combined, dried over anhydrous sodium sulfate and concentrated in vacuo. The mixture was purified by SGC (PE/EA=4/1) to afford product 5-bromo-6-(2,6-dimethylphenyl)pyridin-2-amine (110 mg, 20%) as a brown oil.

LC retention time 1.76 min. MS (ESI) m/z 276 $[M+H]^+$.

Step 2

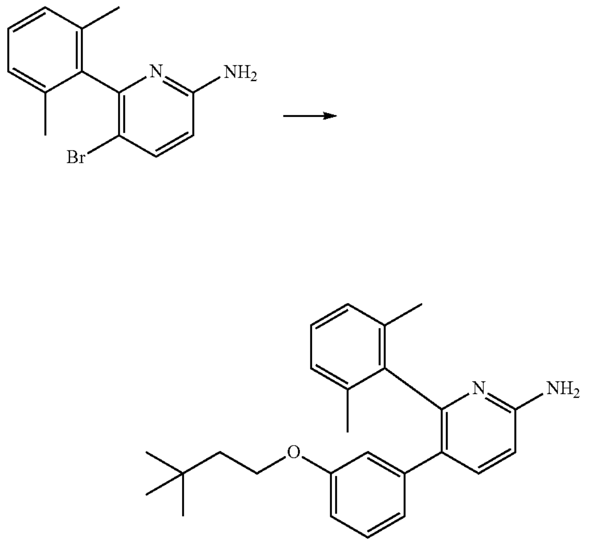

A mixture of 3-(3,3-dimethylbutoxy)phenyl]boronic acid (96.2 mg, 0.43 mmol), $Na_2CO_3$ (138 mg, 1.2 mmol), $Pd(PPh_3)_4$ (50 mg, 0.1 mmol) and 5-bromo-6-(2,6-dimethylphenyl)pyridin-2-amine (120 mg, 0.43 mmol) in toluene/EtOH/$H_2O$ (4/2/1 10 mL) was stirred at 110° C. for 16 h. The reaction mixture was diluted with water (5 mL) and extracted with ethyl acetate (3×8 mL). The organic layers were combined, dried over anhydrous sodium sulfate and concentrated in vacuo. The mixture was purified by SGC (PE/EA=4/1) to afford product 5-(3-(3,3-dimethylbutoxy)phenyl)-6-(2,6-dimethylphenyl)pyridin-2-amine (30 mg, 18.5%) as a yellow oil.

LC retention time 2.01 min. MS (ESI) m/z 375 $[M+H]^+$.

Step 3

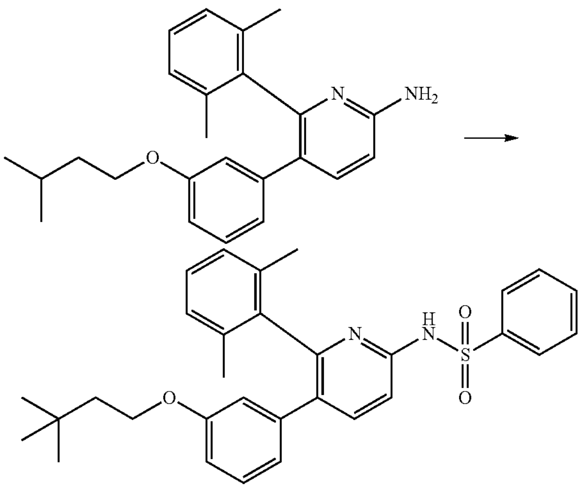

To mixture of 5-(3-(3,3-dimethylbutoxy)phenyl)-6-(2,6-dimethylphenyl)pyridin-2-amine (30 mg, 8.01e mmol) and benzenesulfonyl chloride (42.4 mg, 0.24 mmol) in pyridine (3 mL) was stirred at 25° C. for 16 h. The reaction mixture was diluted with water (5 mL) and extracted with ethyl acetate (3×8 mL). The organic layers were combined, dried over anhydrous sodium sulfate and concentrated in vacuo. The mixture was purified by prep-HPLC to afford product N-(5-(3-(3,3-dimethylbutoxy)phenyl)-6-(2,6-dimethylphenyl)pyridin-2-yl)benzenesulfonamide (13.5 mg, 32.7%) as a white solid.

LCMS: LC retention time 2.44 min. MS (ESI) m/z 515 $[M+H]^+$.

$^1H$ NMR (400 MHz, chloroform-d) δ 7.89-7.90 (m, 1H), 7.79-7.81 (m, 1H), 7.44-7.55 (m, 3H), 7.33-7.35 (m, 1H), 7.11-7.15 (m, 2H), 6.97-6.99 (m, 2H), 6.64-6.73 (m, 2H), 6.41-6.42 (m, 1H), 3.63 (t, J=8.0 Hz, 2H), 1.86 (s, 6H), 1.60 (t, J=4.0 Hz, 2H), 0.93 (s, 9H).

Example 16

3-amino-N-(5-(3-(3,3-dimethylbutoxy)phenyl)-6-(2-isopropylphenyl)pyridin-2-yl)benzenesulfonamide

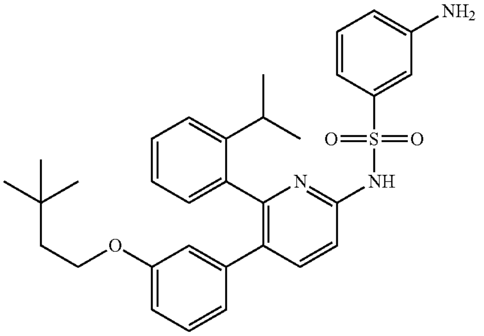 [SMILES: CC(C)c1ccccc1-c1nc(NS(=O)(=O)c2cccc(N)c2)ccc1-c1cccc(OCCC(C)(C)C)c1]

Synthetic Scheme

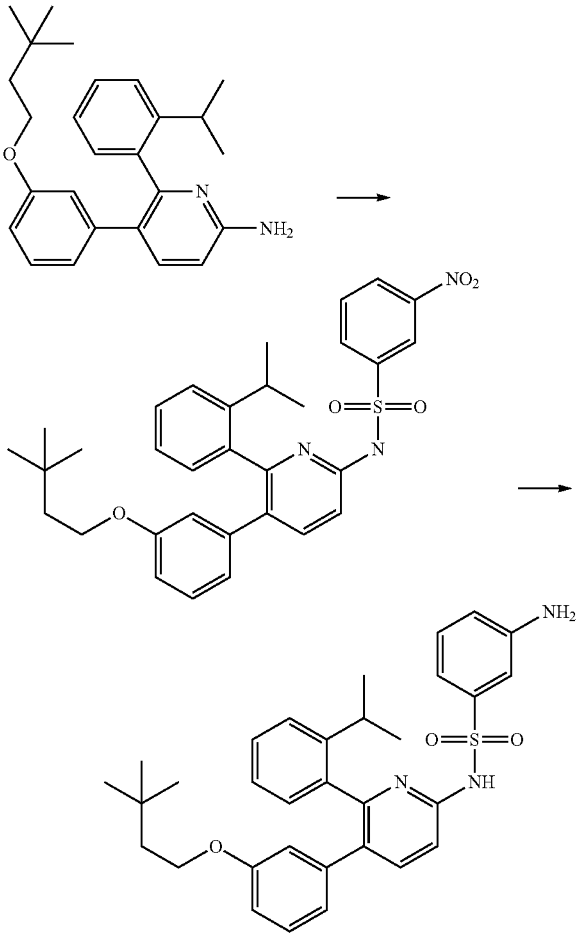

Step 1

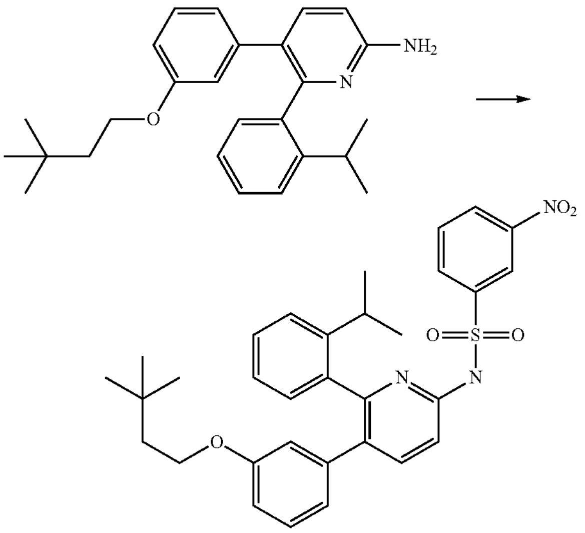

A reaction mixture of 5-(3-(3,3-dimethylbutoxy)phenyl)-6-(2-isopropylphenyl)pyridin-2-amine, synthesized similarly as in Example 15, (120 mg, 0.158 mmol) and NaOH (63.3 mg, 1.58 mmol) in MeOH (10 mL) at room temperature. Then the reaction mixture was stirred at room temperature for 2 h. Concentrated in vacuo. 30 mL of water was added, then extracted by EA (30 mL×3), dried over $Na_2SO_4$, concentrated in vacuo to afford the desired product 3-(3-(3,3-dimethylbutoxy)phenyl)-2-(2-isopropylphenyl)-6-(((3-nitrophenyl)sulfonyl)-12-azaneyl)pyridine (77 mg, 0.134 mmol, 84.9% yield) as yellow oil.

LCMS: LC retention time 2.562 min; MS (ESI) m/z 574 $[M+H]^+$.

Step 2

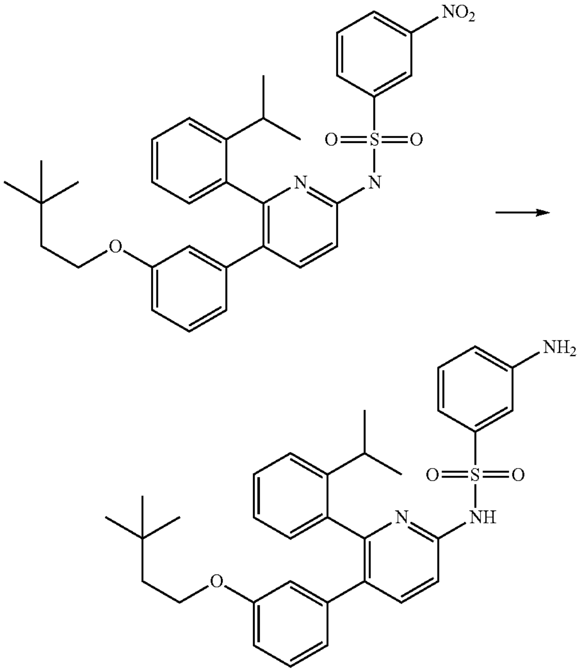

To a mixture of 3-(3-(3,3-dimethylbutoxy)phenyl)-2-(2-isopropylphenyl)-6-(((3-nitrophenyl)sulfonyl)-12-azaneyl) pyridine (50 mg, 0.087 mmol) and $NH_4Cl$ (46.6 mg, 0.87 mmol) in MeOH (10 mL) was added Fe (24.4 mg, 0.436 mmol) at room temperature. Then the reaction mixture was stirred at 50° C. for 2 h, allowed to cool to room temperature. The reaction mixture was extracted with EA (30 mL×3), washed with water (30 mL×2), dried over $Na_2SO_4$, filtered and concentrated, purified by prep-HPLC to afford the desired product 3-amino-N-(5-(3-(3,3-dimethylbutoxy)phenyl)-6-(2-isopropylphenyl)pyridin-2-yl)benzenesulfonamide (19.4 mg, yield: 40.9%) as grey solid.

LCMS: LC retention time 2.359 min; MS (ESI) m/z 544 $[M+H]^+$.

$^1$H NMR (400 MHz, chloroform-d) δ 7.81-7.75 (m, 1H), 7.3-7.28 (m, 3H), 7.39-7.35 (m, 3H), 7.26-7.24 (m, 3H), 7.18-7.16 (m, 1H), 6.84-6.83 (m, 2H), 6.7-6.4 (s, 1H), 3.88-3.65 (s, 1H), 3.65-3.63 (s, 2H), 2.64-2.58 (m, 1H), 1.6-1.58 (m, 9H), 1.01-0.94 (s, 9H).

Example 17

3-amino-N-(5-(4-chloro-3-(neopentyloxy)phenyl)-6-(4-(trifluoromethyl)phenyl)pyridin-2-yl)benzenesulfonamide

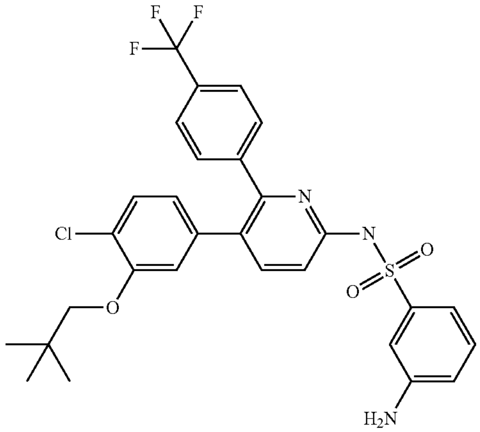

Example 17 was synthesized similarly as in Example 15.

Purity: >99% LCMS (214 nm & 254 nm); retention time 1.96 min; 591 $(M+H^+)$.

$^1$H NMR (400 MHz, $CDCl_3$) δ 7.70 (d, J=8.4 Hz, 1H), 7.59-7.55 (m, 3H), 7.46-7.43 (m, 3H), 7.41 (d, J=8.4 Hz, 1H), 7.28 (d, J=6.8 Hz, 1H), 6.66 (dd, J=2.0 Hz & 8 Hz, 1H), 6.61 (d, J=8.0 Hz, 1H), 6.51 (d, J=1.6 Hz, 1H), 4.72 (s, 2H), 3.28 (s, 3H), 1.00 (m, 9H) ppm.

Example 18

N-(5-(4-chloro-3-(neopentyloxy)phenyl)-6-(4-(trifluoromethyl)phenyl)pyridin-2-yl)-3-(methylsulfonamido)benzenesulfonamide

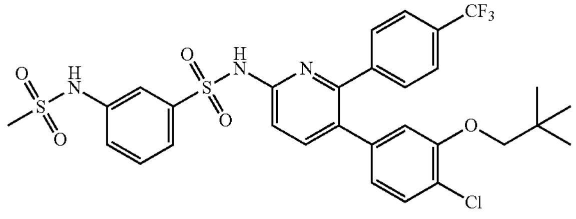 [SMILES: CC(C)(C)COc1cc(-c2ccc(NS(=O)(=O)c3cccc(NS(C)(=O)=O)c3)nc2-c2ccc(C(F)(F)F)cc2)ccc1Cl]

Synthesis Scheme

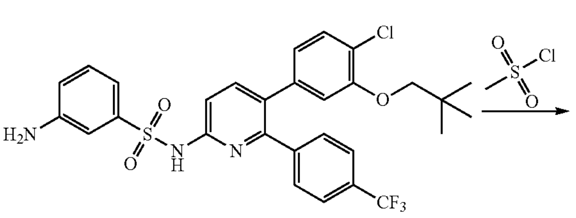

-continued

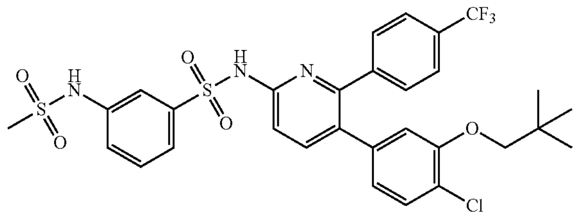

To the mixture of 3-amino-N-(5-(4-chloro-3-(neopentyloxy)phenyl)-6-(4-(trifluoromethyl)phenyl)pyridin-2-yl) benzenesulfonamide, obtained by a similar protocol as for Example 16, (210 mg, 0.34 mmol) and DMAP (78 mg, 0.62 mmol) in pyridine (5.0 mL) was added methanesulfonyl chloride (0.1 mL, 4.30 mmol) at 0° C. The resultant mixture was stirred at 50° C. for overnight. The mixture was diluted with $H_2O$ (10 mL), and extracted with extracted (3×10.0 mL). The combined organic phases were dried over anhydrous sodium sulfate, filtered, and concentrated in vacuo, which was purified by Pre-TLC (PE/EA=5/1) to give title product N-(5-(4-chloro-3-(neopentyloxy)phenyl)-6-(4-(trifluoromethyl)phenyl)pyridin-2-yl)-3-(methylsulfonamido) benzenesulfonamide (15 mg, 30%) as a white solid.

LCMS Purity: 93%; MS (ESI) m/z 667 $[M+H]^+$.

$^1$H NMR (400 MHz, $CDCl_3$) δ 7.79-7.73 (m, 3H), 7.56-7.54 (m, 2H), 7.51-7.36 (m, 5H), 7.29 (m, 2H), 7.27 (m, 1H), 6.66-6.64 (m, 1H), 6.51-6.50 (m, 1H) ppm.

Example 19

N-(6-(4-chloro-2-isopropylphenyl)-5-(3-(trifluoromethoxy)phenyl)pyridin-2-yl)benzenesulfonamide

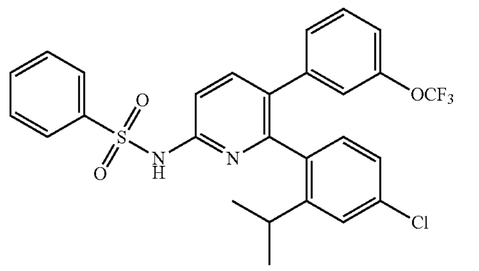 [SMILES: CC(C)c1cc(Cl)ccc1-c1nc(NS(=O)(=O)c2ccccc2)ccc1-c1cccc(OC(F)(F)F)c1]

Example 19 was synthesized by essentially the same protocol as Example 15.

LCMS: LC retention time 1.98 min. MS (ESI) m/z 547 $[M+H]^+$ $^1$H NMR (400 MHz, chloroform-d) δ 7.93 (d, J=8.0 Hz, 2H), 7.71 (d, J=8.0 Hz, 1H), 7.58 (t, J=8.0 Hz, 1H), 7.51-7.41 (m, 3H), 7.23 (t, J=8.0 Hz, 1H), 7.17 (d, J=4.0 Hz, 1H), 7.11 (dd, J=8.0, 4.0 Hz, 1H), 7.05 (d, J=8.0 Hz, 1H), 6.95 (d, J=8.0 Hz, 2H), 6.85 (s, 1H), 2.47 (dt, J=12.0, 8.0 Hz, 1H), 0.80 (d, J=92.0 Hz, 6H).

Example 20

N-(6-(2,6-dimethylphenyl)-5-(3-(3,3,3-trifluoro-2,2-dimethylpropoxy)phenyl)pyridin-2-yl)-3-((3-hydroxy-3-methylcyclobutyl)aminobenzenesulfonamide

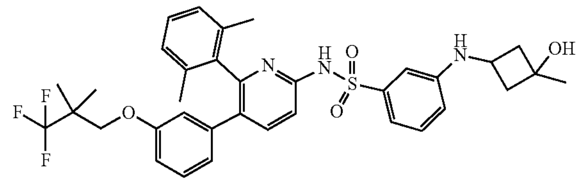 [SMILES: Cc1cccc(C)c1-c1nc(NS(=O)(=O)c2cccc(NC3CC(C)(O)C3)c2)ccc1-c1cccc(OCC(C)(C)C(F)(F)F)c1]

Synthetic Scheme

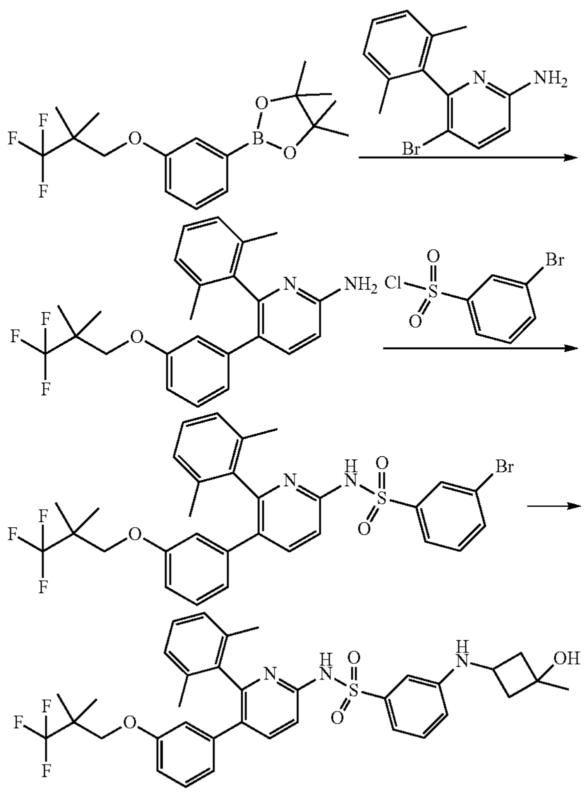

Step 1

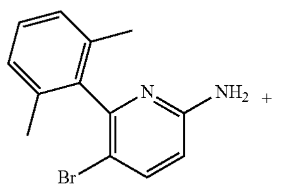

-continued

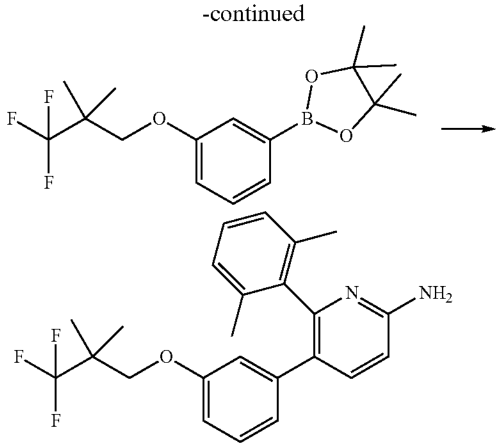

To a solution of 5-bromo-6-(2,6-dimethylphenyl)pyridin-2-amine (870 mg, 3.14 mmol) in toluene/EtOH/$H_2O$ (v/v/v=4/2/1) (17.5 mL), 4,4,5,5-tetramethyl-2-(3-(3,3,3-trifluoro-2,2-dimethylpropoxy)phenyl)-1,3,2-dioxaborolane (1.4 g, 4.08 mmol), $Na_2CO_3$ (998 mg, 9.42 mmol), and $Pd(PPh_3)_4$ (363 mg, 0.314 mmol) was added. The result mixture was reacted under an argon atmosphere at 90° C. for 4 h. The reaction mixture was concentrated, diluted with EtOAc (50 mL), washed with water (50 mL×3). The organics were dried over $Na_2SO_4$, filtered, concentrated and purified by SGC (PE:EA=4:1) to afford 6-(2,6-dimethylphenyl)-5-(3-(3,3,3-trifluoro-2,2-dimethylpropoxy)phenyl)pyridin-2-amine (326 mg, yield: 25.1%) as yellow solid.

LCMS (acidic): LC retention time 2.093, MS (ESI): m/z 415 $[M+H]^+$.

Step 2

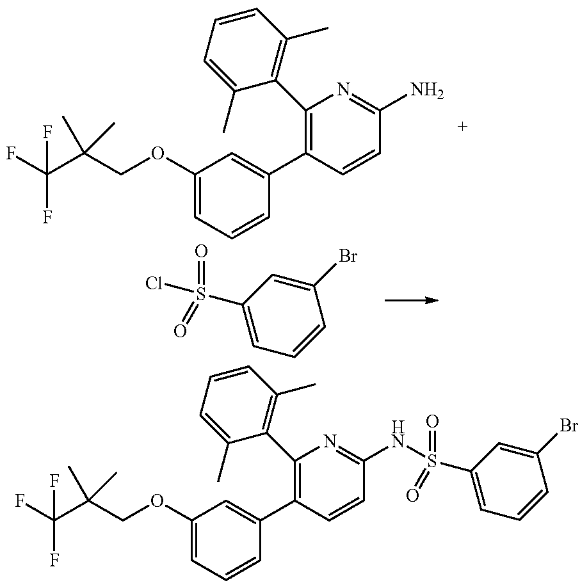

The reaction mixture of 6-(2,6-dimethylphenyl)-5-(3-(3,3,3-trifluoro-2,2-dimethylpropoxy) phenyl)pyridin-2-amine (150 mg, 0.362 mmol) and 3-bromobenzenesulfonyl chloride (277 mg, 1.09 mmol) in pyridine (3 mL) was stirred at room temperature for 3 hours. Diluted with EtOAc (50 mL), washed with brine (50 mL×3). The organics were dried over $Na_2SO_4$, filtered and concentrated to give the crude, which was purified by com-flash (PE:EA=4:1) to afford 3-bromo-N-(6-(2,6-dimethylphenyl)-5-(3-(3,3,3-trifluoro-2,2-dimethylpropoxy)phenyl)pyridin-2-yl)benzenesulfonamide (180 mg, yield: 78.5%) as yellow solid.

LCMS (acidic): LC retention time 2.406, MS (ESI): m/z 635 $[M+H]^+$.

Step 3

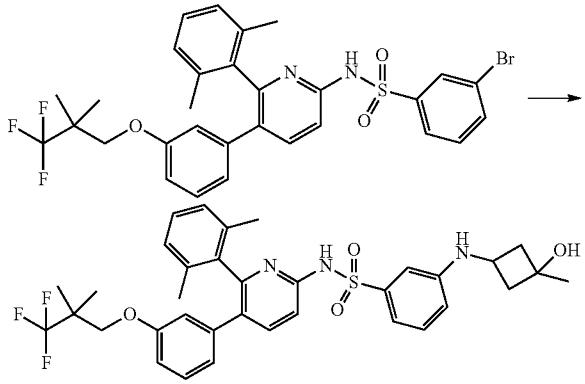

The mixture of 3-bromo-N-(6-(2,6-dimethylphenyl)-5-(3-(3,3,3-trifluoro-2,2-dimethylpropoxy)phenyl)pyridin-2-yl) benzenesulfonamide (160 mg, 0.253 mmol), 3-amino-1-methylcyclobutan-1-ol hydrochloride (52 mg, 0.379 mmol), $K_2CO_3$ (140 mg, 1.01 mmol), L(−)-proline (15 mg, cat.) and copper(I) iodide (15 mg, cat.) was reacted in glovebox at 100° C. overnight. The reaction was diluted with brine (100 mL), extracted with ethyl acetate (50 mL×2). The combined organics concentrated under reduced pressure. The residue was purified by Prep-HPLC to afford the desired compound N-(6-(2,6-dimethylphenyl)-5-(3-(3,3,3-trifluoro-2,2-dimethylpropoxy) phenyl)pyridin-2-yl)-3-((3-hydroxy-3-methylcyclobutyl)amino)benzenesulfonamide (61.1 mg, 37.0%) as yellow solid.

LCMS (acidic): LC retention time 2.240 min. MS (ESI) m/z 654 $[M+H]^+$.

$^1H$ NMR (400 MHz, methanol-$d_4$) δ 7.90 (d, J=9.2 Hz, 1H), 7.42-7.37 (m, 1H), 7.22-7.12 (m, 4H), 7.02-6.99 (m, 3H), 6.83-6.73 (m, 3H), 6.43 (s, 1H), 3.52 (s, 2H), 3.38-3.32 (m, 1H), 2.53-2.48 (m, 2H), 1.95-1.92 (m, 2H), 1.90-1.85 (m, 6H), 1.36-1.31 (m, 3H), 1.18 (s, 6H).

Example 21

1-[6-[[6-(2-ethylphenyl)-5-[3-(2,2,2-trifluoroethoxy) phenyl]-2-pyridyl]sulfamoyl]-2-pyridyl]-3-methyl-piperidine-3-carboxylic acid

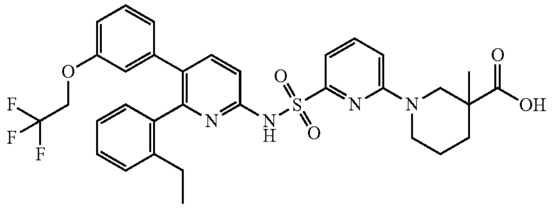 [SMILES: CCc1ccccc1-c1nc(NS(=O)(=O)c2cccc(N3CCCC(C)(C(=O)O)C3)n2)ccc1-c1cccc(OCC(F)(F)F)c1]

Synthetic Scheme

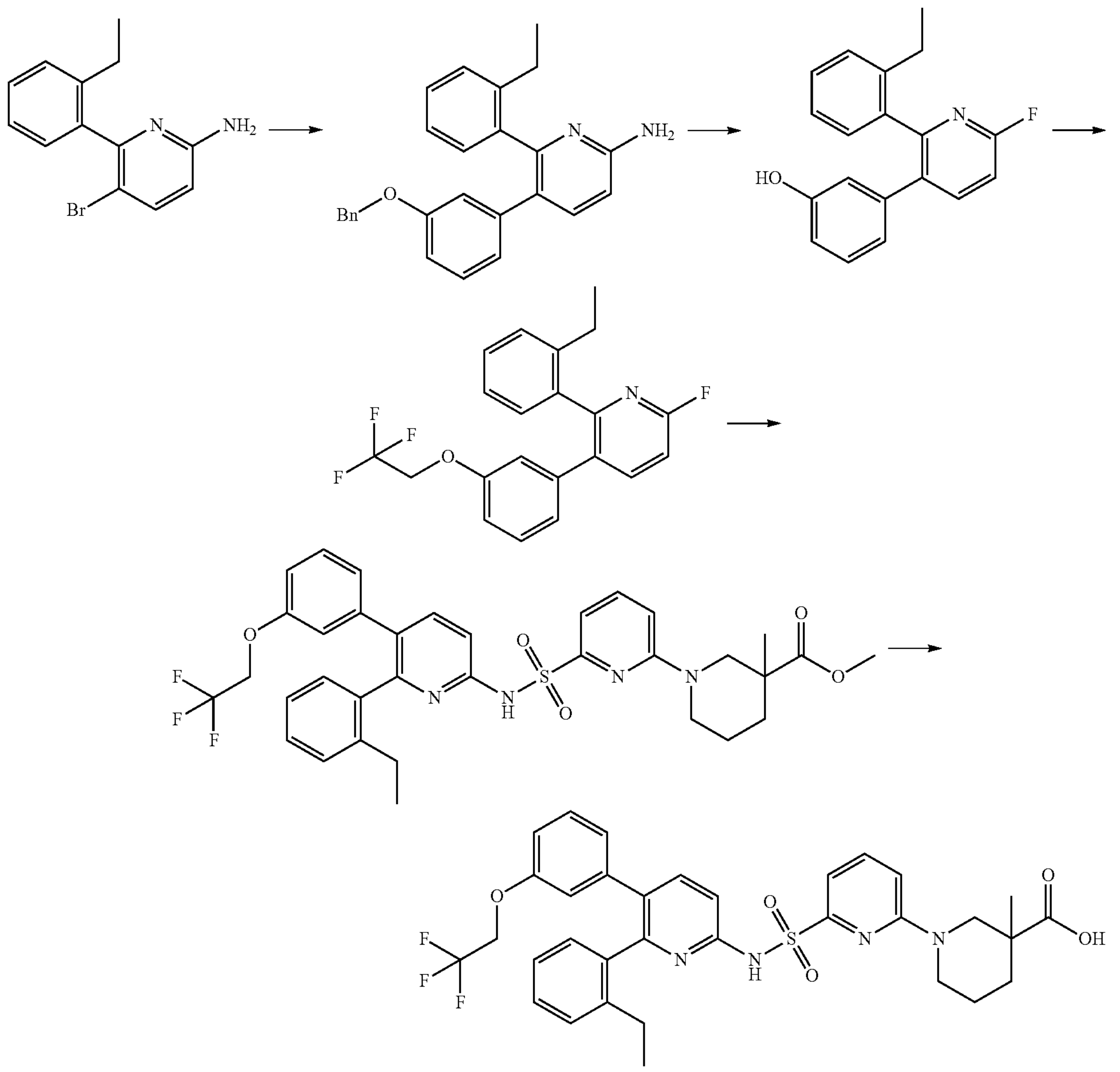

Step 1

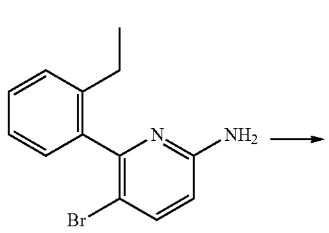

-continued

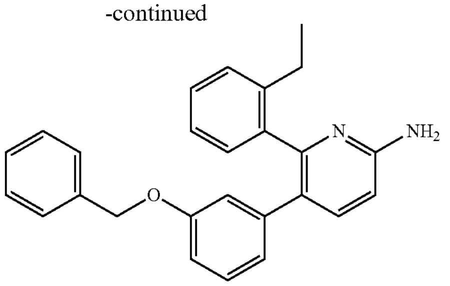

To mixture of 5-bromo-6-(2-ethylphenyl)pyridin-2-amine (1.01 g, 3.6 mmol), synthesized similarly as Example 20, $Cs_2CO_3$ (3.5 g, 10.8 mmol), $PdCl_2$(dppf) (264 mg, 0.3 mmol) and (3-benzyloxyphenyl)boronic acid (1.0 g, 3.6 mmol) in 1.4-dio/H2O (12 mL) was stirred at 110° C. for 16 h. The reaction mixture was diluted with water (50 mL) and extracted with ethyl acetate (3×80 mL). The organic layers were combined, dried over anhydrous sodium sulfate and concentrated in vacuo. The mixture was purified by SGC (PE/EA=4/1) to afford product 5-(3-(benzyloxy)phenyl)-6-(2-ethylphenyl)pyridin-2-amine (700 mg, 51%) as a brown oil.

LCMS: LC retention time 2.04 min. MS (ESI) m/z 381 $[M+H]^+$.

Step 2

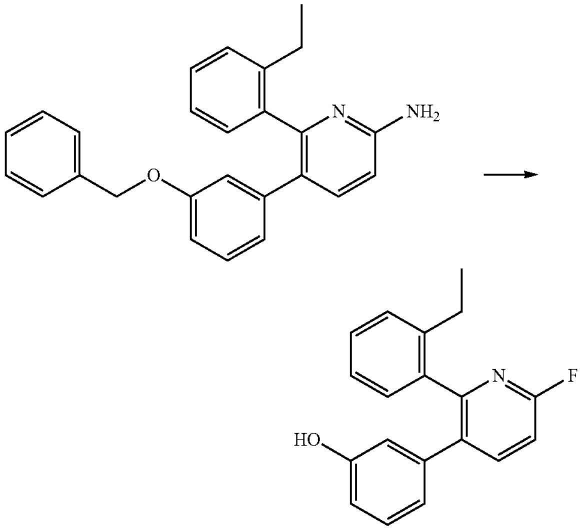

To the mixture of 5-(3-(benzyloxy)phenyl)-6-(2-ethylphenyl)pyridin-2-amine (700 mg, 1.8 mmol) in HF (3.0 mL) was added $NaNO_2$ (190 mg, 2.7 mmol) and stirred at 80° C. for 16 h. The mixture was then poured into $H_2O$ (8 mL) and extracted with EtOAc (3×5 mL). The combined organic washes were dried over $Na_2SO_4$, concentrated. The mixture was purified by SGC (PE/EA=10/1) to afford product 3-(2-(2-ethylphenyl)-6-fluoropyridin-3-yl)phenol (340 mg, 63%) as a yellow oil.

LCMS: LC retention time 2.09 min. m/z 294 $[M+H]^+$.

Step 3

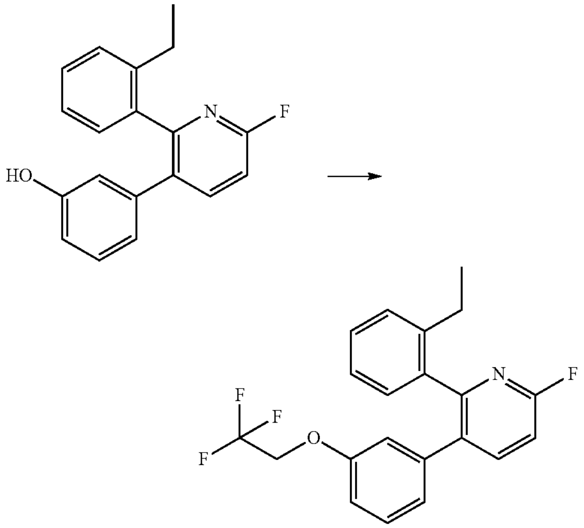

The mixture of 3-(2-(2-ethylphenyl)-6-fluoropyridin-3-yl)phenol (340 mg, 1.16 mmol) and 1,1,1-trifluoro-2-iodoethane (268 mg, 1.27 mmol) in DMF (3.0 mL) was added $K_2CO_3$ (480 mg, 3.4 mmol). The reaction mixture stirred at 70° C. for 16 h. The reaction mixture was diluted with water (5 mL) and extracted with ethyl acetate (3×5 mL). The organic layers were combined, dried over anhydrous sodium sulfate and concentrated in vacuo. The mixture was purified by SGC (PE/EA=20/1) to afford product 2-(2-ethylphenyl)-6-fluoro-3-(3-(2,2,2-trifluoroethoxy)phenyl)pyridine (180 mg, 41.4%) as a yellow oil.

LCMS: LC retention time 2.36 min. m/z 376 $[M+H]^+$.

Step 4

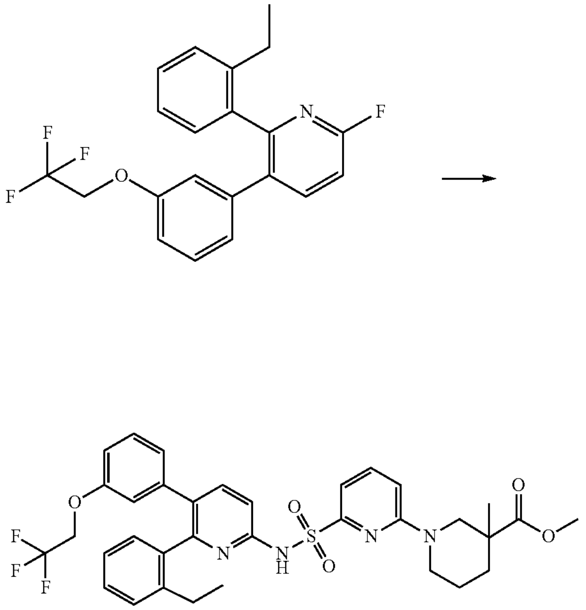

To a solution of 2-(2-ethylphenyl)-6-fluoro-3-(3-(2,2,2-trifluoroethoxy)phenyl)pyridine (180 mg, 0.48 mmol) in DMSO (3.0 mL), added methyl 3-methyl-1-(6-sulfamoyl-2-pyridyl)piperidine-3-carboxylate (0.225 g, 0.7 mmol) and $K_2CO_3$ (0.662 g, 4.8 mmol). The resulting mixture was stirred at 130° C. overnight. After that, the reaction mixture was washed with water (5 mL), extracted with ethyl acetate (15 mL×3), washed with brine (5 mL), dried over anhydrous sodium sulfate and filtered. The filtrate was concentrated and purified by silica gel column chromatography on silica gel (PE/EA=2/1) to afford product methyl 1-(6-(N-(6-(2-ethylphenyl)-5-(3-(2,2,2-trifluoroethoxy)phenyl)pyridin-2-yl)sulfamoyl)pyridin-2-yl)-3-methylpiperidine-3-carboxylate (80 mg, 24.9%) as yellow oil.

LCMS: LC retention time 2.33 min. MS (ESI) m/z 669 $[M+H]^+$.

Step 5

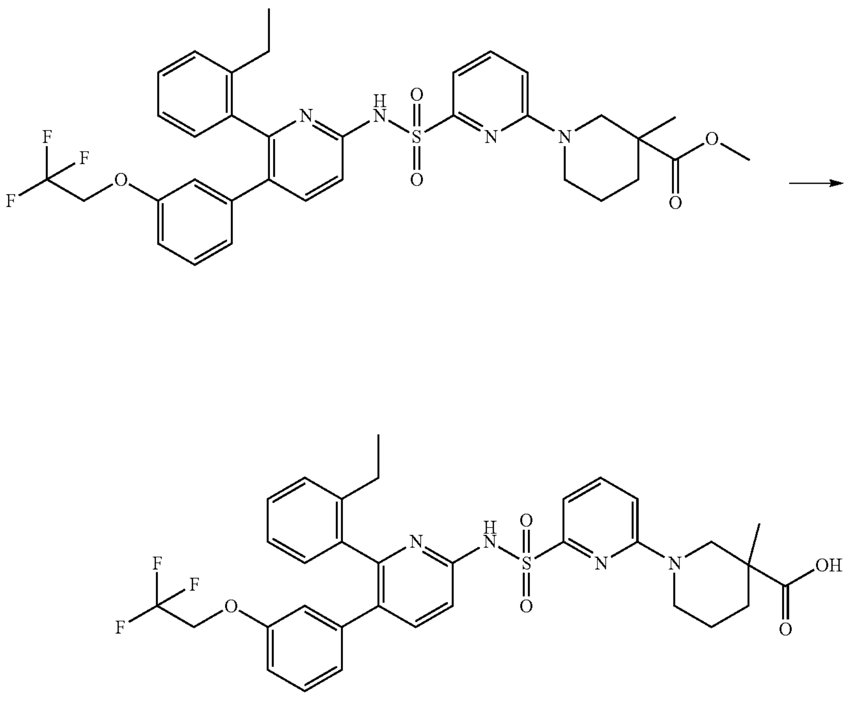

To a solution of methyl 1-[6-[[6-(2-ethylphenyl)-5-[3-(2,2,2-trifluoroethoxy)phenyl]-2-pyridyl]sulfamoyl]-2-pyridyl]-3-methyl-piperidine-3-carboxylate (0.0800 g, 0.000120 mol) in mixed solvents of MeOH/THF/H2O (4/2/1 mL), was added $LiOH \cdot H_2O$ (0.0301 g, 0.000718 mol), then the mixture was stirred at 25° C. for 16 hours. TLC (PE/EA=4/1) showed the starting material was consumed, the mixture was evaporated to remove the organic solvents, the residual was adjusted to pH=7 with 1 N HCl, extracted with EA (10 mL×3), the combined organic layers were dried over $Na_2SO_4$, filtered and concentrated to dryness to give the crude product, which was purified by prep-HPLC to give 1-[6-[[6-(2-ethylphenyl)-5-[3-(2,2,2-trifluoroethoxy)phenyl]-2-pyridyl]sulfamoyl]-2-pyridyl]-3-methyl-piperidine-3-carboxylic acid (8.0 mg, 0.01 mmol, yield: 10.2%) as a white solid.

LCMS: LC retention time 2.21 min. MS (ESI) m/z 655 $[M+H]^+$ $^1H$ NMR (400 MHz, chloroform-d) δ 7.86 (d, J=8.6 Hz, 1H), 7.73 (d, J=8.6 Hz, 1H), 7.42 (s, 1H), 7.23 (m, 1H), 7.16 (t, J=8.0 Hz, 1H), 7.03 (m, 4H), 6.79 (m, 2H), 6.74 (s, 1H), 6.48 (s, 1H), 4.99 (d, J=13.6 Hz, 1H), 3.92 (m, 3H), 3.04 (t, J=12.2 Hz, 1H), 2.73 (m, 1H), 1.78 (m, 4H), 1.33 (m, 5H), 1.17 (s, 3H).

Example 22

5-(4-chloro-3-(neopentyloxy)phenyl)-2-((phenylsulfonyl)-12-azaneyl)-4-(4-(trifluoromethyl)phenyl)pyrimidine

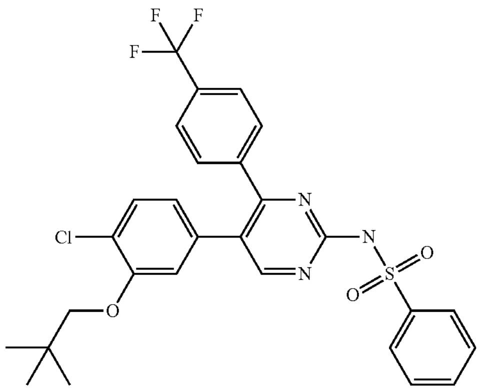 [SMILES: CC(C)(C)COc1cc(-c2cnc(NS(=O)(=O)c3ccccc3)nc2-c2ccc(C(F)(F)F)cc2)ccc1Cl]

Synthesis Scheme

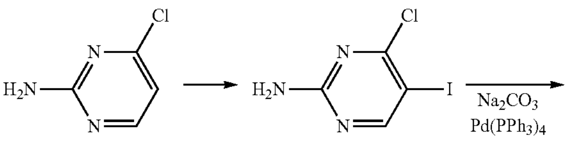

-continued

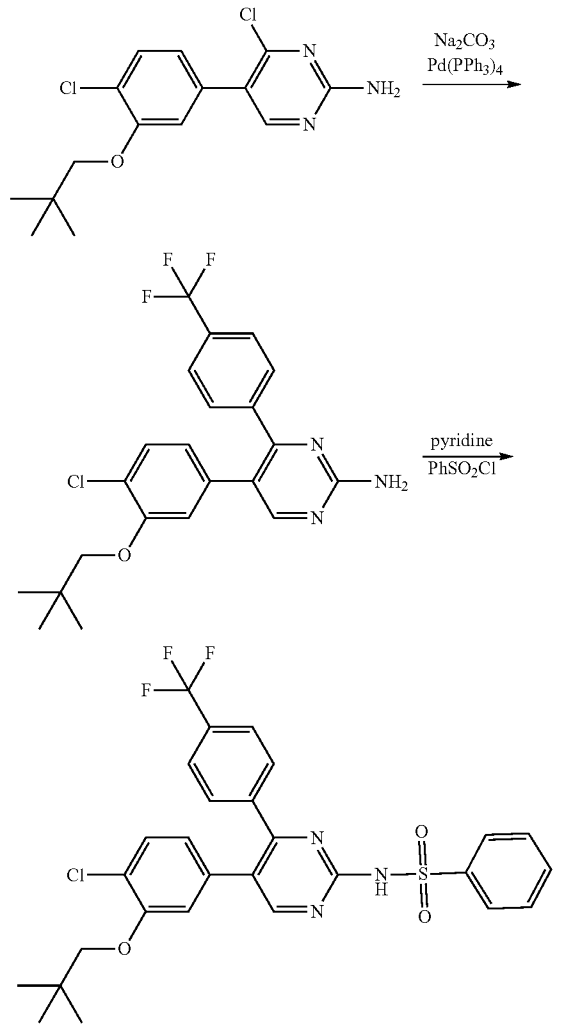

Step 1

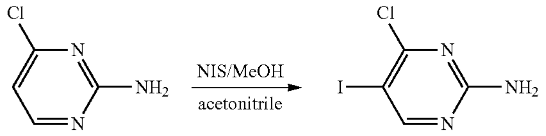 [SMILES: Nc1nccc(Cl)n1 ; Nc1ncc(I)c(Cl)n1]

To a mixture of 4-chloropyrimidin-2-amine (496 mg, 3.83 mmol) in methanol (7 mL) and acetonitrile (5 mL), N-iodosuccinimide (876 mg, 3.89 mmol) was added and the resulting mixture was stirred at 60° C. for 3 hours. The reaction mixture was allowed to cool to room temperature, treated with EA (100 mL) washed with water (50 mL) and saturated ammonium chloride (50 mL) and dried over $Na_2SO_4$. The solvent removed under reduced pressure and purified by silica gel column chromatography (PE/EA=5:1) to give 4-chloro-5-iodopyrimidin-2-amine (800 mg, 81.9%) as yellow solid.

LCMS: purity 81.2%; MS (ESI) m/z 255 $[M+H]^+$.

Step 2

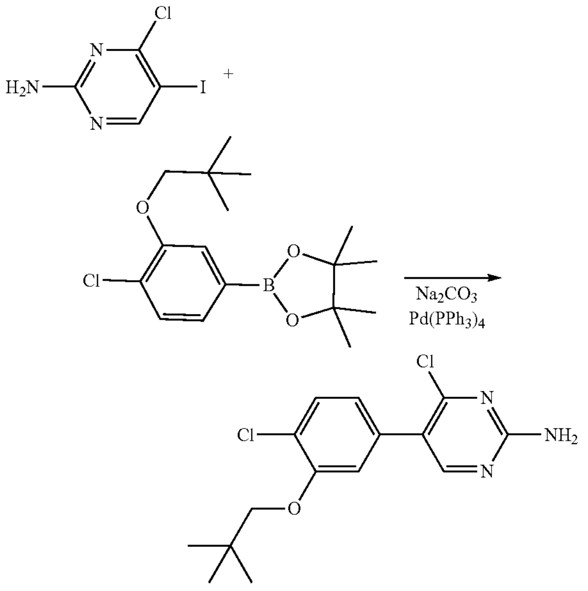

To a solution of 4-chloro-5-iodopyrimidin-2-amine (110 mg, 0.431 mmol), $Na_2CO_3$ (93 mg, 0.877 mmol) and 2-(4-chloro-3-(neopentyloxy)phenyl)-4,4,5,5-tetramethyl-1,3,2-dioxaborolane (160 mg, 0.493 mmol) were added toluene (4 mL), EtOH (2 mL) and water (1 mL). The mixture was bubbled with argon for 5 min then charged with $Pd(Ph_3P)_4$ (82 mg, 0.071 mmol). The mixture was stirred at 73° C. for 5 hours and then cooled to room temperature. The mixture was partitioned between EtOAc (30 mL) and water (30 mL). The organic layer was dried over $Na_2SO_4$ and filtered. The filtrate was concentrated and purified by silica gel column chromatography (PE/EA=3/1) to give 4-chloro-5-(4-chloro-3-(neopentyloxy)phenyl)pyrimidin-2-amine (84 mg, 60%) as yellow solid.

LCMS: purity 100%; MS (ESI) m/z 325 $[M+H]^+$.

Step 3

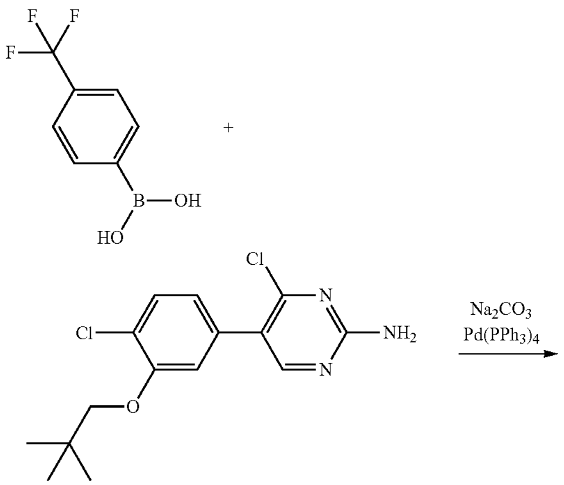

-continued

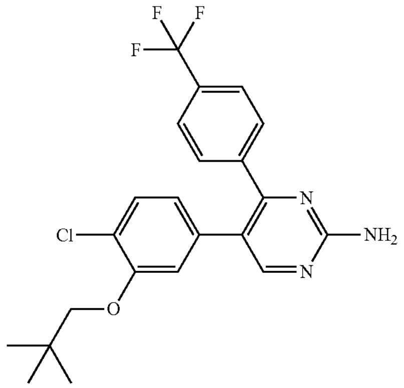

4-chloro-5-(4-chloro-3-(neopentyloxy)phenyl)pyrimidin-2-amine (60 mg, 0.185 mmol), $Na_2CO_3$ (43 mg, 0.406 mmol) and (4-(trifluoromethyl)phenyl)boronic acid (65 mg, 0.342 mmol) were suspended in 1,4-dioxane (3 mL) and water (1 mL). The mixture was bubbled with argon for 5 min then charged with $Pd(Ph_3P)_4$ (40 mg, 0.035 mmol). The mixture was stirred at 73° C. for 20 hours and then cooled to room temperature. The mixture was partitioned between (20 mL) and water (20 mL). The organic layer was dried over $Na_2SO_4$ and filtered. The filtrate was concentrated and purified by silica gel column chromatography (PE/EA=5/1) to give 5-(4-chloro-3-(neopentyloxy)phenyl)-4-(4-(trifluoromethyl)phenyl)pyrimidin-2-amine (70 mg, 87.5 percent) as yellow solid. LCMS: purity 85.2%; MS (ESI) m/z 435 $[M+H]^+$.

Step 4

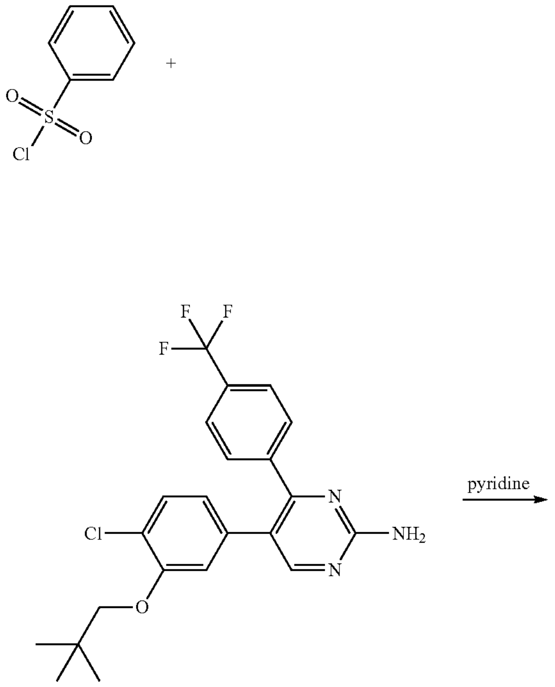

-continued

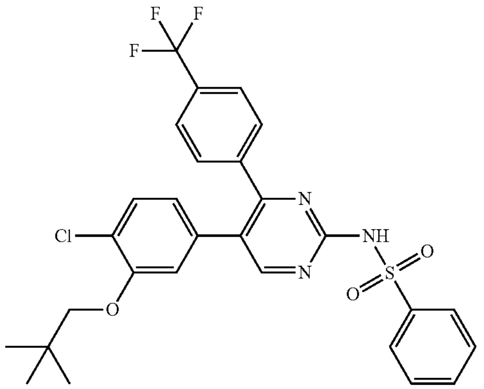

5-(4-chloro-3-(neopentyloxy)phenyl)-4-(4-(trifluoromethyl)phenyl)pyrimidin-2-amine (36 mg, 0.083 mmol) and benzenesulfonyl chloride (30 mg, 0.169 mmol) were suspended in pyridine (3 mL). The mixture was bubbled with nitrogen and was stirred at 75° C. for 20 hours and then cooled to room temperature. The mixture was partitioned between (20 mL) and water (20 mL).

The organic layer was dried over $Na_2SO_4$ and filtered. The filtrate was concentrated and purified by silica gel column chromatography (PE/EA=5/1) to give N-(5-(4-chloro-3-(neopentyloxy)phenyl)-4-(4-(trifluoromethyl)phenyl)pyrimidin-2-yl)benzenesulfonamide (10 mg, 47.6%) as yellow solid.

LCMS: purity 100%; retention time 1.78 min; MS (ESI) m/z 576 $[M+H]^+$.

$^1H$ NMR (400 MHz, DMSO) δ 12.13 (s, 1H), 8.65 (s, 1H), 8.01 (d, J=5.2 Hz, 2H), 7.77-7.60 (m, 5H), 7.46-7.35 (m, 3H), 6.86-6.74 (m, 2H), 3.39 (s, 2H), 0.89 (s, 9H) ppm.

Example 23

N-(5-(4-chloro-3-(neopentyloxy)phenyl)-4-(4-(trifluoromethyl)phenyl)pyrimidin-2-yl)-3-(methylsulfonamido)benzenesulfonamide

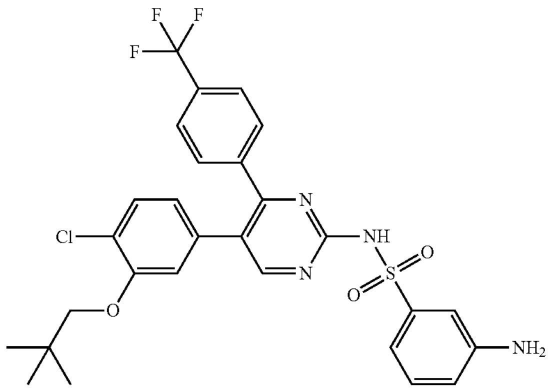

Synthetic Scheme

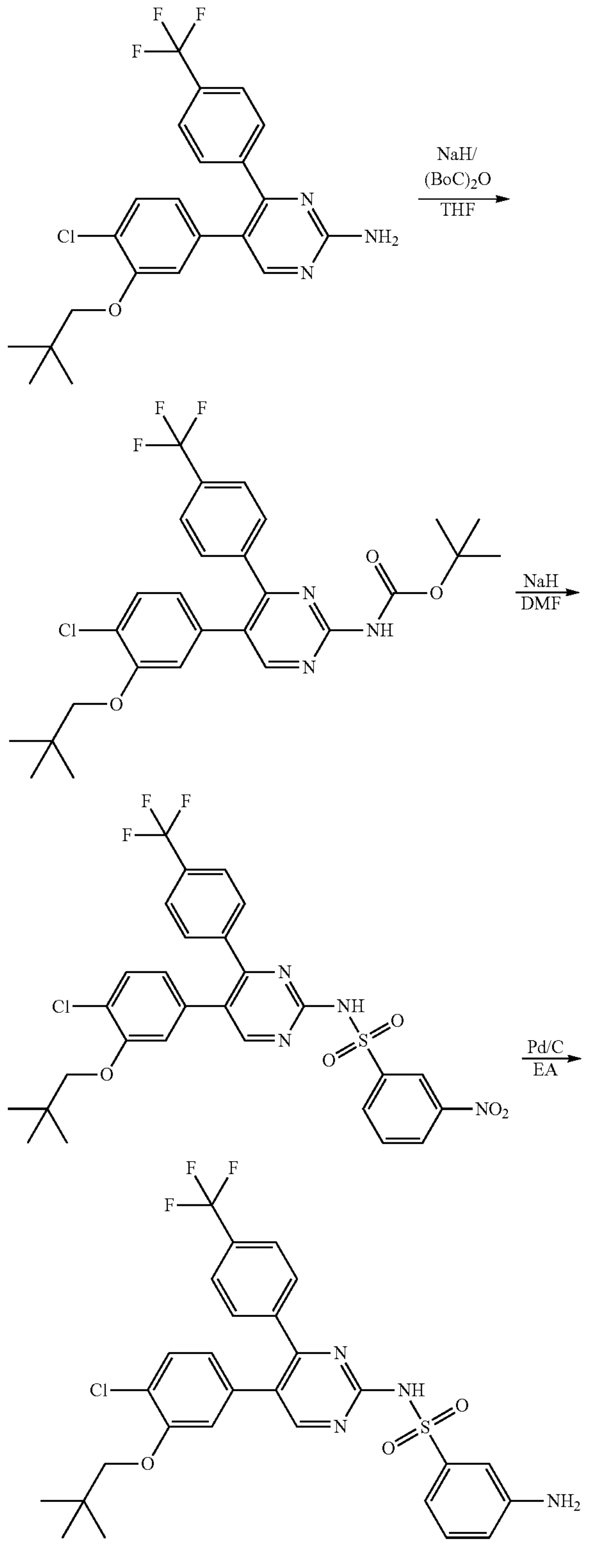

Step 1

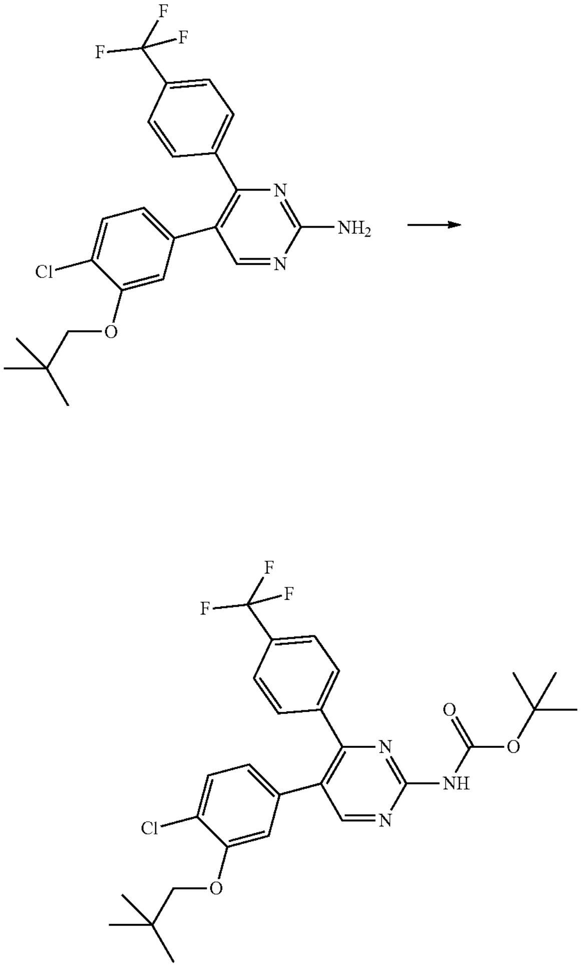

Sodium hydride (23 mg, 0.58 mmol, 60% mineral oil dispersion) was added to a stirred solution of 5-(4-chloro-3-(neopentyloxy)phenyl)-4-(4-(trifluoromethyl)phenyl)pyrimidin-2-amine (95 mg, 0.22 mmol) in dry THF (7 mL) at room temperature under nitrogen and then followed by the addition of di-tert-butyl dicarbonate (70 mg, 0.32 mmol). The reaction mixture was stirred at 65° C. for 2 hours. The reaction was cooled to 0° C. and quenched with brine (5 mL). The filtrate was diluted with ethyl acetate (100 mL), washed with brine (50 mL×2) and dried over sodium sulfate. The filtrate was concentrated and purified by silica gel column chromatography (PE) to give tert-butyl (5-(4-chloro-3-(neopentyloxy)phenyl)-4-(4-(trifluoromethyl)phenyl)pyrimidin-2-yl)carbamate (80 mg, 68.3%) as white solid.

$^1$H NMR (400 MHz, chloroform-d) δ 8.65 (s, 1H), 7.59-7.56 (m, 5H), 7.33 (d, J=8.0 Hz, 1H), 6.69 (d, J=8.4 Hz, 1H), 6.55 (s, 1H), 3.33 (s, 2H), 1.52 (s, 9H), 1.01 (s, 9H).

Step 2

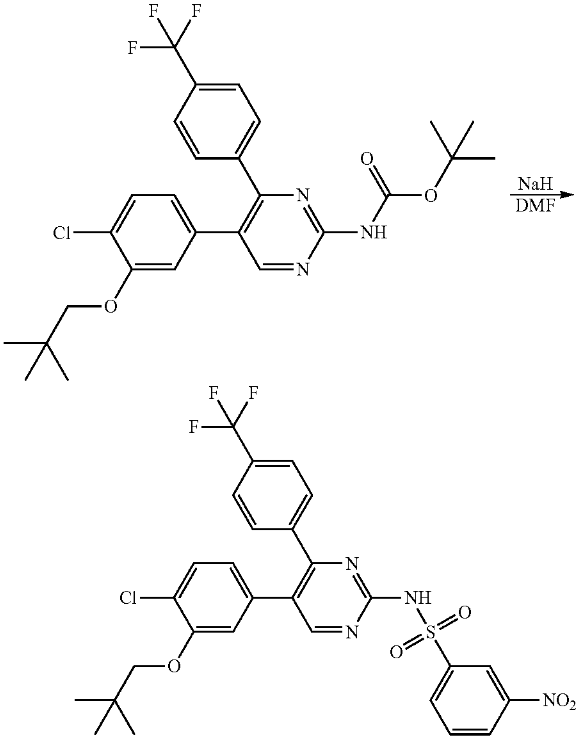

Sodium hydride (15 mg, 0.375 mmol, 60% mineral oil dispersion) was added to a stirred solution of tert-butyl (5-(4-chloro-3-(neopentyloxy)phenyl)-4-(4-(trifluoromethyl) phenyl)pyrimidin-2-yl)carbamate (60 mg, 0.11 mmol) in dry DMF (4 mL) at room temperature under nitrogen and then followed by the addition of 3-nitrobenzenesulfonamide (50 mg, 0.23 mmol). The reaction mixture was stirred at 65° C. for 20 hours. The reaction was cooled to 0° C. and quenched with brine (8 mL). The filtrate was diluted with ethyl acetate (50 mL), washed with brine (50 mL×2) and dried over sodium sulfate. The filtrate was concentrated and purified by silica gel column chromatography (PE/EA=2/1) to give N-(5-(4-chloro-3-(neopentyloxy)phenyl)-4-(4-(trifluoromethyl)phenyl)pyrimidin-2-yl)-3-nitrobenzenesulfonamide (27 mg, 39.1%) as yellow solid.

LCMS: Purity 83.2%; MS (ESI) m/z 621 $[M+H]^+$.

Step 3

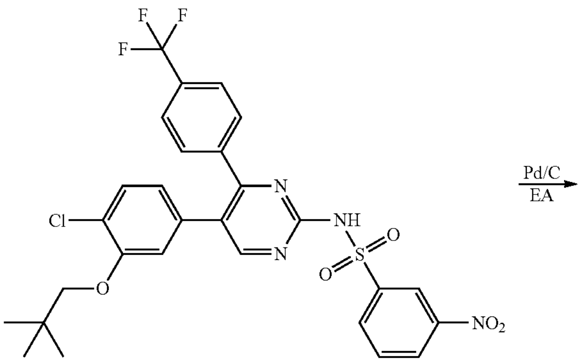

-continued

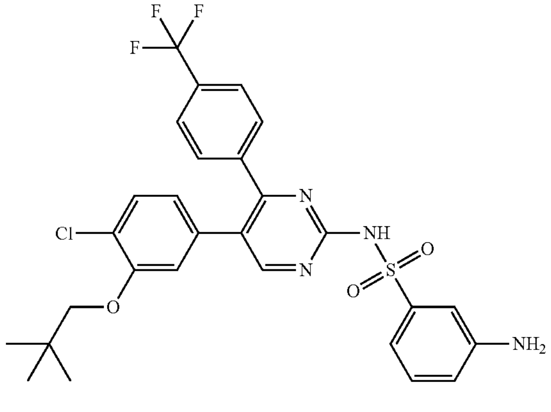 [SMILES: CC(C)(C)COc1cc(-c2cnc(NS(=O)(=O)c3cccc(N)c3)nc2-c2ccc(C(F)(F)F)cc2)ccc1Cl]

A mixture of N-(5-(4-chloro-3-(neopentyloxy)phenyl)-4-(4-(trifluoromethyl)phenyl)pyrimidin-2-yl)-3-nitrobenzenesulfonamide (27 mg 0.044 mmol) and 32 mg of 10% Pd—C in 4 mL of EA containing 1% water was vigorously stirred under 1 atm of $H_2$ at room temperature for 3 hours and then filtered. The filtrate was concentrated and then purified by Pre-HPLC to give 3-amino-N-(5-(4-chloro-3-(neopentyloxy)phenyl)-4-(4-(trifluoromethyl) phenyl)pyrimidin-2-yl) benzenesulfonamide (10 mg, 18.7%) as white solid.

LCMS: LC retention time 1.74 min. MS (ESI) m/z 591 $[M+H]^+$.

$^1$H NMR (400 MHz, chloroform-d) δ 8.58 (s, 1H), 7.60 (d, J=8.0 Hz, 2H), 7.50-7.45 (m, 4H), 7.33 (d, J=8.4 Hz, 1H), 6.80 (d, J=8.4 Hz, 1H), 6.60 (d, J=7.2 Hz, 1H), 6.54 (s, 1H), 3.85 (s, 2H), 3.34 (s, 2H), 1.01 (s, 9H).

Example 24

N-(5-(4-chloro-3-(neopentyloxy)phenyl)-4-(4-(trifluoromethyl)phenyl)pyrimidin-2-yl)-3-(methylsulfonamido)benzenesulfonamide

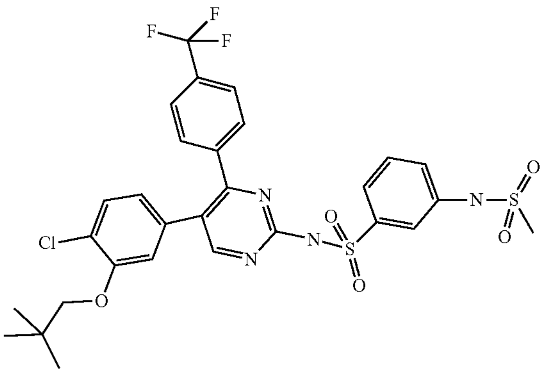 [SMILES: CC(C)(C)COc1cc(-c2cnc(NS(=O)(=O)c3cccc(NS(C)(=O)=O)c3)nc2-c2ccc(C(F)(F)F)cc2)ccc1Cl]

Synthesis Scheme

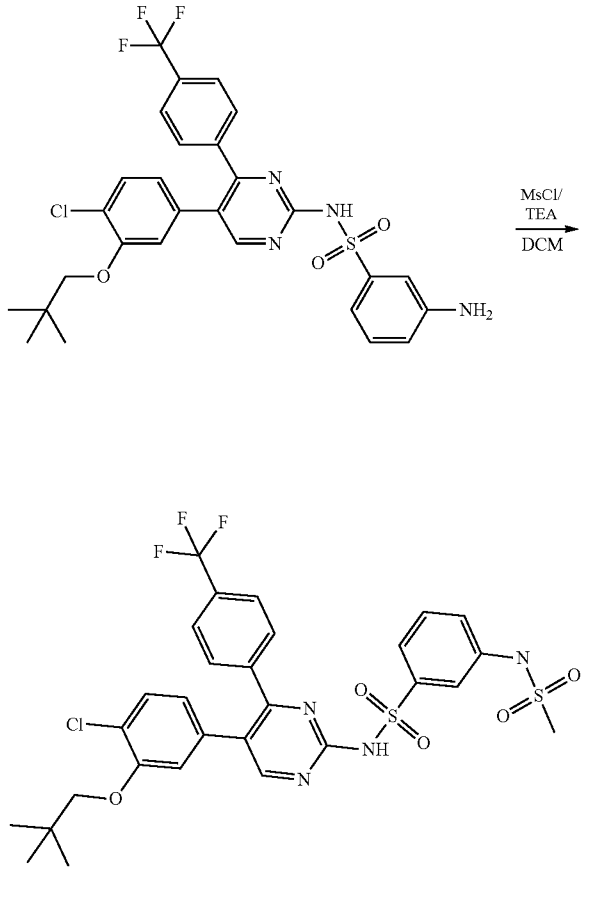

To a solution of 3-amino-N-(5-(4-chloro-3-(neopentyloxy)phenyl)-4-(4-(trifluoromethyl) phenyl)pyrimidin-2-yl) benzenesulfonamide (10 mg, 0.017 mmol) in DCM (5 mL) was added TEA (48 mg, 0.475 mmol) and MsCl (32 mg, 0.28 mmol) at 0° C. The resulting mixture was stirred at 20° C. for 20 hours and water (5 mL) was added. The mixture was extracted with DCM (10 mL×3). The combined organic phase was washed with brine (5 mL), dried over $Na_2SO_4$, filtered and concentrated to give brown oil, then purified by Prep-HPLC to give N-(5-(4-chloro-3-(neopentyloxy)phenyl)-4-(4-(trifluoromethyl)phenyl)pyrimidin-2-yl)-3-(methylsulfonamido)benzenesulfonamide (6.0 mg; 53%) as white solid.

LCMS: LC retention time 1.67 min. MS (ESI) m/z 669 $[M+H]^+$.

$^1$H NMR (400 MHz, chloroform-d) δ 8.58 (s, 1H), 8.04 (s, 1H), 8.43 (d, J=7.6 Hz, 1H), 7.66 (d, J=8.4 Hz, 2H), 7.52-7.46 (m, 4H), 7.35 (d, J=8.0 Hz, 1H), 6.79 (d, J=7.6 Hz, 1H), 6.67 (s, 1H), 3.33 (s, 2H), 2.94 (s, 3H), 0.98 (s, 9H).

Example 25

N-(5-(4-chloro-3-(neopentyloxy)phenyl)-4-(4-(trifluoromethyl)phenyl)pyrimidin-2-yl)pyridine-3-sulfonamide

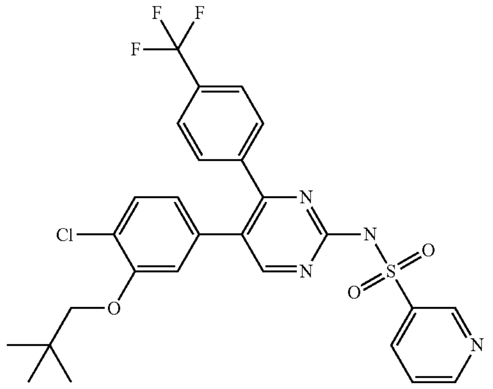 [SMILES: CC(C)(C)COc1cc(-c2cnc(NS(=O)(=O)c3cccnc3)nc2-c2ccc(C(F)(F)F)cc2)ccc1Cl]

Example 25 was synthesized by essentially the same protocol as Example 23.

LCMS: LC retention time 1.67 min. MS (ESI) m/z 577 $[M+H]^+$.

$^1$H NMR (400 MHz, chloroform-d) δ 9.37 (s, 1H), 8.82 (s, 1H), 8.64 (s, 1H), 8.44 (d, J=8.0 Hz, 1H), 7.62 (d, J=8.0 Hz, 2H), 7.48-7.41 (m, 3H), 7.33 (d, J=8.0 Hz, 1H), 6.66 (d, J=8.4 Hz, 1H), 6.53 (s, 1H), 3.34 (s, 2H), 0.90 (s, 9H).

Example 26

5-(4-chloro-3-(neopentyloxy)phenyl)-2-(((6-chloropyridin-2-yl)sulfonyl)-12-azaneyl)-4-(4-(trifluoromethyl)phenyl)pyrimidine

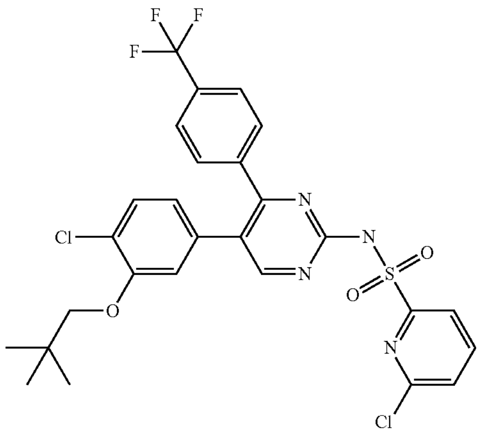 [SMILES: CC(C)(C)COc1cc(-c2cnc(NS(=O)(=O)c3cccc(Cl)n3)nc2-c2ccc(C(F)(F)F)cc2)ccc1Cl]

Example 26 was synthesized by essentially the same protocol as Example 23.

LCMS: purity 100%; retention time 2.23 min; MS (ESI) m/z 612 $[M+H]^+$.

$^1$H NMR (400 MHz, CDCl3) ? 8.67 (s, 1H), 8.22 (d, J=8.0 Hz, 1H), 7.82 (t, J=8.0 Hz, 1H), 7.57 (d, J=8.4 Hz, 2H), 7.50

(d, J=7.6 Hz, 1H), 7.43 (d, J=8.4 Hz, 2H), 7.32 (d, J=8.0 Hz, 1H), 6.67 (d, J=8.0 Hz, 1H), 6.56 (s, 1H), 3.35 (s, 2H), 1.01 (s, 9H) ppm.
Example 27a
N-(5-(3-((1S,3S)-3-(trifluoromethoxy)cyclopentyl) phenyl)-4-(2-(trifluoromethyl)phenyl)pyrimidin-2-yl)benzenesulfonamide (P1)
P1
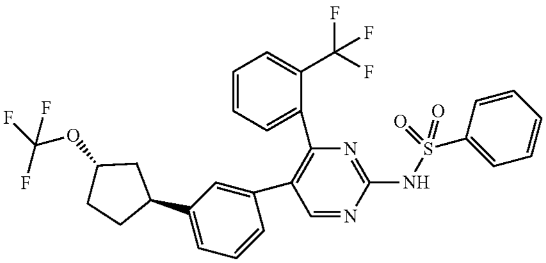
Example 27b
N-(5-(3-((1S,3R)-3-(trifluoromethoxy)cyclopentyl) phenyl)-4-(2-(trifluoromethyl)phenyl)pyrimidin-2-yl)benzenesulfonamide
P2
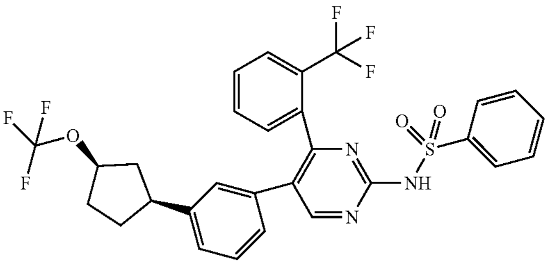
Synthetic Scheme
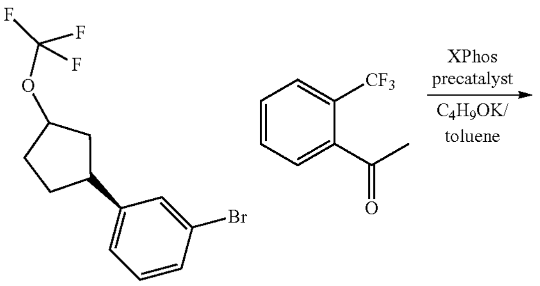
-continued
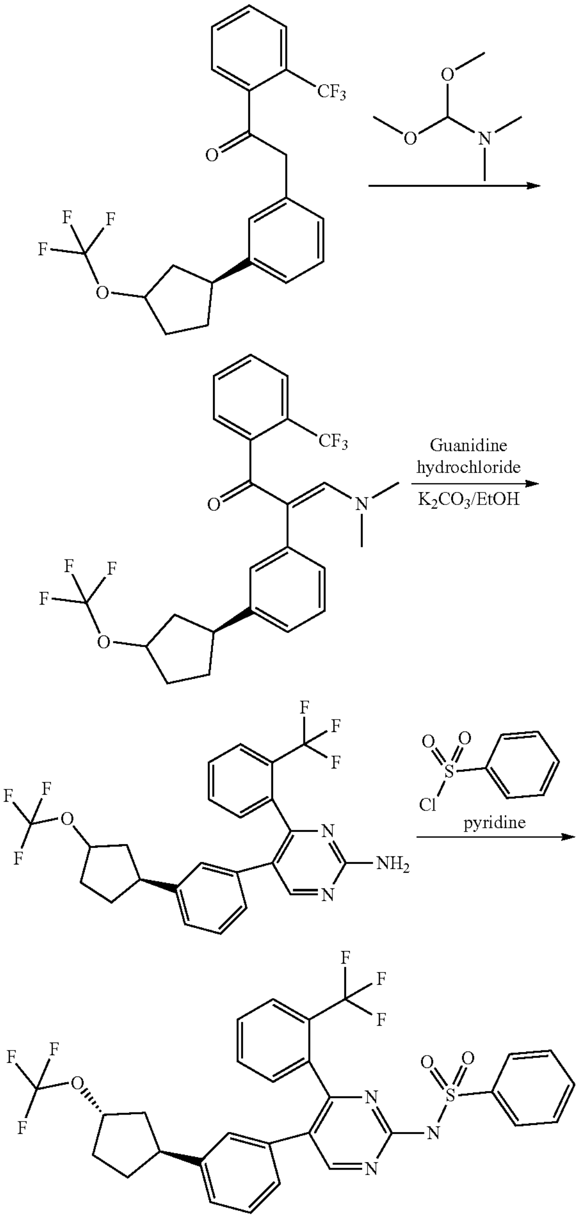
Step 1
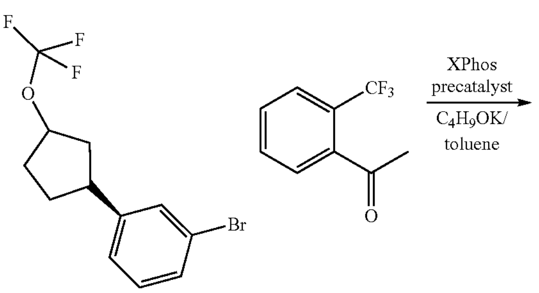

-continued

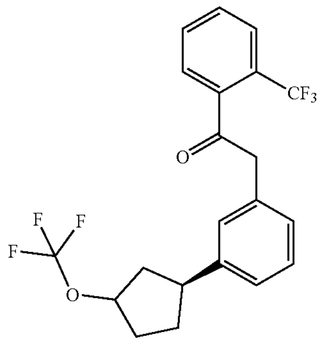

XPhos precatalyst (16 mg, 0.01 mmol) and $C_4H90K$ (441 mg, 3.94 mmol) were added to a test tube equipped with a stir bar. The test tube was sealed with a Teflon septum-lined screw cap and evacuated/backfilled with argon 1-(2-(trifluoromethyl)phenyl)ethan-1-one (366 mg, 1.95 mmol) and 1-bromo-3-((1S)-3-(trifluoromethoxy)cyclopentyl)benzene (610 mg, 1.97 mmol) and toluene (16 mL) were added to the reaction vessel in succession via syringe. The reaction mixture was heated to 70° C. for 4 hours. After cooling to room temperature, saturated aqueous $NH_4Cl$ (40 mL) was added to the reaction mixture and the resulting mixture was vigorously shaken. This mixture was then poured into a separatory funnel and extracted with extracted with ethyl acetate (50 mL×2). The combined organic was washed with brine and dried over sodium sulfate and evaporated. The resulting residue was purified by silica gel chromatography with a Biotage instrument (PE/EA=3/1) to afford 2-(3-((1S)-3-(trifluoromethoxy)cyclopentyl)phenyl)-1-(2-(trifluoromethyl)phenyl)ethan-1-one (700 mg, 86.4%) as light yellow oil.

LCMS: LC retention time 2.29 min. MS (ESI) m/z 439 $[M+Na]^+$

Step 2

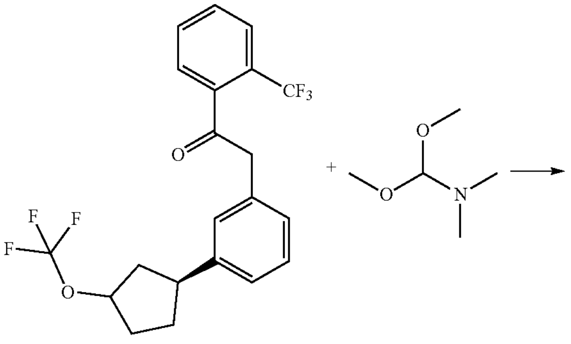

-continued

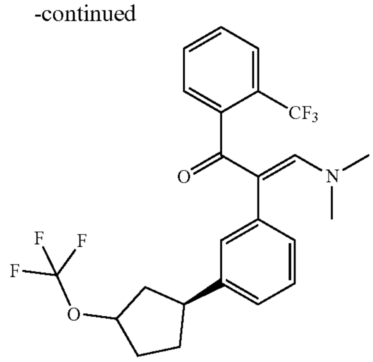

To a solution of 2-(3-((1S)-3-(trifluoromethoxy)cyclopentyl)phenyl)-1-(2-(trifluoromethyl) phenyl)ethan-1-one (110 mg, 0.264 mmol) in Dimethylformamide dimethyl acetal (0.5 mL) was stirred at 80° C. overnight. After that, the reaction mixture was concentrated and gave (E)-3-(dimethylamino)-2-(3-((1S)-3-(trifluoromethoxy)cyclopentyl)phenyl)-1-(2-(trifluoromethyl) phenyl)prop-2-en-1-one (124 mg; 100%) as yellow oil.

LCMS: LC retention time 2.23 min. MS (ESI) m/z 472 $[M+H]^+$

Step 3

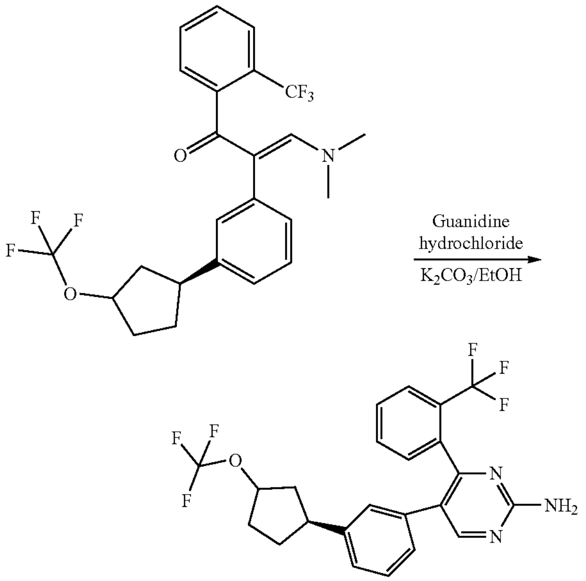

To a solution of (E)-3-(dimethylamino)-2-(3-((1S)-3-(trifluoromethoxy) cyclopentyl)phenyl)-1-(2-(trifluoromethyl) phenyl)prop-2-en-1-one (124 mg, 0.263 mmol) in EtOH (2.0 mL) was added guanidine hydrochloride (28 mg, 0.293 mmol) and $K_2CO_3$ (113 mg, 0.818 mmol). The resulting mixture was refluxed at 80° C. overnight. After that, the reaction mixture was washed with water (50 mL), extracted with ethyl acetate (50 mL×3), washed with brine (50 mL), dried over anhydrous sodium sulfate and filtered. The filtrate was concentrated and purified by silica gel column chromatography on silica gel (PE/EA=1/1) to give 5-(3-((1S)-3-(trifluoromethoxy)cyclopentyl)phenyl)-4-(2-(trifluoromethyl)phenyl)pyrimidin-2-amine (105 mg; 85.4%) as yellow solid.

LCMS: LC retention time 2.16 min. MS (ESI) m/z 468 $[M+H]^+$

Step 4

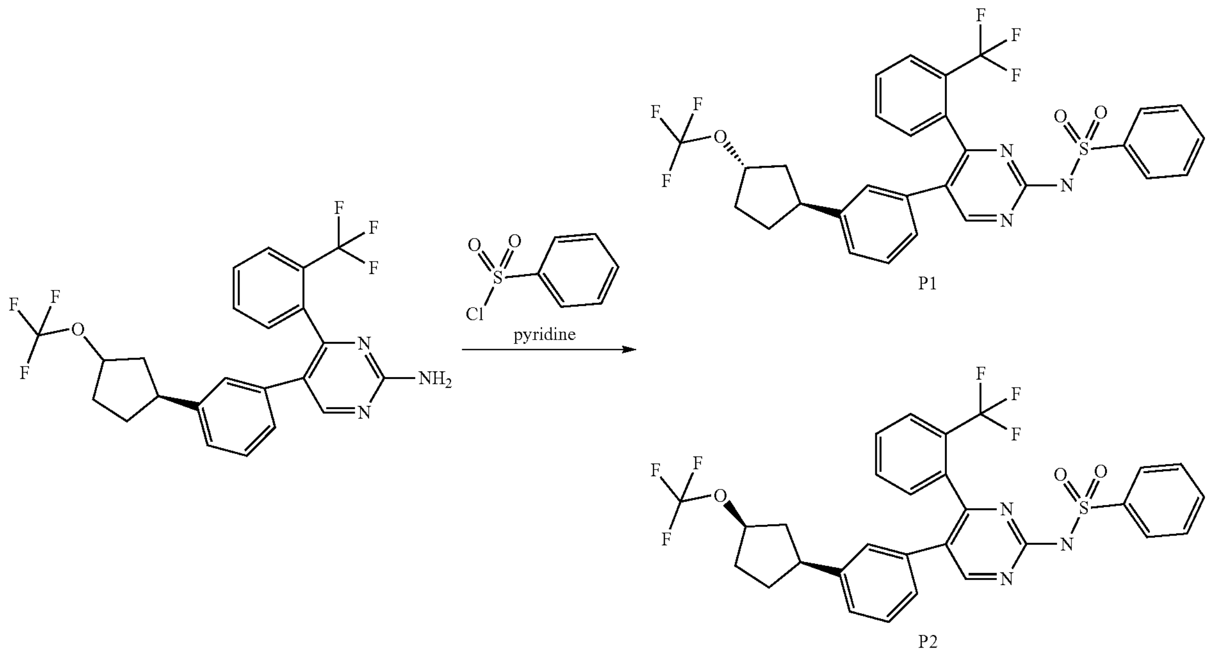

To a solution of 5-(3-((1S)-3-(trifluoromethoxy)cyclopentyl)phenyl)-4-(2-(trifluoromethyl)phenyl)pyrimidin-2-amine (105 mg, 0.225 mmol) in pyridine (2 mL) was added benzenesulfonyl chloride (636 mg, 3.6 mmol) and the mixture was stirred at room temperature for 20 hours. The mixture reaction was purified by Prep-HPLC to give N-(5-(3-((1S,3S)-3-(trifluoromethoxy)cyclopentyl)phenyl)-4-(2-(trifluoromethyl)phenyl)pyrimidin-2-yl) benzenesulfonamide P1 (23.8 mg, 17.5%) and N-(5-(3-(3-(trifluoromethoxy) cyclopentyl)phenyl)-4-(2-(trifluoromethyl)phenyl)pyrimidin-2-yl) benzenesulfonamide P2 (34.8 mg, 25.6%) as white solids.

P1: LCMS: LC retention time 2.27 min. MS (ESI) m/z 608 $[M+H]^+$ $^1$H NMR (400 MHz, chloroform-d) δ 8.63 (s, 1H), 8.40 (s, 1H), 8.16 (d, J=7.6 Hz, 2H), 7.70 (d, J=7.2 Hz, 1H), 7.61 (t, J=8.0 Hz, 1H), 7.54-7.44 (m, 4H), 7.20 (t, J=7.6 Hz, 1H), 7.07 (d, J=7.6 Hz, 2H), 6.95 (d, J=7.2 Hz, 1H), 6.77 (s, 1H), 4.78-4.74 (m, 1H), 3.23-3.14 (m, 1H), 2.18-1.88 (m, 4H), 1.56-1.50 (m, 1H), 1.35-1.27 (m, 1H) ppm.

P2: Purity: >95% LCMS (214 nm & 254 nm); retention time 2.28 min; MS (ESI) m/z 608 $[M+H]^+$ $^1$H NMR (400 MHz, chloroform-d) δ 8.62 (s, 1H), 8.14 (d, J=7.2 Hz, 2H), 7.69 (d, J=6.8 Hz, 1H), 7.61 (t, J=7.6 Hz, 1H), 7.51-7.45 (m, 4H), 7.20 (t, J=8.0 Hz, 1H), 7.09 (d, J=6.8 Hz, 2H), 6.96 (d, J=3.2 Hz, 1H), 6.83 (s, 1H), 4.77-4.72 (m, 1H), 2.93-2.84 (m, 1H), 2.41-2.34 (m, 1H), 2.03-1.86 (m, 3H), 1.57-1.47 (m, 2H) ppm.

The stereochemistry of P1 and P2 were assigned arbitrarily.

Example 28a

N-(5-(3-((1R,3S)-3-(trifluoromethoxy)cyclopentyl) phenyl)-4-(2-(trifluoromethyl)phenyl)pyrimidin-2-yl)benzenesulfonamide (P1)

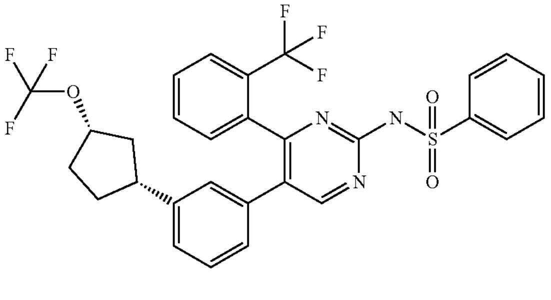 [SMILES: O=S(=O)(Nc1ncc(-c2cccc([C@@H]3CC[C@H](OC(F)(F)F)C3)c2)c(-c2ccccc2C(F)(F)F)n1)c1ccccc1]

Example 28b 2-((phenylsulfonyl)-12-azaneyl)-5-(3-((1R,3R)-3-(trifluoromethoxy)cyclopentyl)phenyl)-4-(2-(trifluoromethyl)phenyl)pyrimidine

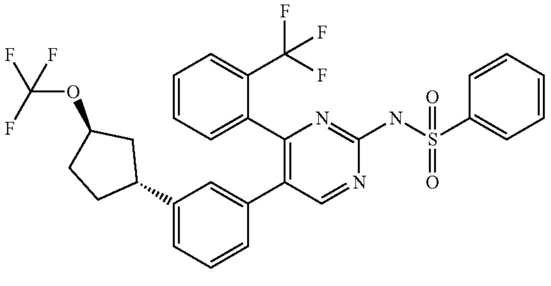 [SMILES: O=S(=O)(Nc1ncc(-c2cccc([C@@H]3CC[C@@H](OC(F)(F)F)C3)c2)c(-c2ccccc2C(F)(F)F)n1)c1ccccc1]

Example 28a and 28b (P1 and P2) were synthesized by essentially the same protocol as Example 27, P1 and P2, starting from 1-bromo-3-((1R)-3-(trifluoromethoxy)cyclopentyl) benzene.

P1: LCMS (acidic): LC retention time 2.311, MS (ESI): m/z 608 $[M+H]^+$.

$^1H$ NMR (400 MHz, methanol-$d_4$) δ 8.57 (s, 1H), 8.05 (d, J=7.6 Hz, 2H), 7.72-7.45 (m, 6H), 7.22-7.12 (m, 3H), 7.01 (d, J=7.6 Hz, 1H), 6.87 (s, 1H), 4.84-4.79 (m, 1H), 2.95-2.88 (m, 1H), 2.40-2.34 (m, 1H), 1.99-1.85 (m, 3H), 1.55-1.47 (m, 2H).

P2: LCMS (acidic): LC retention time 2.330, MS (ESI): m/z 608 $[M+H]^+$.

$^1H$ NMR (400 MHz, methanol-$d_4$) δ 8.57 (s, 1H), 8.05 (d, J=7.6 Hz, 2H), 7.72-7.45 (m, 6H), 7.22-7.12 (m, 3H), 7.01 (d, J=7.6 Hz, 1H), 6.87 (s, 1H), 4.88-4.84 (m, 1H), 3.32-3.11 (m, 1H), 2.21-1.85 (m, 4H), 1.69-1.62 (m, 1H), 1.41-1.32 (m, 2H).

The stereochemistry of P1 and P2 were assigned arbitrarily.

Example 29a 3-amino-N-(5-(3-((1S,3R)-3-(trifluoromethoxy)cyclopentyl)phenyl)-4-(2-(trifluoromethyl)phenyl)pyrimidin-2-yl)benzenesulfonamide $P_1$

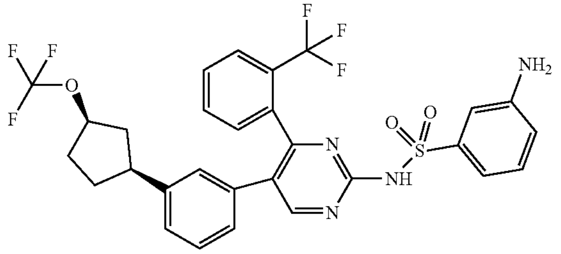

Example 29b 3-amino-N-(5-(3-((1S,3S)-3-(trifluoromethoxy)cyclopentyl)phenyl)-4-(2-(trifluoromethyl)phenyl)pyrimidin-2-yl)benzenesulfonamide $P_2$

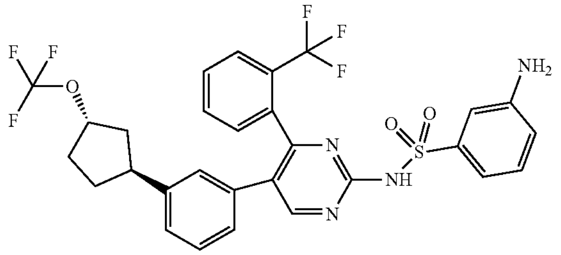

Synthetic Scheme

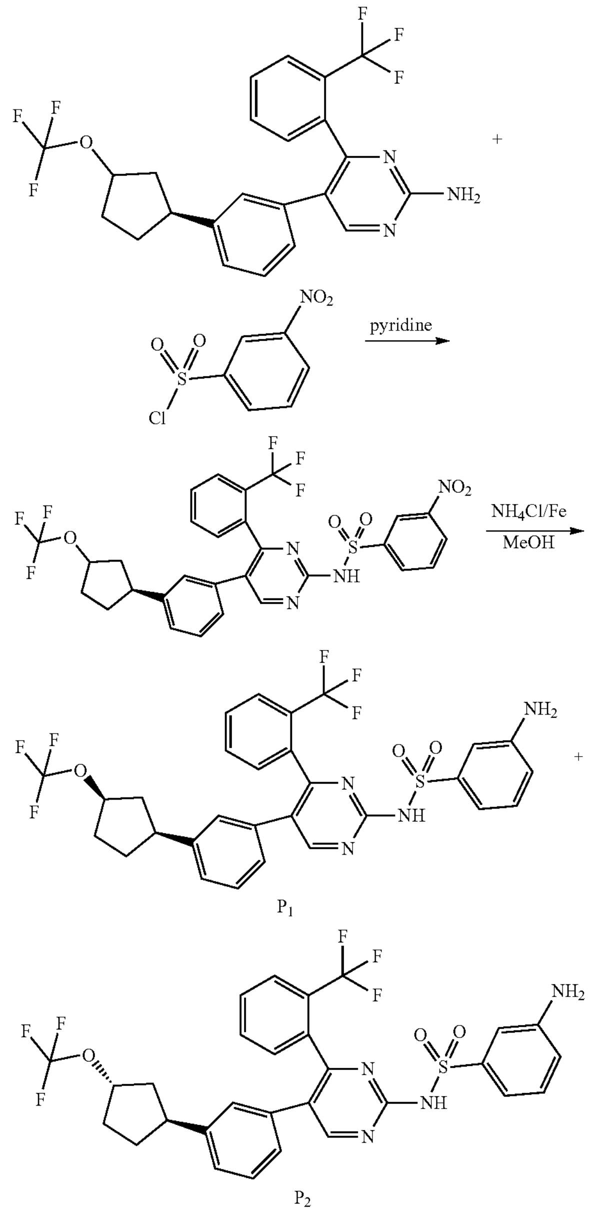

Step 1

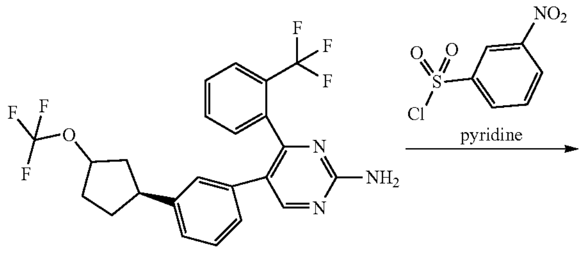

-continued

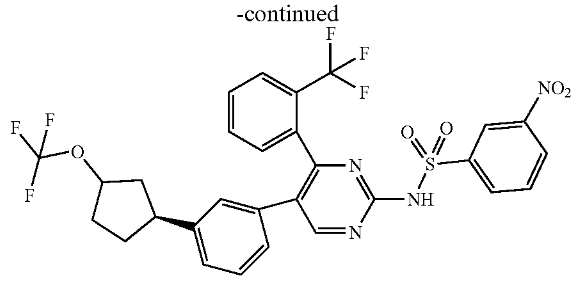

To a solution of 5-(3-((1S)-3-(trifluoromethoxy)cyclopentyl)phenyl)-4-(2-(trifluoromethyl)phenyl)pyrimidin-2-amine (150 mg, 0.321 mmol), obtained from the synthesis of Example 27 in pyridine (1.5 mL) was added 3-nitrobenzenesulfonyl chloride (245 mg, 1.11 mmol) and the mixture was heated at 110° C. for 2 hours under microwave irradiations. After that, the reaction mixture was washed with water (50 mL), extracted with ethyl acetate (50 mL×2), washed with brine (50 mL), dried over anhydrous sodium sulfate and filtered. The filtrate was concentrated and purified by silica gel column chromatography on silica gel (PE/EA=2/1) to give 3-nitro-N-(5-(3-((1S)-3-(trifluoromethoxy)cyclopentyl)phenyl)-4-(2-(trifluoromethyl)phenyl)pyrimidin-2-yl) benzenesulfonamide (165 mg; 78.9%) as yellow solid.

LCMS: LC retention time 2.27 min. MS (ESI) m/z 653 $[M+H]^+$

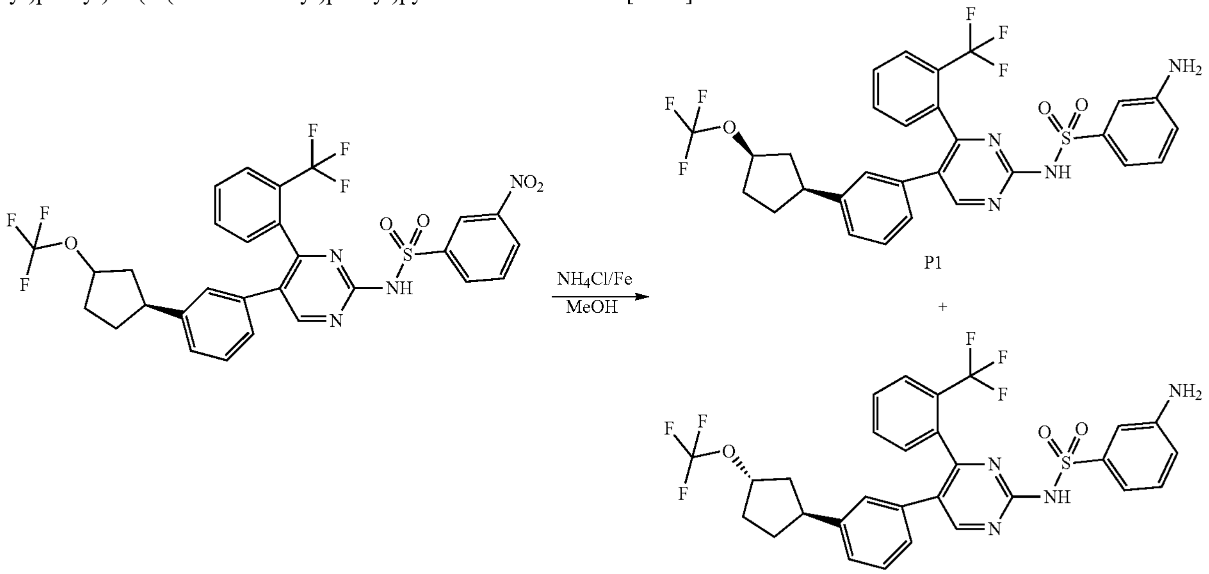

P1

+

P2

To a solution of 3-nitro-N-(5-(3-((1S)-3-(trifluoromethoxy)cyclopentyl)phenyl)-4-(2-(trifluoromethyl)phenyl)pyrimidin-2-yl)benzenesulfonamide (165 mg, 0.253 mmol) in MeOH (8 mL) and $H_2O$ (0.8 mL) was added $NH_4Cl$ (300 mg, 5.61 mmol) and Fe (290 mg, 5.20 mmol). The resulting mixture was stirred at 60° C. for 2 hours. The mixture was poured into water (50 mL) and extracted with EA (50 mL×2). The extracts were washed with water (50 mL×2), dried over sodium sulfate and evaporated. The crude product thus obtained was purified by prep-HPLC to give 3-amino-N-(5-(3-((1S,3R)-3-(trifluoromethoxy)cyclopentyl)phenyl)-4-(2-(trifluoromethyl) phenyl)pyrimidin-2-yl) benzenesulfonamide P1 (27.2 mg, 17.3%) and P2 (33.2 mg, 21.1%) as white solid.

P1: LCMS: LC retention time 1.71 min. MS (ESI) m/z 623 $[M+H]^+$ $^1H$ NMR (400 MHz, methanol-$d_4$) □ δ 8.54 (s, 1H), 7.72-7.69 (m, 1H), 7.57-7.23 (m, 2H), 7.36 (t, J=2.0 Hz, 1H), 7.30-7.27 (m, 1H), 7.22-7.20 (m, 1H), 7.18-7.15 (m, 2H), 7.11 (d, J=8.0 Hz, 1H), 7.02 (d, J=7.6 Hz, 1H), 6.90-6.87 (m, 2H), 4.85-4.79 (m, 1H), 2.98-2.89 (m, 1H), 2.42-2.34 (m, 1H), 1.99-1.85 (m, 3H), 1.55-1.45 (m, 2H) ppm.

P2: LCMS: LC retention time 1.71 min; MS (ESI) m/z 623 $[M+H]^+$ $^1H$ NMR (400 MHz, methanol-$d_4$) δ 8.54 (s, 1H), 7.73-7.71 (m, 1H), 7.56-7.52 (m, 2H), 7.35 (t, J=2.0 Hz, 1H), 7.28 (d, J=7.6 Hz, 1H), 7.22-7.16 (m, 3H), 7.10 (d, J=8.0 Hz, 1H), 7.01 (d, J=8.0 Hz, 1H), 6.88 (t, J=7.2 Hz, 2H), 4.89-4.81 (m, 1H), 3.21-3.11 (m, 1H), 2.21-1.85 (m, 4H), 1.55-1.32 (m, 2H) ppm.

The stereochemistry of P1 and P2 were assigned arbitrarily.

Example 30a 3-amino-N-(5-(3-((1R,3S)-3-(trifluoromethoxy)cyclopentyl)phenyl)-4-(2-(trifluoromethyl)phenyl)pyrimidin-2-yl)benzenesulfonamide

P1

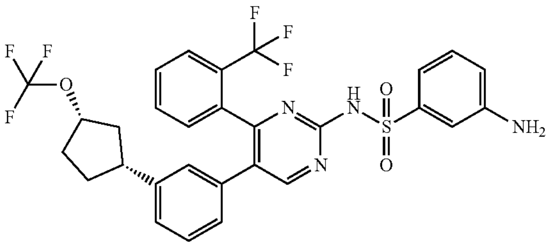

Example 30b 3-amino-N-(5-(3-((1R,3R)-3-(trifluoromethoxy)cyclopentyl)phenyl)-4-(2-(trifluoromethyl)phenyl)pyrimidin-2-yl)benzenesulfonamide

P2

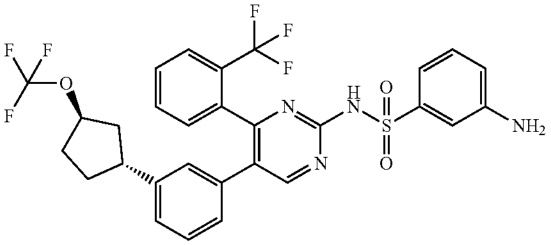

Example 30a and 30b (P1 and P2) were synthesized by essentially the same manner as Example 28, P1 and P2, starting from 1-bromo-3-((1R)-3-(trifluoromethoxy)cyclopentyl)benzene and 2-(3-((1S)-3-(trifluoromethoxy)cyclopentyl)phenyl)-1-(2-(trifluoromethyl)phenyl)ethan-1-one.

P1: LCMS: LC retention time 2.163 min. MS (ESI) m/z 623 $[M+H]^+$.

$^1H$ NMR (400 MHz, methanol-$d_4$) δ 8.54 (s, 1H), 7.72-7.70 (m, 1H), 7.57-7.53 (m, 2H), 7.35 (s, 1H), 7.29-7.01 (m, 5H), 7.03-7.01 (m, 1H), 6.90-6.88 (m, 2H), 4.92-4.81 (m, 1H), 2.95-2.91 (m, 1H), 2.39-2.36 (m, 1H), 1.97-1.87 (m, 3H), 1.53-1.47 (m, 2H).

P2: LCMS: LC retention time 2.184 min. MS (ESI) m/z 623 [M+H]*.

$^1H$ NMR (400 MHz, methanol-$d_4$) δ 8.54 (s, 1H), 7.73-7.71 (m, 1H), 7.58-7.54 (m, 2H), 7.35 (s, 1H), 7.29-7.10 (m, 5H), 7.03-7.89 (m, 1H), 6.88-6.86 (m, 2H), 4.96-4.84 (m, 1H), 3.33-3.13 (m, 1H), 2.12-1.83 (m, 4H), 1.69-1.95 (m, 1H), 1.39-1.31 (m, 2H).

The stereochemistry of P1 and P2 were assigned arbitrarily.

Biological Assays

Example 31: TECC24 AUC Fold Over DMSO @ 3 μM

The effects of a test agent on CFTR-mediated transepithelial chloride transport was measured using TECC24 recording analysis. Test agents were solubilized in DMSO. Solubilized test agents were mixed with incubation medium containing DMEM/F12, Ultroser G (2%; Crescent Chemical, catalog #67042), Hyclone Fetal Clone II (2%; GE Healthcare, catalog #SH30066.02), bovine brain extract (0.25%; Lonza, catalog #CC-4098), insulin (2.5 μg/mL), IL-13 (10 ng/mL), hydrocortisone (20 nM), transferrin (2.5 μg/mL), triiodothyronine (500 nM), ethanolamine (250 nM), epinephrine (1.5 μM), phosphoethanolamine (250 nM), and retinoic acid (10 nM). Primary human bronchial epithelial cells from a ΔF508 homozygous CF donor (CF-HBE cells; from University of North Carolina Cystic Fibrosis Tissue Procurement Center), grown on Transwell HTS 24-well cell culture inserts (Costar, catalog #3378), were exposed to test agents or controls dissolved in incubation medium. The CF-HBE cells were cultured at 36.5° C. for 48 hours before TECC24 recordings were performed in the presence or absence of test agent, a positive control or vehicle (DMSO).

Following incubation, the transwell cell culture inserts containing the test agent or control-treated CF-HBE cells were loaded onto a TECC24 apparatus (TECC v7 or MTECC v2; EP Design) to record the transepithelial voltage (VT) and resistance (TEER) using 4 AgCl electrodes per well configured in current-clamp mode. The apical and basolateral bath solutions both contained (in mM) 140 NaCl, 5 KCl, 2 $CaCl_2$), 1 $MgCl_2$, 10 Hepes, and 10 glucose (adjusted to pH 7.4 with NaOH). To inhibit basal Na+ absorption, the ENaC inhibitor benzamil (10 μM) was added to the bath. Then, the adenylate cyclase activator, forskolin (10 μM), was added to the bath to activate CFTR. The forskolin-stimulated Cl-transport was halted by addition of bumetanide (20 μM), an inhibitor of the basolateral chloride co-transporter NKCC1, to the bath to confirm that the detected signal was chloride dependent. VT and TEER recordings were digitally acquired at routine intervals using TECC or MTECC software (EP Design). VT and TEER were transformed into equivalent transepithelial Cl-current (IEQ), and the Area Under the Curve (AUC) of the IEQ time course between forskolin and bumetanide addition is generated using Excel (Microsoft). Efficacy is expressed as the ratio of the test agent AUC divided by vehicle AUC. EC50s based on AUC are generated using the non-linear regression log(agonist) vs. response function in Prism software (GraphPad) with Hill Slope fixed=1.

If a test agent increased the AUC of the forskolin-stimulated IEQ relative to vehicle in CF-HBE cells, and this increase was inhibited by bumetanide, then the test agent was considered a CFTR corrector.

Data for Examples 1-30 are provided in Table 1 below.

TABLE 1

| EXAMPLE NO. | TECC24 AUC vs. DMSO (@3 μM) |
|---|---|
| 1 | A |
| 2 | A |
| 3 | A |
| 4 | A |

TABLE 1-continued

| EXAMPLE NO. | TECC24 AUC vs. DMSO (@3 μM) |
|---|---|
| 5 | A |
| 6a | B |
| 6b | A |
| 7a | C |
| 7b | B |
| 8a | C |
| 8b | B |
| 9a | C |
| 9b | C |
| 10a | C |
| 10b | C |
| 11 | C |
| 12 | B |
| 13 | C |
| 14 | C |
| 15 | A |
| 16 | A |
| 17 | C |
| 18 | C |
| 19 | A |
| 20 | A |
| 21 | A |
| 22 | C |
| 23 | B |
| 24 | C |
| 25 | C |
| 26 | C |
| 27a | B |
| 27b | A |
| 28a | A |
| 28b | A |
| 29a | B |
| 29b | B |
| 30a | B |
| 30b | A |

ND = Not determined;
"A "refers to AUC > 5;
"B" refers to AUC between 2-5;
"C" refers to AUC < 2.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound of Formula (I):

(I)

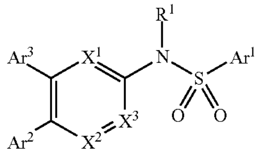

or a pharmaceutically acceptable salt thereof, wherein:

$R^1$ is hydrogen or $C_{1-6}$ alkyl;

$Ar^1$ is aryl or 5-6 membered heteroaryl substituted with 0-3 occurrences of $R^2$;

each $R^2$ is independently halo, $C_{1-6}$ alkyl, $C_{1-6}$ haloalkyl, $C_{1-6}$ alkoxy, $C_{1-6}$ haloalkoxy, —$NR^aR^b$ or 3-8 membered heterocyclyl substituted with 0-3 occurrences of $R^5$;

$Ar^2$ is aryl or 5-6 membered heteroaryl substituted with 1-3 occurrences of $R^3$;

each $R^3$ is independently halo, $C_{1-6}$ alkyl, $C_{1-6}$ alkoxy, $C_{1-6}$ haloalkoxy, $C_{3-8}$ cycloalkyl substituted with 0-3 occurrences of $R^5$ or 3-8 membered heterocyclyl substituted with 0-3 occurrences of $R^5$;

$Ar^3$ is aryl or 5-6 membered heteroaryl substituted with 1-3 occurrences of $R^4$;

each $R^4$ is independently halo, $C_{1-6}$ alkyl, $C_{1-6}$ haloalkyl, $C_{1-6}$ alkoxy or $C_{1-6}$ haloalkoxy;

$R^a$ is H or $C_{1-4}$ alkyl;

$R^b$ is H, $C_{1-4}$ alkyl, —$SO_2$—$C_{1-6}$ alkyl, $C_{3-8}$ cycloalkyl or 3-8 membered heterocyclyl substituted with 0-3 occurrences of $R^5$; and each $R^5$ is independently hydroxyl, $CO_2H$, $C_{1-4}$ alkyl, $C_{1-4}$ alkoxy, $C_{1-4}$ haloalkyl or $C_{1-4}$ haloalkoxy; and wherein, $X^1$ is N, and $X^2$ and $X^3$ are CH;

$X^1$ and $X^2$ are N, and $X^3$ is CH; or $X^1$ and $X^3$ are N, and $X^2$ is CH.

2. The compound of claim 1, wherein $R^1$ is hydrogen.

3. The compound of claim 1, wherein $Ar^1$ is aryl substituted with 0-3 occurrences of $R^2$.

4. The compound of claim 1, wherein $Ar^1$ is unsubstituted phenyl.

5. The compound of claim 1, wherein $Ar^1$ is phenyl substituted with 1 occurrence of $R^2$.

6. The compound of claim 5, wherein $R^2$ is —$NR^aR^b$.

7. The compound of claim 6, wherein $R^a$ is hydrogen and $R^b$ is hydrogen.

8. The compound of claim 6, wherein $R^a$ is hydrogen and $R^b$ is —$SO_2$—$C_{1-6}$ alkyl.

9. The compound of claim 6, wherein $R^a$ is hydrogen and $R^b$ is $C_{3-8}$ cycloalkyl substituted with 0-3 occurrences of $R^5$.

10. The compound of claim 9, wherein $R^a$ is hydrogen and $R^b$ is cyclobutyl substituted with 2 occurrences of $R^5$.

11. The compound of claim 10, wherein one occurrence of $R^5$ is hydroxyl and the other occurrence of $R^5$ is $C_{1-4}$ alkyl.

12. The compound of claim 1, wherein $Ar^1$ is a 5-6 membered heteroaryl substituted with 0-3 occurrences of $R^2$.

13. The compound of claim 12, wherein $Ar^1$ is pyrazolyl.

14. The compound of claim 13, wherein $Ar^1$ is 4-pyrazolyl substituted with 2 occurrences of $R^2$.

15. The compound of claim 14, wherein both $R^2$ are $C_{1-6}$ alkyl.

16. The compound of claim 1, wherein $Ar^1$ is a 6-membered heteroaryl substituted with 0-3 occurrences of $R^2$.

17. The compound of claim 16, wherein $Ar^1$ is pyridinyl.

18. The compound of claim 17, wherein $Ar^1$ is 2-pyridinyl substituted with 0 or 1 occurrence of $R^2$.

19. The compound of claim 18, wherein $R^2$ is halo or —$NR^aR^b$.

20. The compound of claim 18, wherein $R^2$ is 3-8 membered heterocyclyl substituted with 0-3 occurrences of $R^5$.

21. The compound of claim 20, wherein $R^2$ is piperidinyl.

22. The compound of claim 21, wherein $R^2$ is 1-piperidinyl substituted with 2 occurrences of $R^5$.

23. The compound of claim 22, wherein one occurrence of $R^5$ is hydroxyl and the other occurrence of $R^5$ is $C_{1-4}$ alkyl.

24. The compound of claim 1, wherein $Ar^2$ is aryl substituted with 1-3 occurrences of $R^3$.

25. The compound of claim 24, wherein $Ar^2$ is phenyl substituted with 1 occurrence of $R^3$.

26. The compound of claim 25, wherein $R^3$ is $C_{1-6}$ alkoxy or $C_{1-6}$ haloalkoxy.

27. The compound of claim 26, wherein $R^3$ is selected from 2,2-dimethylpropoxy, 3,3-dimethylbutoxy, trifluoromethoxy, 2,2,2-trifluoroethoxy, 2,2-difluoro-3,3-dimethylbutoxy and 2,2-dimethyl-3,3,3-trifluoropropoxy.

28. The compound of claim 25, wherein $R^3$ is $C_{3-8}$ cycloalkyl substituted with 0-3 occurrences of $R^5$.

29. The compound of claim 28, wherein $R^3$ is cyclopentyl substituted with 1 occurrence of $R^5$, wherein $R^5$ is $C_{1-4}$ haloalkoxy.

30. The compound of claim 24, wherein $Ar^2$ is phenyl substituted with 2 occurrences of $R^3$.

31. The compound of claim 30, wherein one occurrence of $R^3$ is halo and the other occurrence of $R^3$ is $C_{1-6}$ alkoxy.

32. The compound of claim 30, wherein one occurrence of $R^3$ is halo and the other occurrence of $R^3$ is $C_{1-6}$ haloalkoxy.

33. The compound of claim 1, wherein $Ar^2$ is 5-6 membered heteroaryl substituted with 1-3 occurrences of $R^3$.

34. The compound of claim 33, wherein $Ar^2$ is 1-pyrazolyl substituted with 1 occurrence of $R^3$.

35. The compound of claim 34, wherein $R^3$ is $C_{1-6}$ haloalkoxy.

36. The compound of claim 1, wherein $Ar^3$ is aryl substituted with 1-3 occurrences of $R^4$.

37. The compound of claim 36, wherein $Ar^3$ is phenyl substituted with 1 occurrence of $R^4$.

38. The compound of claim 37, wherein $R^4$ is $C_{1-6}$ alkyl or $C_{1-6}$ haloalkyl.

39. The compound of claim 36, wherein $Ar^3$ is phenyl substituted with 2 occurrences of $R^4$.

40. The compound of claim 39, wherein one occurrence of $R^4$ is $C_{1-6}$ alkyl.

41. The compound of claim 39, wherein both occurrences of $R^4$ are $C_{1-6}$ alkyl.

42. A compound selected from

| # | Compound |
|---|---|
| 2 | 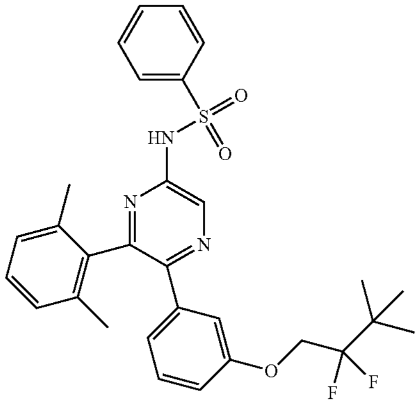 [SMILES: Cc1cccc(C)c1-c1nc(NS(=O)(=O)c2ccccc2)cnc1-c1cccc(OCC(F)(F)C(C)(C)C)c1] |
| 5 | 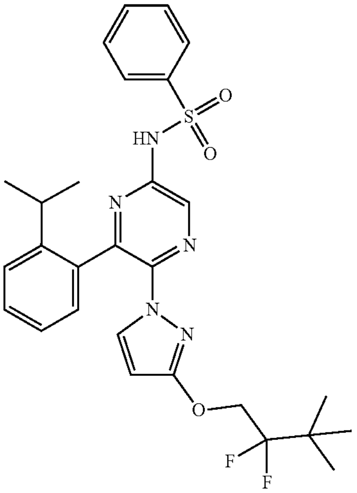 [SMILES: CC(C)c1ccccc1-c1nc(NS(=O)(=O)c2ccccc2)cnc1-n1ccc(OCC(F)(F)C(C)(C)C)n1] |
| 9b | 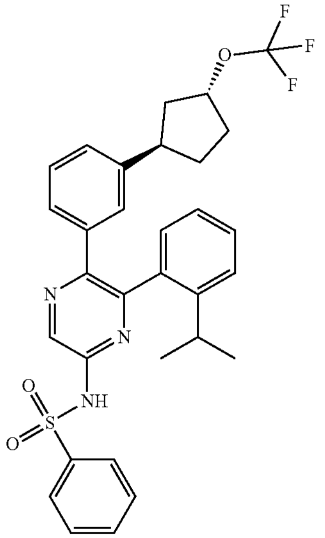 [SMILES: CC(C)c1ccccc1-c1nc(NS(=O)(=O)c2ccccc2)cnc1-c1cccc([C@@H]2CC[C@@H](OC(F)(F)F)C2)c1] |

-continued
| # | Compound |
|---|---|
| 27b | 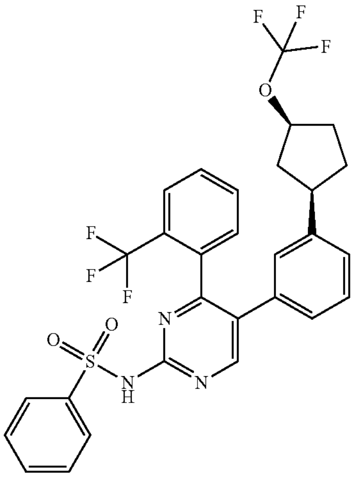 [SMILES: O=S(=O)(Nc1ncc(-c2cccc([C@@H]3CC[C@H](OC(F)(F)F)C3)c2)c(-c2ccccc2C(F)(F)F)n1)c1ccccc1] |
| 14 | 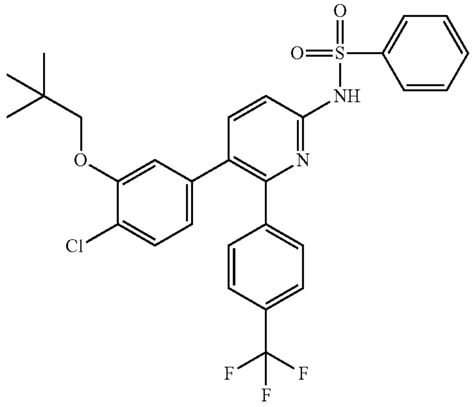 [SMILES: CC(C)(C)COc1cc(-c2ccc(NS(=O)(=O)c3ccccc3)nc2-c2ccc(C(F)(F)F)cc2)ccc1Cl] |
| 8b | 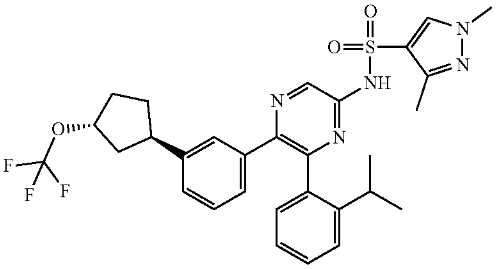 [SMILES: Cc1nn(C)cc1S(=O)(=O)Nc1cnc(-c2cccc([C@@H]3CC[C@@H](OC(F)(F)F)C3)c2)c(-c2ccccc2C(C)C)n1] |
| 18 | 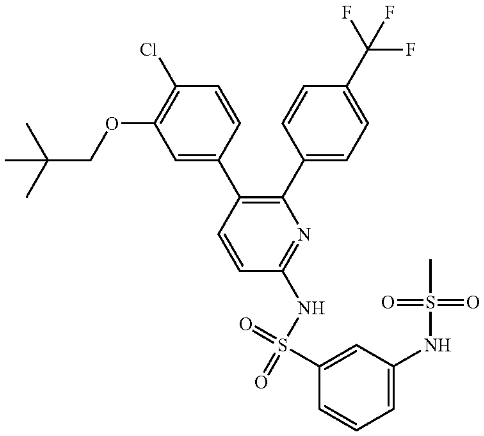 [SMILES: CC(C)(C)COc1cc(-c2ccc(NS(=O)(=O)c3cccc(NS(C)(=O)=O)c3)nc2-c2ccc(C(F)(F)F)cc2)ccc1Cl] |
-continued
| # | Compound |
|---|---|
| 8a | 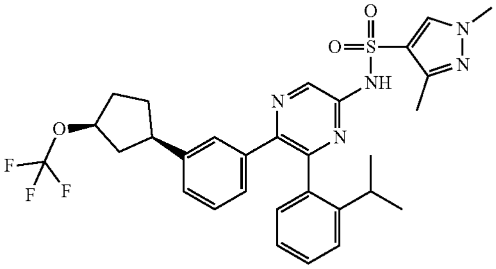 [SMILES: Cc1nn(C)cc1S(=O)(=O)Nc1cnc(-c2cccc([C@@H]3CC[C@H](OC(F)(F)F)C3)c2)c(-c2ccccc2C(C)C)n1] |
| 29b | 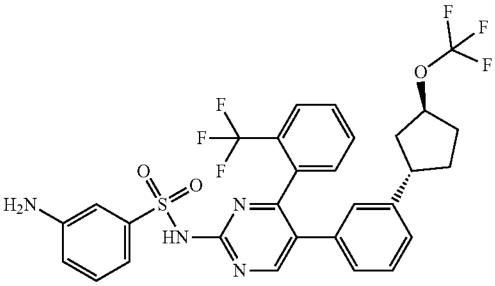 [SMILES: Nc1cccc(S(=O)(=O)Nc2ncc(-c3cccc([C@H]4CC[C@H](OC(F)(F)F)C4)c3)c(-c3ccccc3C(F)(F)F)n2)c1] |
| 30a | 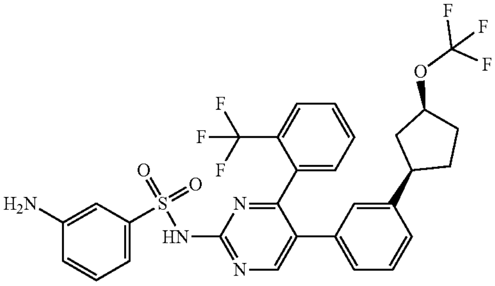 [SMILES: Nc1cccc(S(=O)(=O)Nc2ncc(-c3cccc([C@@H]4CC[C@H](OC(F)(F)F)C4)c3)c(-c3ccccc3C(F)(F)F)n2)c1] |
| 29a | 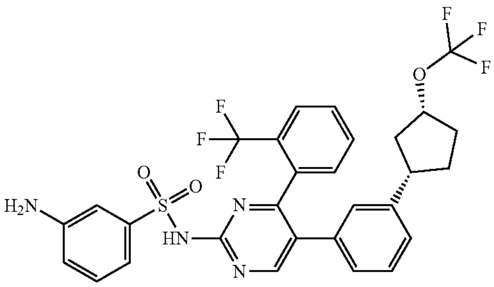 [SMILES: Nc1cccc(S(=O)(=O)Nc2ncc(-c3cccc([C@H]4CC[C@@H](OC(F)(F)F)C4)c3)c(-c3ccccc3C(F)(F)F)n2)c1] |

-continued
| # | Compound |
|---|---|
| 6a | 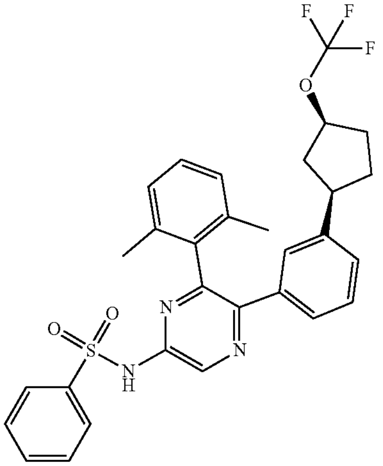 [SMILES: Cc1cccc(C)c1-c1nc(NS(=O)(=O)c2ccccc2)cnc1-c1cccc([C@@H]2CC[C@H](OC(F)(F)F)C2)c1] |
| 24 | 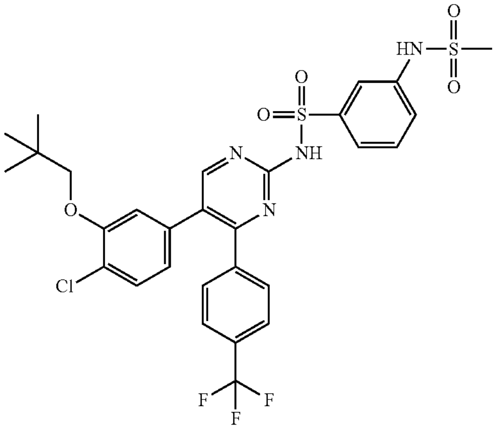 [SMILES: CC(C)(C)COc1cc(-c2cnc(NS(=O)(=O)c3cccc(NS(C)(=O)=O)c3)nc2-c2ccc(C(F)(F)F)cc2)ccc1Cl] |
| 26 | 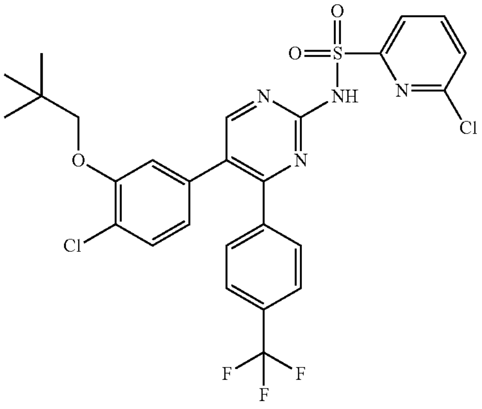 [SMILES: CC(C)(C)COc1cc(-c2cnc(NS(=O)(=O)c3cccc(Cl)n3)nc2-c2ccc(C(F)(F)F)cc2)ccc1Cl] |
-continued
| # | Compound |
|---|---|
| 28a | 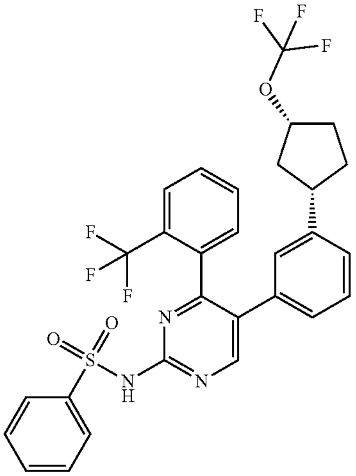 [SMILES: O=S(=O)(Nc1ncc(-c2cccc([C@H]3CC[C@@H](OC(F)(F)F)C3)c2)c(-c2ccccc2C(F)(F)F)n1)c1ccccc1] |
| 27a | 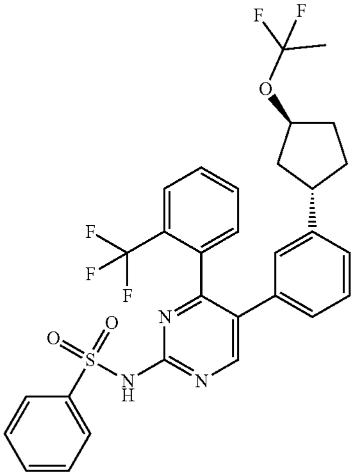 [SMILES: CC(F)(F)O[C@H]1CC[C@H](c2cccc(-c3cnc(NS(=O)(=O)c4ccccc4)nc3-c3ccccc3C(F)(F)F)c2)C1] |
| 22 | 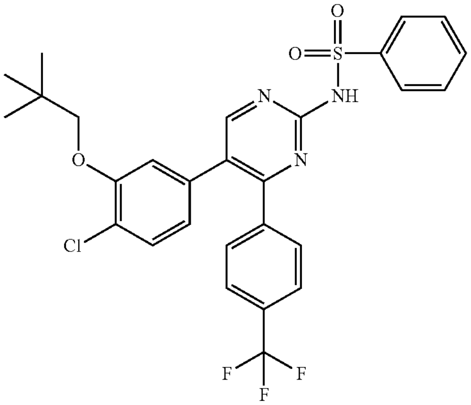 |

-continued
| # | Compound |
|---|---|
| 28b | 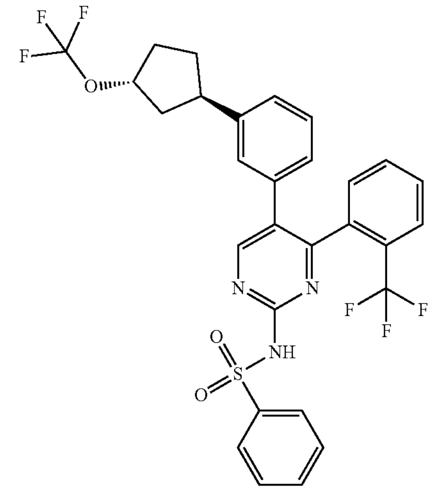 [SMILES: O=S(=O)(Nc1ncc(-c2cccc([C@@H]3CC[C@@H](OC(F)(F)F)C3)c2)c(-c2ccccc2C(F)(F)F)n1)c1ccccc1] |
| 7a | 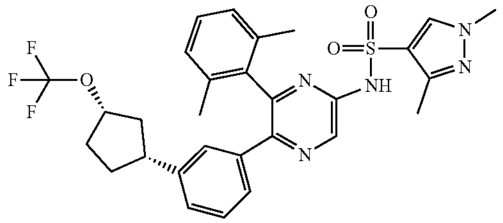 [SMILES: Cc1cccc(C)c1-c1nc(NS(=O)(=O)c2cn(C)nc2C)cnc1-c1cccc([C@@H]2CC[C@H](OC(F)(F)F)C2)c1] |
| 17 | 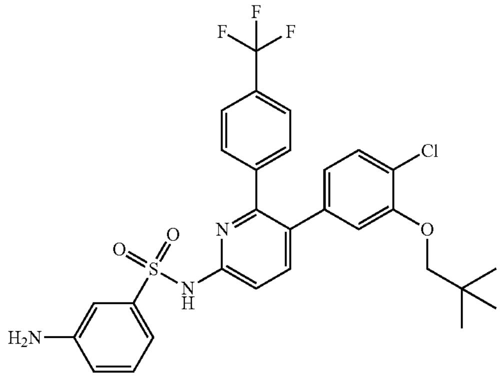 [SMILES: CC(C)(C)COc1cc(-c2ccc(NS(=O)(=O)c3cccc(N)c3)nc2-c2ccc(C(F)(F)F)cc2)ccc1Cl] |
| 19 | 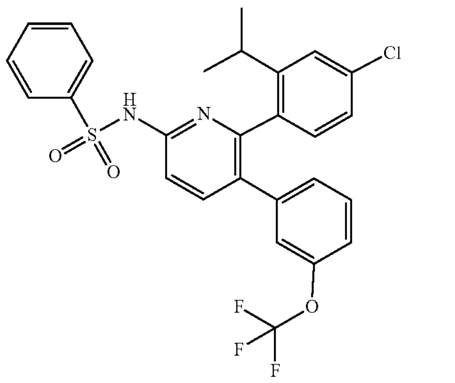 [SMILES: CC(C)c1cc(Cl)ccc1-c1nc(NS(=O)(=O)c2ccccc2)ccc1-c1cccc(OC(F)(F)F)c1] |
-continued
| # | Compound |
|---|---|
| 30b | 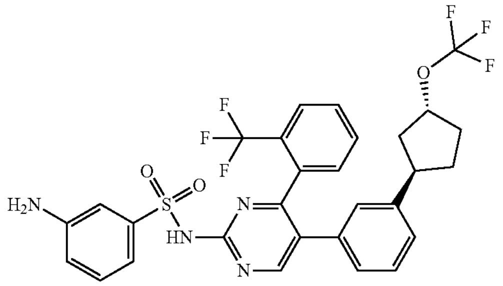 [SMILES: Nc1cccc(S(=O)(=O)Nc2ncc(-c3cccc([C@@H]4CC[C@@H](OC(F)(F)F)C4)c3)c(-c3ccccc3C(F)(F)F)n2)c1] |
| 21 | 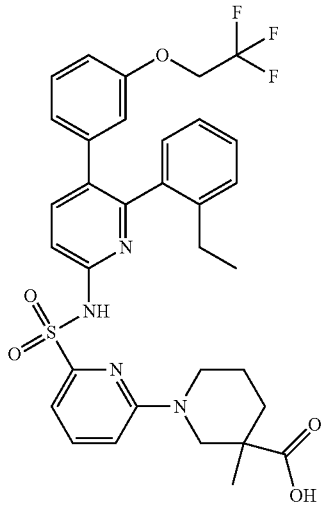 [SMILES: CCc1ccccc1-c1nc(NS(=O)(=O)c2cccc(N3CCCC(C)(C(=O)O)C3)n2)ccc1-c1cccc(OCC(F)(F)F)c1] |
| 15 | 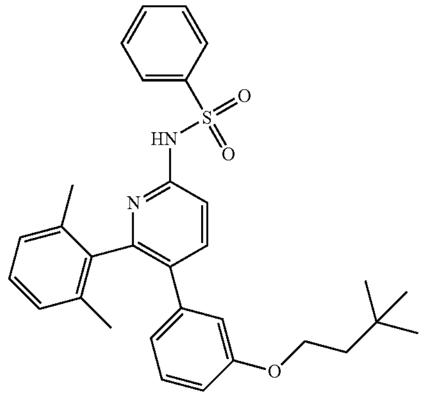 [SMILES: Cc1cccc(C)c1-c1nc(NS(=O)(=O)c2ccccc2)ccc1-c1cccc(OCCC(C)(C)C)c1] |

| # | Compound |
|---|---|
| 12 | 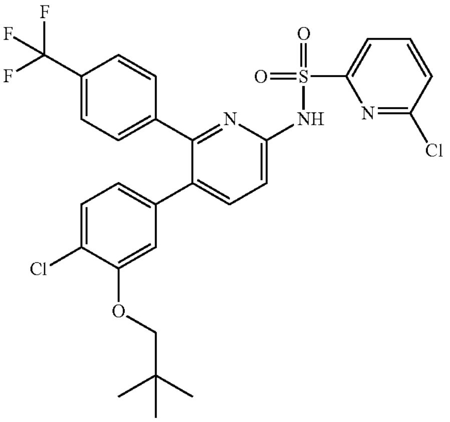 [SMILES: CC(C)(C)COc1cc(-c2ccc(NS(=O)(=O)c3cccc(Cl)n3)nc2-c2ccc(C(F)(F)F)cc2)ccc1Cl] |
| 6b | 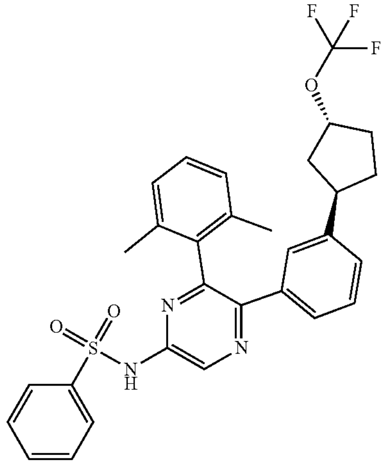 [SMILES: Cc1cccc(C)c1-c1nc(NS(=O)(=O)c2ccccc2)cnc1-c1cccc([C@@H]2CC[C@@H](OC(F)(F)F)C2)c1] |
| 16 | 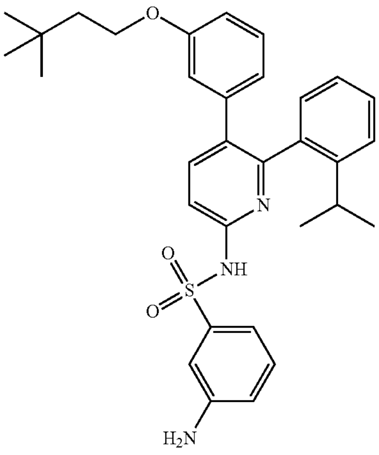 [SMILES: CC(C)c1ccccc1-c1nc(NS(=O)(=O)c2cccc(N)c2)ccc1-c1cccc(OCCC(C)(C)C)c1] |
| # | Compound |
|---|---|
| 4 | 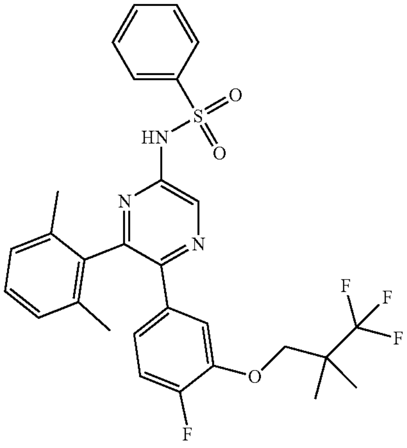 [SMILES: Cc1cccc(C)c1-c1nc(NS(=O)(=O)c2ccccc2)cnc1-c1ccc(F)c(OCC(C)(C)C(F)(F)F)c1] |
| 20 | 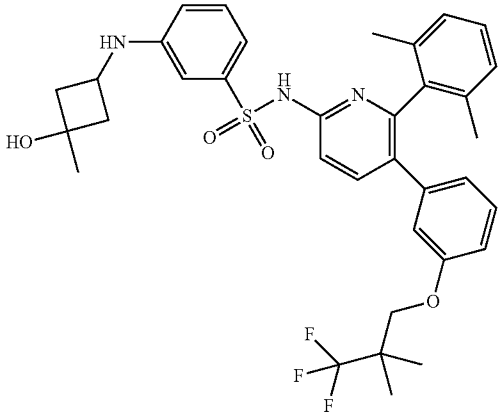 [SMILES: Cc1cccc(C)c1-c1nc(NS(=O)(=O)c2cccc(NC3CC(C)(O)C3)c2)ccc1-c1cccc(OCC(C)(C)C(F)(F)F)c1] |
| 10a | 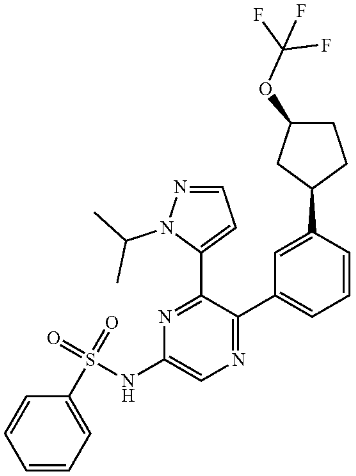 [SMILES: CC(C)n1nccc1-c1nc(NS(=O)(=O)c2ccccc2)cnc1-c1cccc([C@@H]2CC[C@H](OC(F)(F)F)C2)c1] |
| 11 | 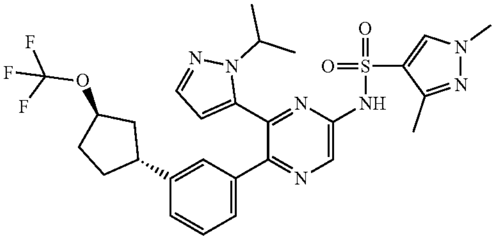 [SMILES: Cc1nn(C)cc1S(=O)(=O)Nc1cnc(-c2cccc([C@@H]3CC[C@@H](OC(F)(F)F)C3)c2)c(-c2ccnn2C(C)C)n1] |

-continued
| # | Compound |
|---|---|
| 23 | 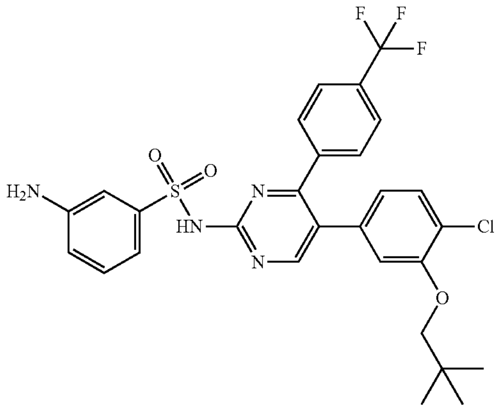 [SMILES: CC(C)(C)COc1cc(-c2cnc(NS(=O)(=O)c3cccc(N)c3)nc2-c2ccc(C(F)(F)F)cc2)ccc1Cl] |
| 3 | 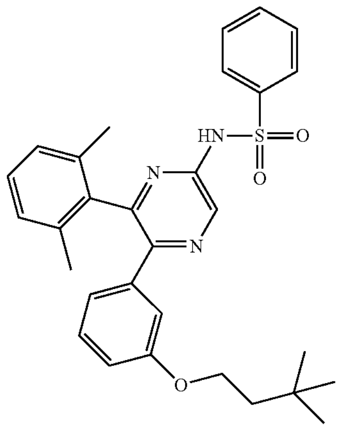 [SMILES: Cc1cccc(C)c1-c1nc(NS(=O)(=O)c2ccccc2)cnc1-c1cccc(OCCC(C)(C)C)c1] |
| 13 | 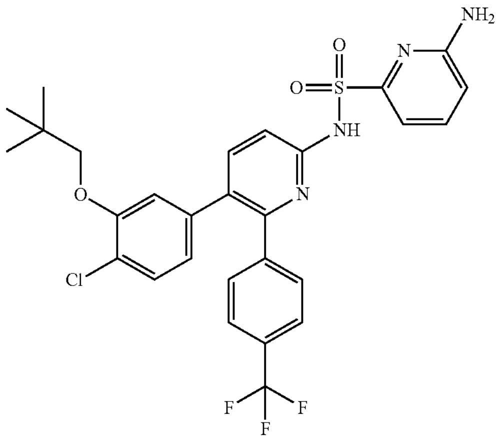 [SMILES: CC(C)(C)COc1cc(-c2ccc(NS(=O)(=O)c3cccc(N)n3)nc2-c2ccc(C(F)(F)F)cc2)ccc1Cl] |
-continued
| # | Compound |
|---|---|
| 10b | 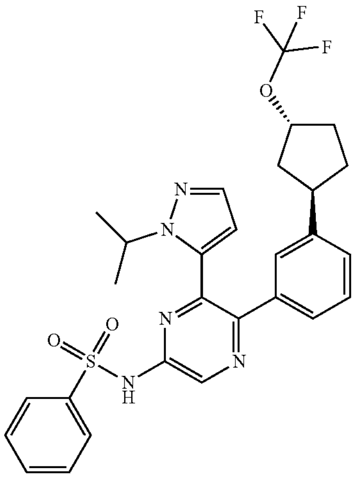 [SMILES: CC(C)n1nccc1-c1nc(NS(=O)(=O)c2ccccc2)cnc1-c1cccc([C@@H]2CC[C@@H](OC(F)(F)F)C2)c1] |
| 25 | 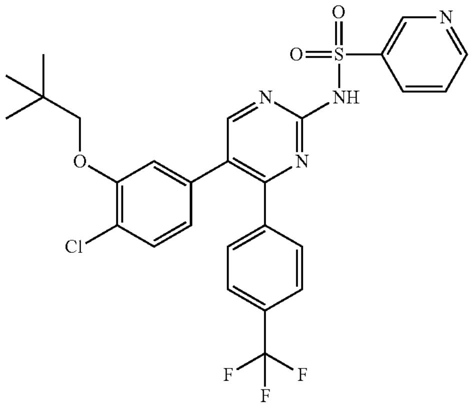 [SMILES: CC(C)(C)COc1cc(-c2cnc(NS(=O)(=O)c3cccnc3)nc2-c2ccc(C(F)(F)F)cc2)ccc1Cl] |
| 1 | 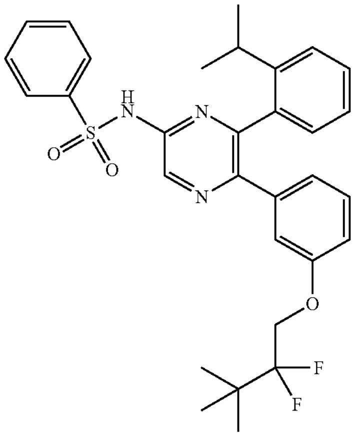 [SMILES: CC(C)c1ccccc1-c1nc(NS(=O)(=O)c2ccccc2)cnc1-c1cccc(OCC(F)(F)C(C)(C)C)c1] |

-continued

| # | Compound |
|---|---|
| 9a | 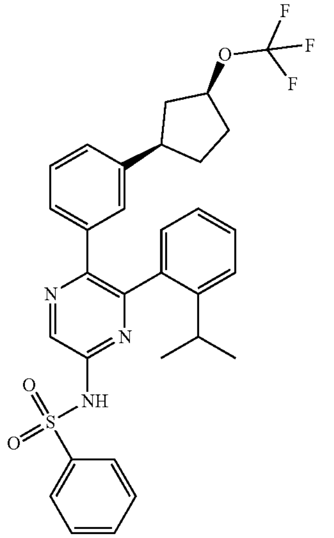 [SMILES: CC(C)c1ccccc1-c1nc(NS(=O)(=O)c2ccccc2)cnc1-c1cccc([C@@H]2CC[C@H](OC(F)(F)F)C2)c1] |

-continued

| # | Compound |
|---|---|
| 7b | 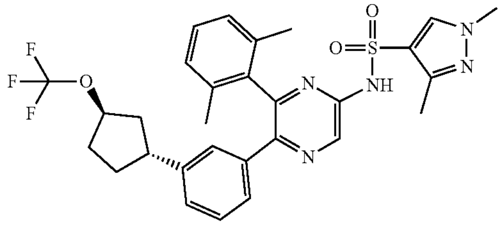 [SMILES: Cc1cccc(C)c1-c1nc(NS(=O)(=O)c2cn(C)nc2C)cnc1-c1cccc([C@@H]2CC[C@@H](OC(F)(F)F)C2)c1] |

or a pharmaceutically acceptable salt, thereof.

43. A pharmaceutical composition comprising a compound of claim 1, and a pharmaceutically acceptable carrier or excipient.

44. The pharmaceutical composition of claim 43, further comprising one or more cystic fibrosis transmembrance conductance receptor (CFTR) therapeutic agents.

* * * * *